(12) United States Patent
Sasaki et al.

(10) Patent No.: US 10,464,920 B2
(45) Date of Patent: Nov. 5, 2019

(54) VICINAL PRIMARY DIAMINES ASSOCIATED WITH METAL AND/OR FREE RADICAL CHELATION MOTIFS, AND ACTIVE AGAINST CARBONYL AND OXIDATIVE STRESS, AND USE THEREOF

(71) Applicants: UNIVERSITE AMIENS PICARDIE JULES VERNE, Amiens (FR); CENTRE HOSPITALIER UNIVERSITAIRE, Amiens (FR); CENTRE NATIONAL DE LA RECHERCHE SCIENTIFIQUE-CNRS-, Paris (FR); INSERM (INSTITUT NATIONAL DE LA SANTÉ ET DE LA RECHERCHE MÉDICALE), Paris (FR)

(72) Inventors: Nobumichi André Sasaki, Flesselles (FR); Pascal Sonnet, Pont de Metz (FR); Agnès Boullier, Amiens (FR); Elodie Lohou, Amiens (FR)

(73) Assignees: INSERM (INSTITUTE NATIONAL DE LA SANTÉ ET DE LA RECHERCHE MÉDICALE, Paris (FR); UNIVERSITE AMIENS PICARDIE JULES VERNE, Amiens (FR); CENTRE HOSPITALIER UNIVERITAIRE, Amiens (FR); CENTRE NATIONAL DE LA RECHERCHE SCIENTIFIEQUE, Paris (FR)

( * ) Notice: Subject to any disclaimer, the term of this patent is extended or adjusted under 35 U.S.C. 154(b) by 0 days.

(21) Appl. No.: 15/742,276

(22) PCT Filed: Jul. 6, 2016

(86) PCT No.: PCT/FR2016/051703
§ 371 (c)(1),
(2) Date: Jan. 5, 2018

(87) PCT Pub. No.: WO2017/006048
PCT Pub. Date: Jan. 12, 2017

(65) Prior Publication Data
US 2018/0201602 A1  Jul. 19, 2018

(30) Foreign Application Priority Data
Jul. 6, 2015 (FR) ..................... 15 56366

(51) Int. Cl.
C07D 401/06 (2006.01)
C07C 233/09 (2006.01)
C07C 233/65 (2006.01)
C07D 213/63 (2006.01)
C07C 235/34 (2006.01)
C07C 235/56 (2006.01)
C07D 241/28 (2006.01)
C07D 295/185 (2006.01)
C07D 295/192 (2006.01)
C07D 213/69 (2006.01)
A61P 9/10 (2006.01)
(Continued)

(52) U.S. Cl.
CPC .............. *C07D 401/06* (2013.01); *A61P 9/10* (2018.01); *A61P 25/16* (2018.01); *A61P 25/28* (2018.01); *C07C 233/09* (2013.01); *C07C 233/65* (2013.01); *C07C 235/34* (2013.01); *C07C 235/56* (2013.01); *C07D 213/63* (2013.01); *C07D 213/69* (2013.01); *C07D 241/28* (2013.01); *C07D 295/185* (2013.01); *C07D 295/192* (2013.01)

(58) Field of Classification Search
CPC ... C07C 233/09; C07C 233/65; C07C 235/34; C07C 235/56; C07D 213/63; C07D 213/69; C07D 241/28; C07D 295/182; C07D 295/192; C07D 401/06; A61P 9/08; A61P 25/16; A61P 25/28
See application file for complete search history.

(56) References Cited

U.S. PATENT DOCUMENTS 9,512,176 B2  12/2016  Pharmamens
2007/0155726 A1  7/2007  Arnaiz et al.
(Continued)

FOREIGN PATENT DOCUMENTS

WO  9804537 A1  2/1998
WO  0064865 A1  11/2000
(Continued)

OTHER PUBLICATIONS

Vision Source Signature Eye Care, "Is There Any Way to Prevent Cataracts?", https://visionsource.com/blog/prevent-cataracts/, publ. Jun. 2014 (Year: 2014).*
(Continued)

*Primary Examiner* — Sarah Pihonak

(57) ABSTRACT

The invention relates to compounds of Formula I:

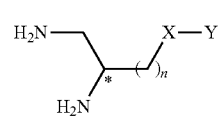

Figure 1:
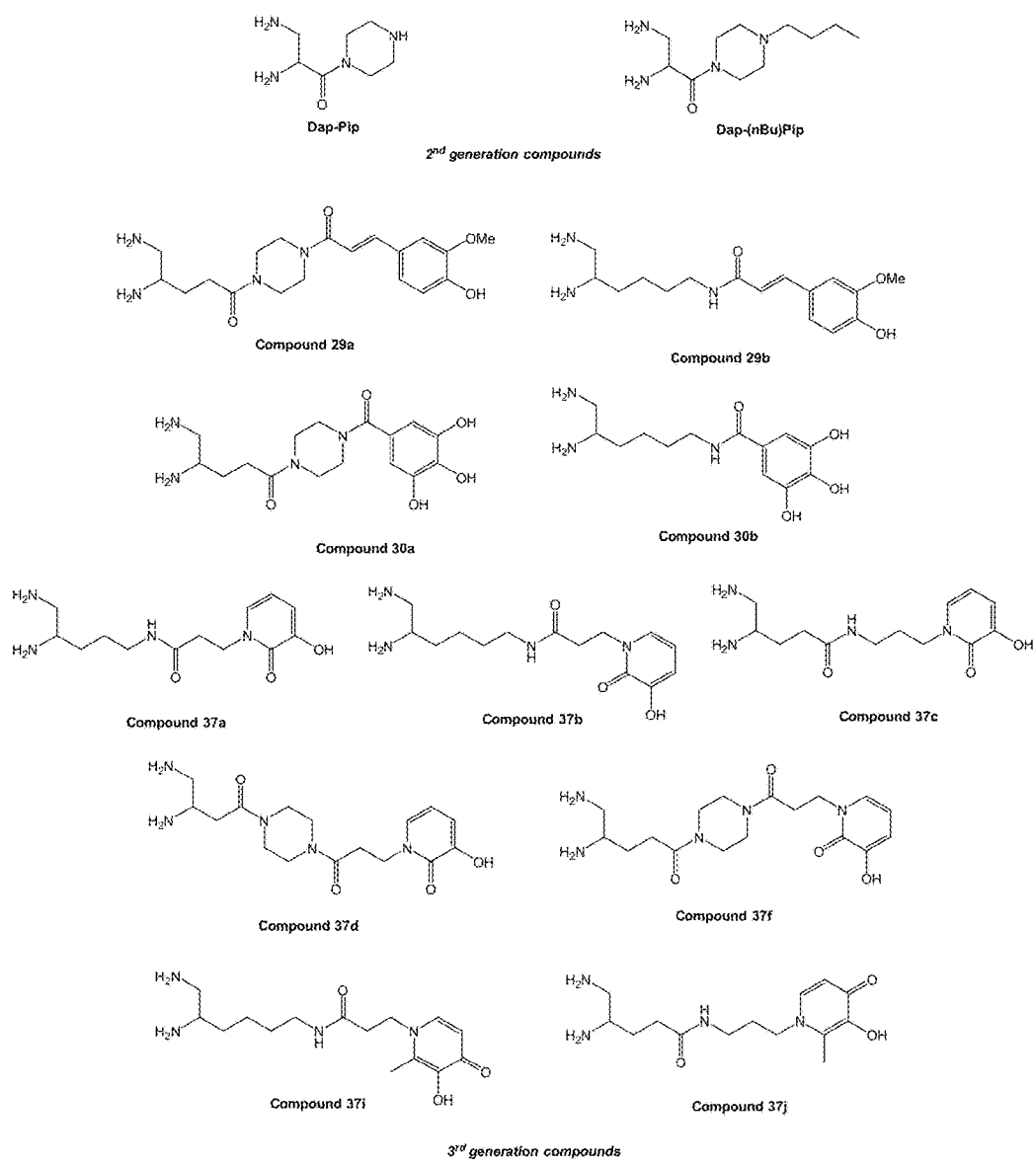

or the salts thereof, as well as the use thereof in the pharmaceutical, cosmetic or agrofood industry.

12 Claims, 29 Drawing Sheets

(51) Int. Cl.
  *A61P 25/16* (2006.01)
  *A61P 25/28* (2006.01)

(56) References Cited

U.S. PATENT DOCUMENTS

2010/0130506 A1  5/2010  Bhalay et al.
2015/0038493 A1  2/2015  Pharmamens

FOREIGN PATENT DOCUMENTS

WO     00/74664 A2    12/2000
WO     07011623 A1    1/2007
WO     2013030193 A1  3/2013

OTHER PUBLICATIONS

Wistuba et. al., Nature Reviews Clinical Oncology, vol. 8, pp. 135-141, publ. 2011 (Year: 2011).*
Feng et. al., Oxidative Med. & Cellular Longevity, vol. 2012, pp. 1-17, publ. 2012 (Year: 2012).*
Lonn et. al., Diabetes Care, vol. 25, pp. 1919-1927, publ. 2002 (Year: 2002).*
Mandal, "How to Prevent Cancer", publ. Aug. 29, 2013, http://news-medical.net/health/How-to-Prevent-Cancer.aspx (Year: 2013).*
"What Do We Know About Preventing Alzheimer's?", NIH Medline Plus, http://medlineplus.gov/magazine/issues/winter15/articles/qinter15pg11.html, publ. Dec. 2015 (Year: 2015).*
Agim et. al., "Dietary Factors in the Etiology of Parkinson's Disease", BioMed Res. Int., vol. 2015, pp. 1-16, publ. 2015 (Year: 2015).*
Raza et. al., "RA: from risk factors and pathogenesis to prevention", Rheumatology, vol. 55, pp. 1-3, publ. Jul. 2015 (Year: 2015).*
Magrioti et. al., Bioorganic and Medicinal Chemistry Letters, 2008, Elsevier, vol. 18, pp. 5424-5427 (Year: 2008).*
Peyroux et al., "Advanced glycation endproducts (AGEs): Pharmacological inhibition in diabetes," Pathol Biol (Paris). Sep. 2006; 54(7): pp. 405-419.
Negre-Salvayre et al. "Advanced lipid peroxidation end products in oxidative damage to proteins. Potential role in diseases and therapeutic prospects for the inhibitors," Br J Pharmacol. Jan. 2008; 153(1): pp. 6-20.
Kalapos, "Where does plasma methylglyoxal originate from?" Diabetes Res Clin. Pract. Mar. 2013; 99(3): pp. 260-271.
Uchida "4-Hydroxy-2-nonenal: a product and mediator of oxidative stress," Prog Lipid Res. Jul. 2003;42(4): pp. 318-343.
Del Turco et al., "An update on advanced glycation endproducts and atherosclerosis," Biofactors. Jul.-Aug. 2012;38(4): pp. 266-274.
Lee et al., "RAGE ligands induce apoptotic cell death of pancreatic B-cells via oxidative stress," International Journal of Molecular Medicine, 2010, 26, pp. 813-818.
Stirban et al., "Vascular effects of advanced glycation endproducts: Clinical effects and molecular mechanisms," Mol. Metabolism, 2014, 3, pp. 94-108.
Kalapos, "he tandem of free radicals and methylglyoxal," Chem. Biol. Interact., 2008, 171, pp. 251-271.
Butterfield et al., "Evidence of oxidative damage in Alzheimer's disease brain: central role for amyloid beta-peptide," Trends Mol. Med. 2001, 7, pp. 548-554.
Butterfield et al., "Lipid peroxidation and protein oxidation in Alzheimer's disease brain: potential causes and consequences involving amyloid beta-peptide-associated free radical oxidative stress," Free Radic. Biol. Med., 2002, 32, pp. 1050-1060.
Faller et al., "A bioinorganic view of Alzheimer's disease: when misplaced metal ions (re)direct the electrons to the wrong target," Chem. Eur. J., 2012, 18, pp. 15910-15920.
Tiiman et al., "The missing link in the amyloid cascade of Alzheimer's disease—metal ion," Neurochem. Int., 2013, 62, pp. 367-378.

Pocernich et al., "Nutritional approaches to modulate oxidative stress in Alzheimer's disease," Curr. Alzheimer Res., 2011, 8, pp. 452-469.
Bailey, "Molecular mechanisms of ageing in connective tissues," Mech. Ageing Dev., 2001, 122, pp. 735-755.
Marnett, "Oxy radicals, lipid peroxidation and DNA damage," Toxicology, 2002, 181-182, pp. 219-222.
Frischmann et al., "Identification of DNA adducts of methylglyoxal," Chem. Res. Toxicol., 2005, 18, pp. 1586-1592.
Thornalley, "Use of aminoguanidine (Pimagedine) to prevent the formation of advanced glycation endproducts," Arch. Biochem. Biophys., 2003, 419, pp. 31-40.
Nagai et al., "Chelation: a fundamental mechanism of action of AGE inhibitors, AGE breakers, and other inhibitors of diabetes complications," Diabetes, 2012, 61, pp. 549-559.
Bolton et al., "Randomized trial of an inhibitor of formation of advanced glycation end products in diabetic nephropathy," Am. J. Nephrol., 2004, 4, pp. 32-40.
Sasaki et al., "N-Terminal 2,3-diaminopropionic acid (Dap) peptides as efficient methylglyoxal scavengers to inhibit advanced glycation endproduct (AGE) formation," Bioorg. Med. Chem. 2009, 17, pp. 2310-2320.
Hipkiss et al., "Protective effects of carnosine against malondialdehyde-induced toxicity towards cultured rat brain endothelial cells," Neurosci. Lett., 1997, 238, pp. 135-1313.
Miyata et al., "Mechanism of the inhibitory effect of OPB-9195 [(+/−)-2-isopropylidenehydrazono-4-oxo-thiazolidin-5-yla cetanilide] on advanced glycation end product and advanced lipoxidation end product formation," J. Am. Soc. Nephrol., 2000, 11, pp. 1719-1725.
Gkogkolou et al., "Advanced glycation end products: Key players in skin aging?" Dermatoendocrinol. 2012, 4, pp. 259-270.
Wojciechowski et al., "A Robust and Convergent Synthesis of Dipeptide-DOTAM Conjugates as Chelators for Lanthanide Ions: New Paracest MRI Agents," Bioconjugate. Chem., 2007, 18, pp. 1625-1636.
More et al., "Inhibition of Glyoxalase I: The First Low-Nanomolar Tight-Binding Inhibitors," J. Med. Chem., 2009 52, pp. 4650-4656.
Ollivier et al., "An Entry to 1,7-Dioxaspiro[5.6]dodecanes and 1,6-Dioxaspiro[4.6]undecanes," Tetrahedron Lett., 2010, 51, pp. 4147-4149.
Matsumur et al., "New reaction conditions using trifluoroethanol for the E-I Hofmann rearrangement," J. Chem. Soc., Perkin Trans. 1, 1999, pp. 2057-2060.
Moussa et al., "Design, Synthesis, and Structure—Affinity Relationships of Regioisomeric N-Benzyl Alkyl Ether Piperazine Derivatives as σ-1 Receptor Ligands," Moussa et al. J. Med. Chem., 2010, 53, pp. 6228-6239.
Arumugam et al., "New Synthetic Approach for the Incorporation of 3,2-Hydroxypyridinone (HOPO) Ligands: Synthesis of Structurally Diverse Poly HOPO Chelators," Synthesis, 2011, pp. 57-64.
Streater et al., "Novel 3-hydroxy-2(1H)-pyridinones. Synthesis, iron(III)-chelating properties and biological activity," J. Med. Chem., 1990, 33, pp. 1749-1755.
Gai et al., "A Practical Route for the Preparation of 1,4,7-Triazacyclononanyl Diacetates with a Hydroxypyridinonate Pendant Arm," Molecules, 2015, 20, pp. 19393-19405.
Ghorai et al., "Rational construction of triazole/urea based peptidomimetic macrocycles as pseudocyclo-β-peptides and studies on their chirality controlled self-assembly," Org. Lett., 2014, 16, pp. 3196-3199.
Dobbin et al., "Synthesis, physicochemical properties, and biological evaluation of N-substituted 2-alkyl-3-hydroxy-4(1H)-pyridinones: orally active iron chelators with clinical potential," J. Med. Chem., 1998, 41, pp. 3347-3359.
Santos et al., "Synthesis, chelating properties towards gallium and biological evaluation of two N-substituted 3-hydroxy-4-pyridinones," J. Inorg. Biochem., 2000, 78, pp. 303-311.
Färber et al., "Synthesis of N-substituted 3-hydroxy-2-methyl-4-pyridones and -pyridonimines," J. Heterocyclic Chem., 1994, 31, pp. 947-956.
Green et al., "Carbohydrate-bearing 3-hydroxy-4-pyridinonato complexes of gallium(III) and indium(III)," Bioconjugate Chem. 2005, 16, pp. 1597-1609.

(56) References Cited

OTHER PUBLICATIONS

Boschelli et al., "Synthesis and Src kinase inhibitory activity of 2-phenyl- and 2-thienyl-7-phenylaminothieno[3,2-b]pyridine-6-carbonitriles," J. Med. Chem., 2005, 48, pp. 3891-3902.

Santos et al., "new bis(3-hydroxy-4-pyridinone)-IDA derivative as a potential therapeutic chelating agent. Synthesis, metal-complexation and biological assays," Dalton Trans., 2004, pp. 3772-3781.

Magdalena Karamać, "Chelation of Cu(II), Zn(II), and Fe(II) by Tannin Constituents of Selected Edible Nuts," Int. J. Mol. Sci., 2009, 10, pp. 5485-5497.

Li et al., "Antioxidant ability and mechanism of rhizoma Atractylodes macrocephala," Molecules, 2012, 17, pp. 13457-13472.

Dávalos et al., "Extending Applicability of the Oxygen Radical Absorbance Capacity (ORAC-Fluorescein) Assay," J. Agric. Food Chem.,2004 52, pp. 48-54.

Prior et al., "Standardized methods for the determination of antioxidant capacity and phenolics in foods and dietary supplements," J. Agric. Food Chem., 2005, 53, pp. 4290-4302.

Fargualy et al., "Synthesis, biological evaluation and molecular docking studies of some pyrimidine derivatives," Bioorg. Med. Chem., 2015, 23, pp. 1135-1148.

Esterbauer et al., "The role of lipid peroxidation and antioxidants in oxidative modification of LDL," Free Radic. Biol. Med., 1992, 13, pp. 341-390.

Nadeem et al., "The two faces of α- and γ-tocopherols: an in vitro and ex vivo investigation into VLDL, LDL and HDL oxidation," J. Nutr. Biochem., 2012, 23, pp. 845-851.

Kukumoto et al., "Assessing antioxidant and prooxidant activities of phenolic compounds," J. Agric. Food Chem., 2000, 48, pp. 3597-3604.

Hsieh et al., "Quercetin and ferulic acid aggravate renal carcinoma in long-term diabetic victims," J. Agric. Food Chem., 2010, 58, pp. 9273-9280.

Bukhari et al., "Synthesis of α, β-unsaturated carbonyl based compounds as acetylcholinesterase and butyrylcholinesterase inhibitors: characterization, molecular modeling, QSAR studies and effects agains amyloid β-induced cytotoxicity," Eur. J. Med. Chem., 2014, 83, pp. 355-365.

Hu et al., "Neuroprotective effects of macranthoin G from Eucommia ulmoides against hydrogen peroxide-induced apoptosis in PC12 cells via inhibiting NF-κB activation," Chem. Biol. Interact., 2014, 224, pp. 108-116.

Chen et al., "d-β-Hydroxybutyrate inhibited the apoptosis of PC12 cells induced by H2O2 via inhibiting oxidative stress," Neurochem. Int., 2013, 62, pp. 620-625.

Chen et al., "Synthesis and cytotoxic activity evaluation of novel arylpiperazine derivatives on human prostate cancer cell lines," Molecules, 2014, 19(8), pp. 12048-12064.

Zou et al., "An optimized in vitro assay for screening compounds that stimulate liver cell glucose utilization with low cytotoxicity," J. Pharmacol. Toxicol. Methods., 2007, 56(1), pp. 58-62.

Carson et al., "Apoptosis and disease." The Lancet, 1993, 341, 1251-1254.

Elmore, "Apoptos is : A Review of Programmed Cell Death Toxicol Pathol," Toxicol Pathol. 2007 ; 35(4): pp. 495-516.

Caddick et al., "A generic approach for the catalytic reduction of nitriles," Tetrahedron, 2003, 59, pp. 5417-5423.

The International Search Report, dated Sep. 26, 2016, in the corresponding PCT/FR2016/051703.

The European Communication from the Examining Division, dated Apr. 1, 2019, in the related European Patent Application No. 16750924.9.

Lohou Elodie et al: "Multifunctional diamine AGE/ALE inhibitors with potential therapeutical properties against Alzheimer's disease", European Journal of Medicinal Chemistry, Editions Scientifique Elsevier, Paris, FR, vol. 122, Apr. 30, 2016 (Apr. 30, 2016), pp. 702-722, XP029705907.

\* cited by examiner (a)

(b)

(a)

(b)

(a)

(b)

(a)

(b)

(a)

(b)

(a)

(b)

VICINAL PRIMARY DIAMINES ASSOCIATED WITH METAL AND/OR FREE RADICAL CHELATION MOTIFS, AND ACTIVE AGAINST CARBONYL AND OXIDATIVE STRESS, AND USE THEREOF

CROSS-REFERENCE TO RELATED APPLICATIONS

This application is a National Stage Application of PCT/FR2016/051703 filed Jul. 6, 2016, which claims priority from French Patent Application No. 1556366 filed Jul. 6, 2015. Each of the prior mentioned applications is hereby incorporated by reference herein in its entirety.

This invention relates to novel diamine derivatives scavengers of alpha-oxoaldehydes (α-oxoaldehydes) and alpha aldehydes, beta unsaturated (α,β-unsaturated aldehydes) and metal chelators as well as the uses thereof, in particular in the treatment and/or prevention of diseases or disorders associated with accumulation of AGE (Advanced Glycation Endproducts) and/or of ALE (Advanced Lipid Peroxidation Endproducts).

PRIOR ART

During glycolysis and lipid peroxidation, carbonyl compounds are formed and react with the nucleophilic groups of proteins (lysine, arginine, cysteine, etc.) to give AGEs ("Advanced Glycation Endproducts") (Pathologie, Biologie, 2006, 54, 405-419) and ALEs ("Advanced Lipid Peroxidation Endproducts") (Br. J. Pharm., 2008, 153, 6-20). AGEs therefore appear as deleterious modifications of proteins following the formation of a Schiff base, followed by an Amadori rearrangement, of the free amine groups thereof with different α-oxoaldehydes derivatives such as for example glyoxal (GO), methylglyoxal (MGO) and deoxyglucosone (3-DG), coming from the oxidative metabolism of the glucides (Diabetes Res. Clin. Pract. 2013, 99, 261-271). In the same way, the ALEs are formed after 1.2 or 1.4 Michael addition of these amine groups of proteins on α,β-unsaturated aldehydes such as malondialdehyde (MDA), acrolein, 4-hydroxynonenal (4-HNE) or 4-hydroxy-2-hexanal (4-HHE), coming from the degradation of polyunsaturated fatty acids under the effect of the oxidative stress induced in particular by the transition metals ($Cu^{2+}$, $Fe^{3+}$) (Prog. Lipid Res., 2003, 42, 318-343). In addition, these toxic carbonyl derivatives can also react according to a non-enzymatic process with the bases of the DNA in order to give branched or non-branched AGEs/ALEs. Enzymatic detoxification mechanisms exist such as the (GSH)-dependant glutathion glyoxalase system (glyoxalases I and II) which transforms the reactive carbonyl compounds into D-lactate, glycolate or acetol, but the malfunction thereof can cause an accumulation of AGEs.

The accumulation of AGEs has two major biological consequences. First of all, they can be at the origin of a protein cross-linking observed especially on long-lived proteins such as for example collagen, lens proteins, fibronectin, albumin and hemoglobin. This phenomenon as such plays a preponderant role in the appearance of various malfunctions (loss of elasticity of the skin tissue or of the vascular endothelium, pigmentation of the skin, etc.) and age-related pathologies (cataract, rheumatisms, etc.). Then, the oxidative stress would favour the occurrence of inflammatory and thrombogenic reactions, but also apoptosis via an interaction between the AGEs and the specific receptors thereof (RAGE). These mechanisms would as such in particular be involved in the appearance of atherosclerosis and of various complications in particular microangiopathic related to diabetes such as cardiovascular disorders, nephropathies, retinopathies, neuropathies etc. (Biofactors 2012, 38, 266-274; Int. J. Mol, Med., 2010, 26, 813-818; Mol. Metabolism, 2014, 3, 94-108). However, the accumulation of AGE associated with the oxidative imbalance induced by the overproduction of reactive oxygen species (ROS) and the weakening of the antioxidant cellular defence systems found in diabetics, will also be at the origin of the exacerbation of the lipid peroxidation (Chem. Biol. Interact., 2008, 171, 251-271). This oxidative cascade will therefore generate in parallel the formation of ALE such as the complex between the apolipoprotein B of the LDL (Low Density Lipoproteins) natives and the MDA involved in the genesis of the oxidised LDLs. The latter will then be absorbed by macrophages which once loaded with lipidic droplets, will be transformed into foamy cells, constituents of atheromatous plaque (Int. J. Mol, Med., 2010, 26, 813-818).

In the same way, following the exacerbation of the oxidative stress and of the lipid peroxidation, substantial quantities of ALE associated with neuronal proteins are found among patients suffering from neurodegenerative diseases such as for example Alzheimer's disease and Parkinson's disease. As such, in the case of Alzheimer's disease, the physiopathological model of the β-amyloid cascade would tend to prove that the accumulation of β-amyloid plaques that constitute one of the predominant markers of the disease, would be at the origin of a harmful oxidative cascade (Trends Mol. Med. 2001, 7, 548-554; Free Radic. Biol. Med., 2002, 32, 1050-1060). Indeed, under the influence of various genetic and environmental factors, the cleavage by β-secretase of the amyloid precursor protein (APP) becomes preferential to the detriment of the degradation pathway involving α-secretase. Non-toxic Aβ monomers are then formed which, after aggregation induced by the metal ions, are transformed into toxic oligomers, constituents of the β-amyloid plaques at the origin of an exacerbation of the oxidative stress (Chem. Eur. J., 2012, 18, 15910-15920; Neurochem. Int., 2013, 62, 367-378). In the end, the neurotoxicity of the α,β-unsaturated aldehydes then coming from the lipid peroxidation, will largely be involved in the occurrence of the dementia (Curr. Alzheimer Res., 2011, 8, 452-469). Among the latter, mention can be made of acrolein which appears to be the most reactive compound with regards to cysteine, histidine and lysine residues of proteins or 4-HNE. The acrolein will as such result in the formation of ALE at the origin of an alteration of the cytoskeleton and of the appearance of neurofibrillary tangles, another important marker of Alzheimer's disease. Then, the 4-HNE will induce a destabilisation on the neuronal membrane in particular after the formation of ALE on the ion channels and finally a calcium imbalance at the origin of the apoptosis. In addition, ALEs coming from the condensation of the MDA on lysine residues of proteins were able to be identified in the form of dihydropyridine derivatives and would participate in the decrease in the resistance of the skin to UVs which would contribute to the ageing of the skin and possibly to the development of cancers of the skin (Mech. Ageing Dev., 2001, 122, 735-755). Finally, the MDA can also behave as a mutagenic agent after reaction on the amine functions of the bases of the DNA and in particular deoxyguanosine and as such favour the development of certain cancers (Toxicology, 2002, 181-182, 219-222). However, it can be noted that this type of modification of the DNA has also been described in literature in the form of adducts with the MGO (Chem. Res. Toxicol., 2005, 18, 1586-1592).

Several anti-AGE/ALE agents have been described previously in literature. Aminoguanidine (Pimagedine®) has as such shown to be an excellent MGO scavenger in vitro and in vivo on animal models of diabetes (Arch. Biochem. Biophys., 2003, 419, 31-40; Diabetes, 2012, 61, 549-559). However, phase III clinical trials in humans did not provide conclusive results showing weak vasoprotective antioxidant properties and hepatic and gastro-intestinal side effects (Am. J. Nephrol., 2004, 4, 32-40). The trials on this molecule were as such abandoned.

Several other compounds have however shown in vitro and in vivo their effectiveness in slowing down the formation of AGEs and ALEs. Nagai et al. (Bioorg. Med. Chem. 2009, 17, 2310-2320) report for example the anti-AGE properties of pyridoxamine (Pyridorin®), of 2,3-diaminophenazine, of thiamine, of benfotiamine, of TM-2002, of tenilsetam and of LR-9, 20, 59, 74 and 90 as well as the fact that PTB ("Phenacyl Thiazolium Bromide") and ALT-711 have shown to be able to destroy the AGEs and the ALEs. AntiAGE effects have also been described for carnosine (Neurosci. Lett., 1997, 238, 135-13) and OPB-9195 (J. Am. Soc. Nephrol., 2000, 11, 1719-1725). Note that the first clinical trials on OPB-9195 did not provide conclusive results and had to be suspended due to the occurrence of major side effects (Pathologie, Biologie, 2006, 54, 405-419). Most of the studies on the other molecules are still at the experimental stage, except for ALT-711 for which the clinical trials have also been suspended.

Patent applications WO 2006/103274 A1 and WO 2013/050721 A1 describe derivatives of 2,3-diaminopropionic acid previously synthesised by Sasaki et al. as well as the anti-AGE/ALE properties thereof.

It is important to note that this various work has primarily focused on the development of anti-AGE agents. Indeed, few studies concerning the development of potential anti-ALE agents have until now been conducted. The designing of multipotent compounds that are both anti-AGE/ALE and metal chelators has not yet to date been described.

There is as such still a need for novel compounds that have anti-AGE/ALE properties and which are preferably also metal chelators.

SUMMARY OF THE INVENTION

The inventors have now succeeded in developing novel diamine derivatives scavengers of alpha-oxoaldehydes (a-oxoaldehydes) and alpha aldehydes, beta-unsaturated ($\alpha,\beta$-unsaturated aldehydes) and metal chelators. These multipotent compounds have the advantage of combining the scavenger properties of carbonyl compounds with metal chelating properties and antiradical properties.

The invention therefore relates to compounds of Formula I, the pharmaceutically acceptable salts thereof as well as the use of these compounds or the pharmaceutically acceptable salts thereof in pharmaceutical, agrofood or cosmetic compositions.

In a first aspect, the invention relates to compounds of Formula I:

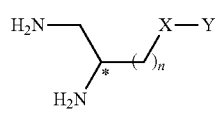

I and the salts thereof, in particular pharmaceutically acceptable, wherein n is an integer from 1 to 6;

X is CO or $CH_2$;

Y is $NR^1R^2$ or $R^2$ or

$R^1$ is H or alkyl or alkyl-aryl;
$R^2$ is $Z$-L-$R^3$;
Z is non-existent, CO or $CH_2$;
L is non-existent, CH=CH or $(CH_2)_m$;
m is an integer from 1 to 6;
$R^3$ is phenyl, substituted by at least one OH group and one or more substituents selected from OH, C1 to C4 alkoxy and C1 to C4 alkyl, or $R^3$ is N-pyridinonyl, substituted by at least one OH group and possibly by one or more substituents selected from OH, C1 to C4 alkoxy and C1 to C4 alkyl.

The compounds of Formula I comprising one asymmetrical carbon atom, they exist in the form of two enantiomers. These enantiomers as well as the mixtures thereof, including the racemic mixtures, are part of the invention.

In another aspect, the invention relates to pharmaceutical, cosmetic or agrofood compositions comprising at least one compound according to the invention or one of the salts thereof, in particular pharmaceutically acceptable and at least one excipient that is acceptable from a pharmaceutical, cosmetic and/or agrofood standpoint.

As indicated hereinabove, the compounds of the invention as well as the pharmaceutically acceptable salts thereof have a particular application in the treatment and/or prevention of diseases or disorders associated with accumulation of AGE (Advanced Glycation Endproducts) and/or of ALE (Advanced Lipid Peroxidation Endproducts).

DETAILED DESCRIPTION OF THE INVENTION

As detailed hereinabove, the invention relates to compounds of Formula I as well as the salts thereof, in particular that are acceptable from a pharmaceutical, cosmetic and/or agrofood standpoint.

Compounds of Formula I and the preferred salts thereof are those wherein one, several or each one of n, Y, $R^1$, $R^2$, Z, L, m and $R^3$ are defined in the following way:

n is an integer from 1 to 4; preferably n is 1, 2 or 3; more preferably n is 2 or 3;

Y is $NR^1R^2$ or $R^2$ or

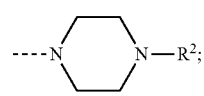

$R^1$ is H, methyl or benzyl; preferably $R^1$ is H or methyl, more preferably $R^1$ is H;
$R^2$ is Z-L-$R^3$;
Z is CO or $CH_2$;
L is absent, CH=CH or $(CH_2)_m$, preferably L is absent, trans-CH=CH or $(CH_2)_m$, m is an integer from 1 to 6; preferably from 1 to 4, more preferably m is 1, 2 or 3;

$R^3$ is phenyl, substituted by at least one OH group and one or more substituents selected from OH, C1 to C4 alkoxy and C1 to C4 alkyl, or $R^3$ is N-pyridinonyl, substituted by at least one OH group and possibly by one or more substituents selected from OH, C1 to C2 alkoxy and C1 to C2 alkyl, preferably selected from OH, methoxy and methyl, more preferably from OH and methoxy or OH and methyl or OH, more preferably $R^3$ is selected from:

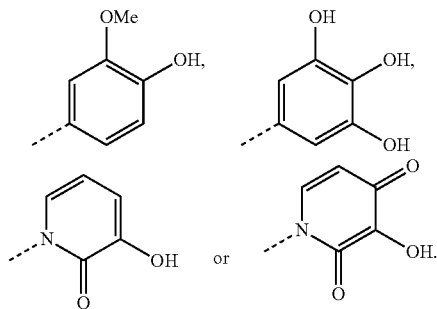

In a particular embodiment, the compounds of Formula I and the salts thereof are those wherein $R^2$ is selected from:

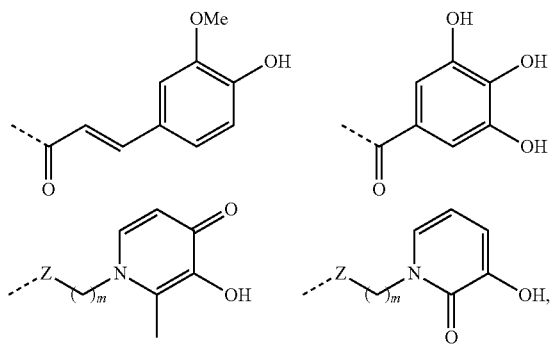

with Z being CO or $CH_2$.

In fact and without wanting to be tied to any theory whatsoever, the inventors think that the ability to form adducts with the MGO and the MDA and the copper chelating power of the compounds according to the invention are obtained at the level of the diamine group. In parallel, the iron chelating power and the antiradical properties of the compounds according to the invention are obtained thanks to the groups derived from ferulic acid (4-hydroxy-3-methoxyphenyl), from gallic acid (3,4,5-trihydroxybenzoyl) and from hydroxypyridinones.

In a first embodiment, the compounds of the invention are those of Formula II:

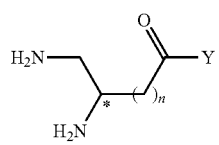

and the salts thereof, in particular pharmaceutically acceptable, wherein n and Y are such as defined hereinabove with respect to Formula I.

In a second embodiment, the compounds of the invention are those of Formula III

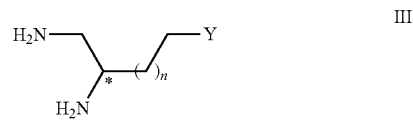

and the salts thereof, in particular pharmaceutically acceptable, wherein n and Y are such as defined hereinabove with respect to Formula I.

In a third embodiment, the compounds of the invention are those of Formula IV

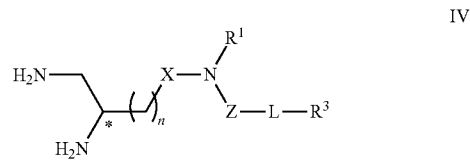

and the salts thereof, in particular pharmaceutically acceptable, wherein n, X, $R^1$, Z, L and $R^3$ are such as defined with respect to Formula I.

Preferred compounds of Formula IV are those wherein Z-L-$R^3$ is selected from:

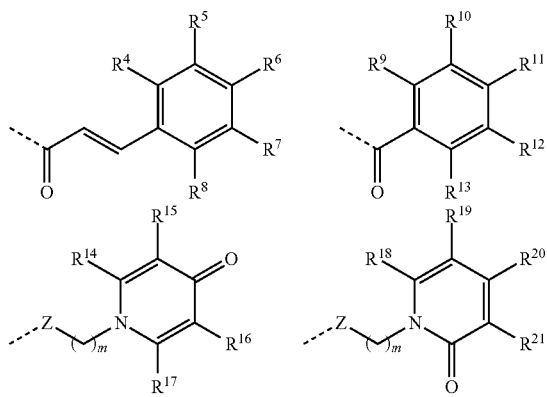

wherein $R^4, R^5, R^6, R^7, R^8, R^9, R^{10}, R^{11}, R^{12}, R^{13}, R^{14}, R^{15}, R^{16}, R^{17}, R^{18}, R^{19}, R^{20}$ and $R^{21}$ are selected, independently of one another, from H, OH, C1 to C4 alkoxy and C1 to C4 alkyl, preferably from H, OH, C1 to C2 alkoxy and C1 to C2 alkyl, preferably from H, OH, methoxy and methyl, more preferably from H, OH and methoxy; H or OH and H, methyl or OH; with the proviso that at least one of $R^4, R^5, R^6, R^7$ and $R^8$, of $R^9, R^{10}, R^{11}, R^{12}$ and $R^{13}$, of $R^{14}, R^{15}, R^{16}$ and $R^{17}$, of $R^{18}, R^{19}, R^{20}$ and $R^{21}$ is OH.

Particularly preferred compounds of Formula IV are those wherein Z-L-$R^3$ is selected from:

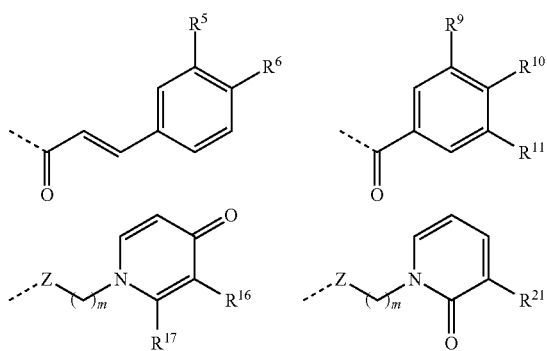

wherein $R^5$, $R^6$, $R^9$, $R^{10}$, $R^{11}$, $R^{16}$, $R^{17}$ and $R^{21}$ are selected, independently of one another, from OH, C1 to C4 alkoxy and C1 to C4 alkyl, preferably from OH, C1 to C2 alkoxy and C1 to C2 alkyl, preferably from OH, methoxy and methyl, more preferably from OH and methoxy or OH and methyl or OH; with the proviso that at least one of $R^5$ and $R^6$, of $R^9$, $R^{10}$ and $R^{11}$, of $R^{16}$ and $R^{17}$ and of $R^{21}$ is OH. Particularly advantageous compounds of Formula IV are those wherein

- $R^5$ and $R^6$ are selected, independently of one another, from OH and C1 to C4 alkoxy, preferably from OH and C1 to C2 alkoxy, more preferably from OH and methoxy; advantageously $R^5$ is C1 to C4 alkoxy, preferably C1 to C2 alkoxy, more preferably methoxy and $R^6$ is OH;
- $R^9$, $R^{10}$ and $R^{11}$ are OH;
- $R^{16}$ and $R^{17}$ are selected, independently of one another, from OH and C1 to C4 alkyl, preferably from OH and C1 to C2 alkyl, more preferably from OH and methyl; advantageously $R^{16}$ is OH and $R^{17}$ is C1 to C4 alkyl, preferably C1 to C2 alkyl, more preferably methyl;
- $R^{21}$ is OH.

In an embodiment, the compounds of Formula IV are those wherein Z-L-$R^3$ is selected from:

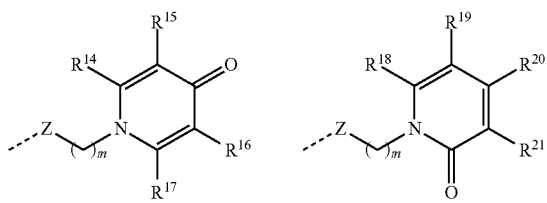

$R^{14}$, $R^{15}$, $R^{16}$, $R^{18}$, $R^{19}$, $R^{20}$ and $R^{21}$ are selected, independently of one another, from H, OH and C1 to C4 alkyl, preferably from H, OH and C1 to C2 alkyl, preferably from H, OH and methyl; with the proviso that at least one of $R^{14}$, $R^{15}$, $R^{16}$ and $R^{17}$ and of $R^{18}$, $R^{19}$, $R^{20}$ and $R^{21}$ is OH. Advantageously Z-L-$R^3$ is selected from:

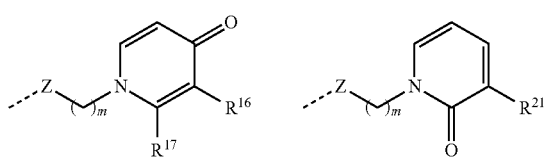

wherein $R^{16}$, $R^{17}$ and $R^{21}$ are selected, independently of one another, from OH and C1 to C4 alkyl, preferably from OH and C1 to C2 alkyl, more preferably from OH and methyl; with the proviso that at least one of $R^{16}$ and $R^{17}$ and of $R^{21}$ is OH. Particularly advantageous compounds are those wherein

- $R^{16}$ and $R^{17}$ are selected, independently of one another, from OH and C1 to C4 alkyl, preferably from OH and C1 to C2 alkyl, more preferably from OH and methyl; advantageously $R^{16}$ is OH and $R^{17}$ is C1 to C4 alkyl, preferably C1 to C2 alkyl, more preferably methyl;
- $R^{21}$ is OH.

In a fourth embodiment, the compounds of the invention are those of Formula V

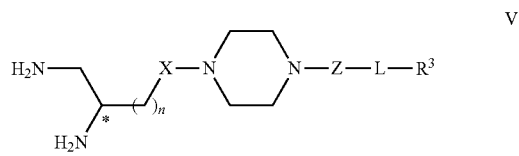

and the salts thereof, in particular pharmaceutically acceptable, wherein n, X, Z, L and $R^3$ are such as defined with respect to Formula I.

Preferred compounds of Formula V are those wherein Z-L-$R^3$ is selected from:

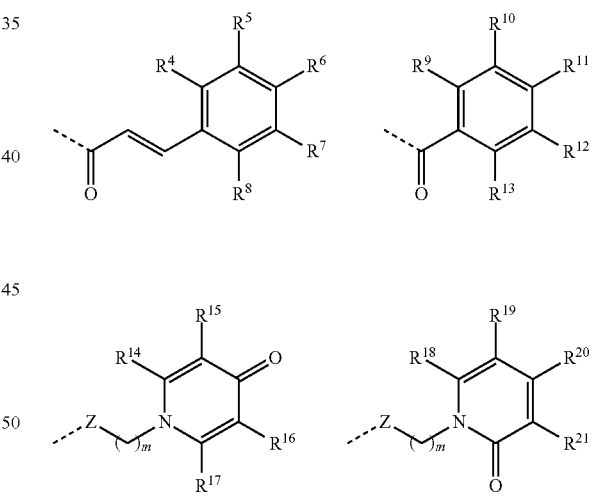

wherein $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ and $R^{21}$ are selected, independently of one another, from H, OH, C1 to C4 alkoxy and C1 to C4 alkyl, preferably from H, OH, C1 to C2 alkoxy and C1 to C2 alkyl, preferably from H, OH, methoxy and methyl, more preferably from H, OH and methoxy; H or OH and H, methyl or OH; with the proviso that at least one of $R^4$, $R^5$, $R^6$, $R^7$ and $R^8$, at least one of $R^9$, $R^{10}$, $R^{11}$, $R^{12}$ and $R^{13}$, at least one of $R^{14}$, $R^{15}$, $R^{16}$ and $R^{17}$, and at least one of $R^{18}$, $R^{19}$, $R^{20}$ and $R^{21}$ is OH.

Particularly preferred compounds of Formula V are those wherein Z-L-$R^3$ is selected from:

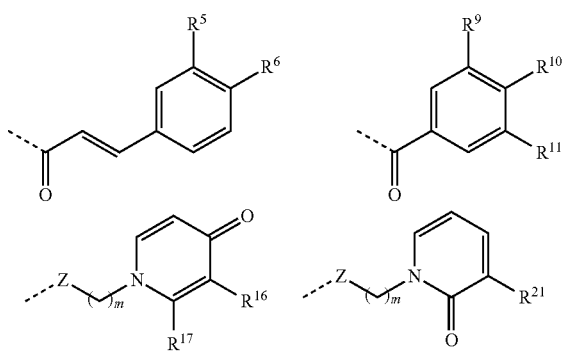

$R^5$, $R^6$, $R^9$, $R^{10}$, $R^{11}$, $R^{16}$, $R^{17}$ and $R^{21}$ wherein are selected, independently of one another, from OH, C1 to C4 alkoxy and C1 to C4 alkyl, preferably from OH, C1 to C2 alkoxy and C1 to C2 alkyl, preferably from OH, methoxy and methyl, more preferably from OH and methoxy or OH and methyl or OH; with the proviso that at least one of $R^5$ and $R^6$, at least one of $R^9$, $R^{10}$ and $R^{11}$, at least one of $R^{16}$ and $R^{17}$ is OH and $R^{21}$ is OH. Particularly advantageous compounds of Formula IV are those wherein
- $R^5$ and $R^6$ are selected, independently of one another, from OH and C1 to C4 alkoxy, preferably from OH and C1 to C2 alkoxy, more preferably from OH and methoxy; advantageously $R^5$ is C1 to C4 alkoxy, preferably C1 to C2 alkoxy, more preferably methoxy and $R^6$ is OH;
- $R^9$, $R^{10}$ and $R^{11}$ are OH;
- $R^{16}$ and $R^{17}$ are selected, independently of one another, from OH and C1 to C4 alkyl, preferably from OH and C1 to C2 alkyl, more preferably from OH and methyl; advantageously $R^{16}$ is OH and $R^{17}$ is C1 to C4 alkyl, preferably C1 to C2 alkyl, more preferably methyl;
- $R^{21}$ is OH.

In an embodiment, the compounds of Formula V are those wherein Z-L-$R^3$ is selected from:

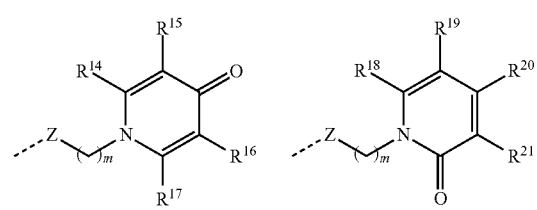

wherein $R^{14}$, $R^{15}$, $R^{16}$, $R^{17}$, $R^{18}$, $R^{19}$, $R^{20}$ and $R^{21}$ are selected, independently of one another, from H, OH and C1 to C4 alkyl, preferably from H, OH and C1 to C2 alkyl, preferably from H, OH and methyl; with the proviso that at least one of $R^{14}$, $R^{15}$, $R^{16}$ and $R^{17}$ and at least one of $R^{18}$, $R^{19}$, $R^{20}$ and $R^{21}$ is OH. Advantageously Z-L-$R^3$ is selected from:

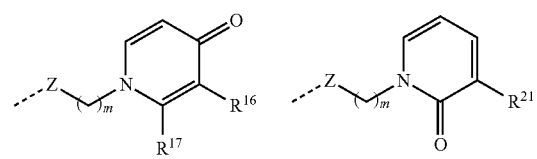

wherein $R^{16}$, $R^{17}$ and $R^{21}$ are selected, independently of one another, from OH and C1 to C4 alkyl, preferably from OH and C1 to C2 alkyl, more preferably from OH and methyl; with the proviso that at least one of $R^{16}$ and $R^{17}$ is OH and $R^{21}$ is OH. Particularly advantageous compounds are those wherein
- $R^{16}$ and $R^{17}$ are selected, independently of one another, from OH and C1 to C4 alkyl, preferably from OH and C1 to C2 alkyl, more preferably from OH and methyl; advantageously $R^{16}$ is OH and $R^{17}$ is C1 to C4 alkyl, preferably C1 to C2 alkyl, more preferably methyl;
- $R^{21}$ is OH.

In a fifth embodiment, the compounds of the invention are those of Formula VI

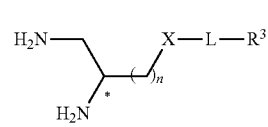

and the salts thereof, in particular pharmaceutically acceptable,
wherein n, X, L and $R^3$ are such as defined with respect to Formula I.

Preferred compounds of Formula VI are those wherein n is 1 or 2, X is $CH_2$ and/or L-$R^3$ is

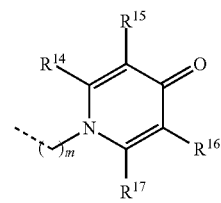

wherein $R^{14}$, $R^{15}$, $R^{16}$ and $R^{17}$ are selected, independently of one another, from H, OH and C1 to C4 alkyl, preferably from H, OH and C1 to C2 alkyl, preferably from H, OH and methyl; with the proviso that at least one of $R^{14}$, $R^{15}$, $R^{16}$ and $R^{17}$ is OH. Advantageously L-$R^3$ is selected from:

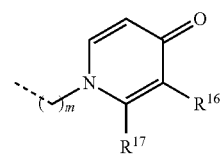

wherein $R^{16}$ and $R^{17}$ are selected, independently of one another, from OH and C1 to C4 alkyl, preferably from OH and C1 to C2 alkyl, more preferably from OH and methyl; with the proviso that at least one of $R^{16}$ and $R^{17}$ is OH. Particularly advantageous compounds are those wherein $R^{16}$ is OH and $R^{17}$ is C1 to C4 alkyl, preferably C1 to C2 alkyl, more preferably methyl.

Particularly preferred compounds of the invention are those listed in Table 1 hereinbelow:

TABLE 1

| Structure | Name |
|---|---|
| 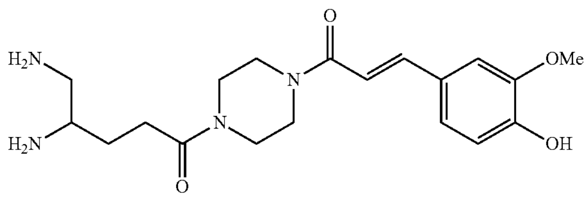 [SMILES: COc1cc(/C=C/C(=O)N2CCN(C(=O)CCC(N)CN)CC2)ccc1O] | (E)-4,5-diamino-1-(4-(3-(4-hydroxy-3-methoxyphenyl)acryloyl)piperazin-1-yl)pentan-1-one |
| 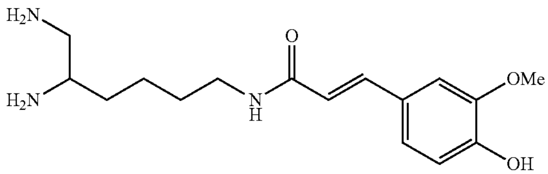 [SMILES: COc1cc(/C=C/C(=O)NCCCCC(N)CN)ccc1O] | (E)-N-(5,6-diaminohexyl)-3-(4-hydroxy-3-methoxyphenyl)acrylamide |
| 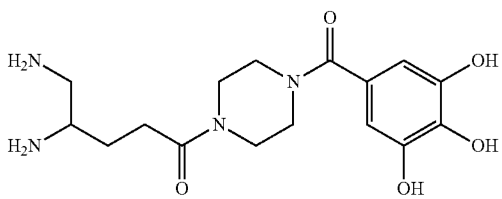 [SMILES: NCC(N)CCC(=O)N1CCN(C(=O)c2cc(O)c(O)c(O)c2)CC1] | 4,5-diamino-1-(4-(3,4,5-trihydroxybenzoyl)piperazin-1-yl)pentan-1-one |
| 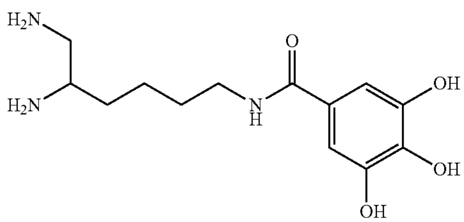 [SMILES: NCC(N)CCCCNC(=O)c1cc(O)c(O)c(O)c1] | N-(5,6-diaminohexyl)-3,4,5-trihydroxybenzamide |
| 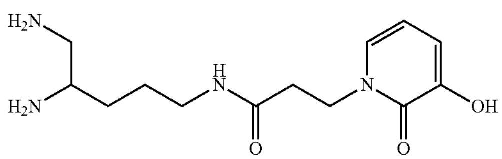 [SMILES: NCC(N)CCCNC(=O)CCn1cccc(O)c1=O] | N-(4,5-diaminopentyl)-3-(3-hydroxy-2-oxopyridin-1(2H)-yl)propanamide |
| 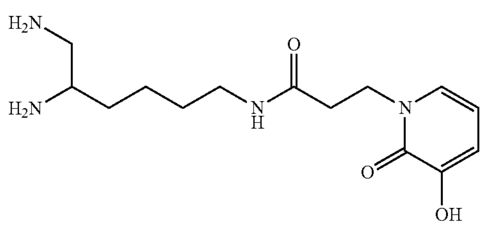 [SMILES: NCC(N)CCCCNC(=O)CCn1cccc(O)c1=O] | N-(5,6-diaminohexyl)-3-(3-hydroxy-2-oxopyridin-1(2H)-yl)propanamide |
| 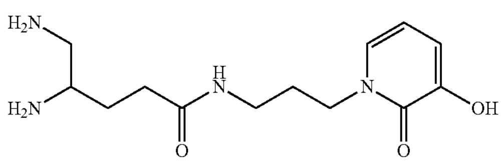 [SMILES: NCC(N)CCC(=O)NCCCn1cccc(O)c1=O] | 4,5-diamino-N-(3-(3-hydroxy-2-oxopyridin-1(2H)-yl)propyl)pentanamide |
| 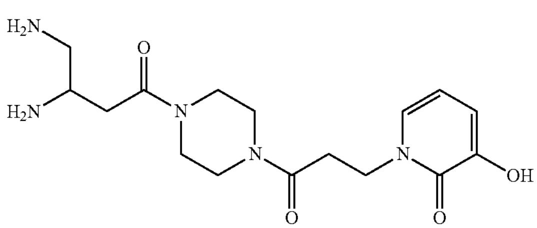 [SMILES: NCC(N)CC(=O)N1CCN(C(=O)CCn2cccc(O)c2=O)CC1] | 1-(3-(4-(3,4-diaminobutanoyl)piperazin-1-yl)-3-oxopropyl)-3-hydroxypyridin-2(1H)-one |

TABLE 1-continued

| Structure | Name |
|---|---|
| 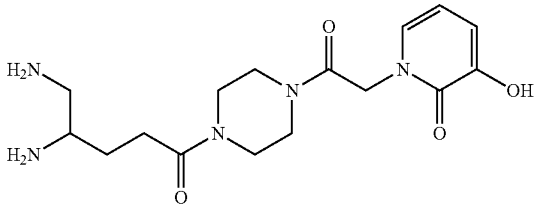 [SMILES: NCC(N)CCC(=O)N1CCN(C(=O)Cn2cccc(O)c2=O)CC1] | 1-(2-(4-(4,5-diaminopentanoyl)piperazin-1-yl)-2-oxoethyl)-3-hydroxypyridin-2(1H)-one |
| 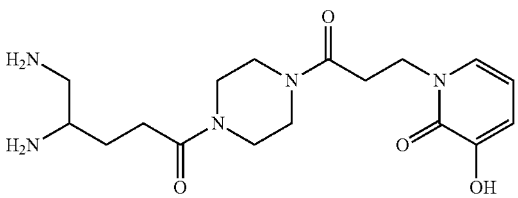 [SMILES: NCC(N)CCC(=O)N1CCN(C(=O)CCn2cccc(O)c2=O)CC1] | 1-(3-(4-(4,5-diaminopentanoyl)piperazin-1-yl)-3-oxopropyl)-3-hydroxypyridin-2(1H)-one |
| 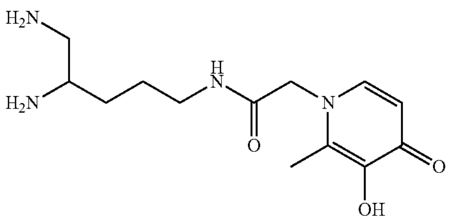 [SMILES: Cc1c(O)c(=O)ccn1CC(=O)NCCCC(N)CN] | N-(4,5-diaminopentyl)-2-(3-hydroxy-2-methyl-4-oxopyridin-1(4H)-yl)acetamide |
| 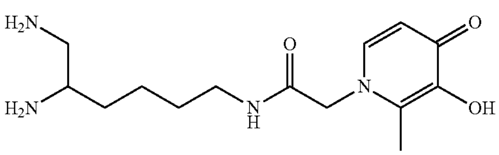 [SMILES: Cc1c(O)c(=O)ccn1CC(=O)NCCCCC(N)CN] | N-(5,6-diaminohexyl)-2-(3-hydroxy-2-methyl-4-oxopyridin-1(4H)-yl)acetamide |
| 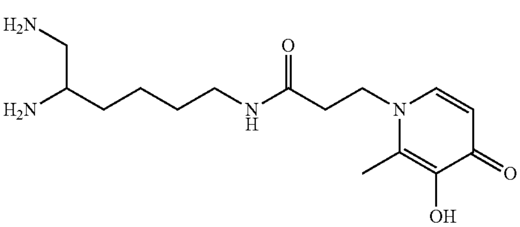 [SMILES: Cc1c(O)c(=O)ccn1CCC(=O)NCCCCC(N)CN] | N-(5,6-diaminohexyl)-3-(3-hydroxy-2-methyl-4-oxopyridin-1(4H)-yl)propanamide |
| 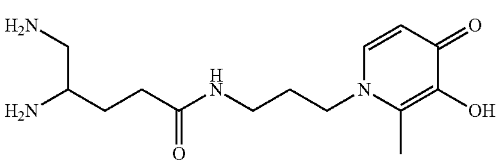 [SMILES: Cc1c(O)c(=O)ccn1CCCNC(=O)CCC(N)CN] | 4,5-diamino-N-(3-(3-hydroxy-2-methyl-4-oxopyridin-1(4H)-yl)propyl)pentanamide |
| 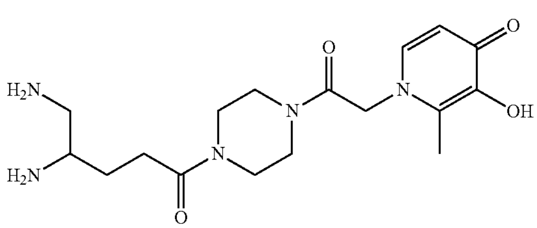 [SMILES: Cc1c(O)c(=O)ccn1CC(=O)N1CCN(C(=O)CCC(N)CN)CC1] | 1-(2-(4-(4,5-diaminopentanoyl)piperazin-1-yl)-2-oxoethyl)-3-hydroxy-2-methylpyridin-4(1H)-one |
| 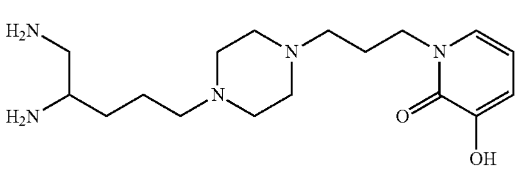 [SMILES: NCC(N)CCCN1CCN(CCCn2cccc(O)c2=O)CC1] | 1-(3-(4-(4,5-diaminopentyl)piperazin-1-yl)propyl)-3-hydroxypyridin-2(1H)-one |

TABLE 1-continued

| Structure | Name |
|---|---|
| [Structure: H2N-CH(CH2NH2)-(CH2)3-N(CH3)-(CH2)3-N-pyridinone with 3-OH, 2-oxo] | 1-(3-((4,5-diaminopentyl)(methyl)amino)propyl)-3-hydroxypyridin-2(1H)-one |
| [Structure: H2N-CH2-CH(NH2)-(CH2)4-N-pyridinone with 2-methyl, 3-OH, 4-oxo] | 1-(5,6-diaminohexyl)-3-hydroxy-2-methylpyridin-4(1H)-one |

The compounds of Formula I can be prepared according to reactions known to those skilled in the art. The reaction schemes described in the "Examples" part show possible synthesis approaches.

Due to their ability to scavenge α-oxoaldehydes and/or α,β-unsaturated aldehydes, the ability thereof to chelate metals and the anti-oxidant properties thereof, the compounds of the invention and the salts thereof, in particular acceptable from a pharmaceutical and/or cosmetic standpoint, have an application in the pharmaceutical and/or cosmetic industry.

In a second aspect, the invention therefore relates to the compounds of the invention for use as a medicament.

More particularly, the compounds of the invention are as such useful in the treatment and/or prevention of diseases or disorders associated with an accumulation of advanced glycation endproducts (AGEs) and/or of advanced lipid peroxidation endproducts (ALEs).

These diseases or disorders include neurodegenerative diseases, micro- and macroangiopathies linked to the oxidative and carbonyl stresses, diabetes-related disorders and age-related pathologies.

In a particular embodiment, the diseases or disorders are selected from neurodegenerative diseases, in particular from Alzheimer's disease and Parkinson's disease.

In another particular embodiment, the diseases or disorders are selected from micro- and macroangiopathies linked to the oxidative and carbonyl stresses of the atherosclerosis type.

In another particular embodiment, the diseases or disorders are selected from diabetes-related disorders, in particular from atherosclerosis, retinopathy, nephropathy, neuropathy, micro and macroangiopathies, cataract, amyloidosis, rheumatic disorders and varicose and arterial ulcers.

In another particular embodiment, the diseases or disorders are selected from age-related pathologies such as for example cataract and rheumatisms.

This invention, according to another of its aspects, also relates to a method for treating diseases and conditions indicated hereinabove comprising the administration, to a patient, of an effective amount of a compound according to the invention, or of one of the pharmaceutically acceptable solvates thereof. Preferably, the patient is a warm-blooded animal, more preferably a human.

The invention also relates to a pharmaceutical composition comprising at least one compound of the invention or at least one pharmaceutically acceptable salt of said compound and a pharmaceutically acceptable excipient. Said excipients are selected according to the pharmaceutical form and the mode of administration desired, from the usual excipients which are known to those skilled in the art.

The pharmaceutical composition of this invention can be selected from the pharmaceutical compositions for administration by oral, sublingual, subcutaneous, intramuscular, intravenous, topical, local, intratracheal, intranasal, transdermal or rectal route. In these compositions, the active ingredient of Formula I hereinabove, or the pharmaceutically acceptable solvate thereof, can be administered in unit administration form, as a mixture with conventional pharmaceutical excipients, to animals and to human beings for the treatment and/or the prevention of the diseases or disorders indicated hereinabove. The suitable unit administration forms include the forms by oral route such as tablets, soft and hard capsules, powders, granules and oral solutions or suspensions, sublingual, buccal, intratracheal, intraocular, intranasal administration forms, via inhalation, topical, transdermal, subcutaneous, intramuscular or intravenous administration forms, rectal administration forms and implants. For topical application, the compounds according to the invention can be used in creams, gels, ointments or lotions. In a preferred embodiment, this is a pharmaceutical composition for oral administration. Such suitable administration forms which can have the form of a solid, semi-solid or liquid according to the mode of administration, are generally known to those skilled in the art, with reference being made to the latest edition of the work "Remington's Pharmaceutical Sciences".

As the accumulation of AGEs is generally linked to malfunctions that have a cosmetic impact, such as the loss of elasticity of the skin tissue or of the vascular endothelium and the pigmentation of the skin (Dermatoendocrinol. 2012, 4, 259-270), the compounds of the invention are useful as an active ingredient in cosmetic compositions.

DEFINITIONS

The definitions and explanations hereinbelow relate to the terms and expressions as used in this application, comprising the description as well as the claims.

For the description of the compounds of the invention, the terms and expressions used must, unless mentioned otherwise, be interpreted according to the definitions hereinafter.

The term "alkyl(e)", alone or as part of another group, refers to a hydrocarbon radical of formula $C_nH_{2n+1}$ wherein n is an integer greater than or equal to 1.

The term "salt" refers to the acid addition salts of compounds of Formula I. It encompasses the salts with inorganic and organic acids, such as hydrochloric acid, nitric acid, sulphuric acid, phosphoric acid, citric acid, formic acid, fumaric acid, maleic acid, acetic acid, succinic acid, tartaric acid, methanesulphonic acid, p-toluenesulphonic acid, oxalic acid and similar.

All of the references to compounds of Formula I also designate the salts of the latter.

The term "patient" refers to a warm-blooded animal, preferably a human, who is awaiting or receiving a medical treatment.

The term "human" refers to subjects of both genders and at any stage of development (i.e. neonatal, infantile, juvenile, adolescent and adult). In an embodiment, this is an adolescent or an adult, preferably an adult.

The terms "treat" and "treatment" must be understood in their general meaning and include as such the improvement and the abrogation of a pathological condition.

The terms "prevent" and "prevention" refer to the avoiding or the delaying of the appearance of a disease or condition and of the related symptoms, as such excluding a patient from developing a disease or condition or reducing the risk that a patient develops a disease or condition.

The term "therapeutically effective amount" or "effective amount" refers to the amount of active ingredient (compound of Formula I) that is sufficient to achieve the desired therapeutic or prophylactic result in the patient to which it is administered.

The term "pharmaceutically acceptable" or "acceptable from a pharmaceutical standpoint" means that a compound or a component is not harmful for the patient and that in the framework of a pharmaceutical composition it is compatible with the other components.

The term "cosmetically acceptable" means that a compound or a component is not harmful for the user, in particular a human, and that in the framework of a cosmetic composition it is compatible with the other components.

The term "acceptable from an agrofood standpoint" means that a compound or a component is not harmful for a warm-blooded animal, in particular for a human during the ingestion thereof and that in the framework of an agrofood composition it is compatible with the other components.

This invention shall be understood better with reference to the following examples. These examples represent certain embodiments of the invention and do not in any way limit the scope of the invention. The figures are used to illustrate the experimental results.

FIGURES

FIG. 1: Structure of the various compounds studied

Figure 2:
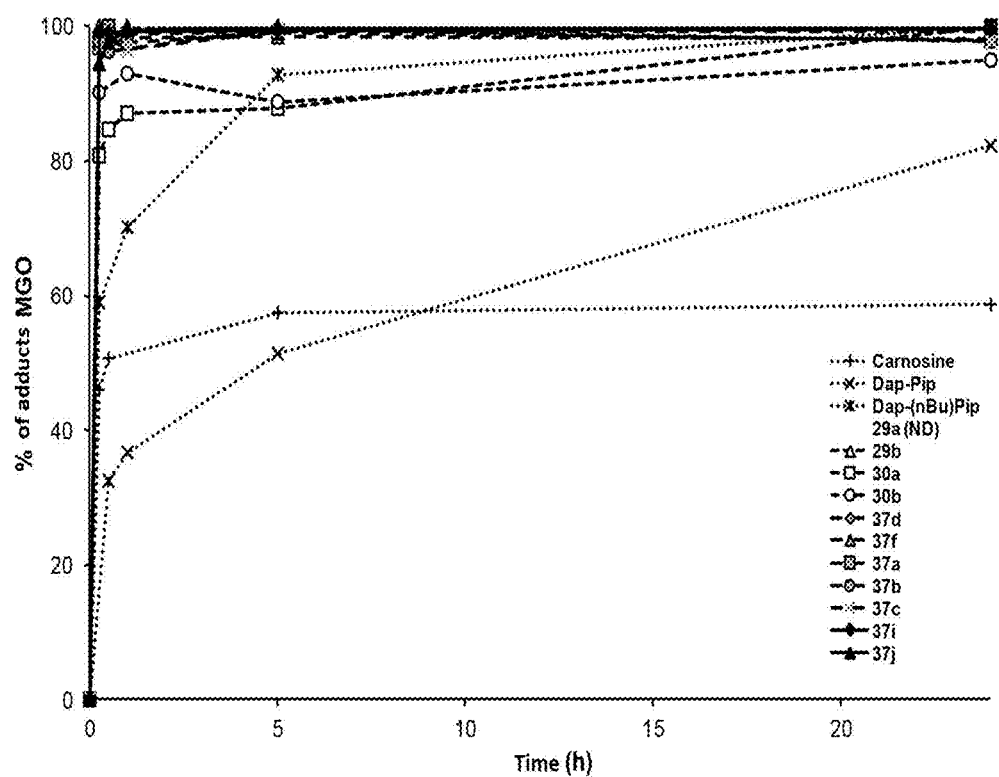

FIG. 2: Kinetic study of the formation of adducts between the MGO and the compounds according to the invention FIG. 3: Mass spectrum providing evidence of the formation of at least three types of adducts between the MGO and the compound 37a after 15 min of incubation at 37° C.

Figure 4:
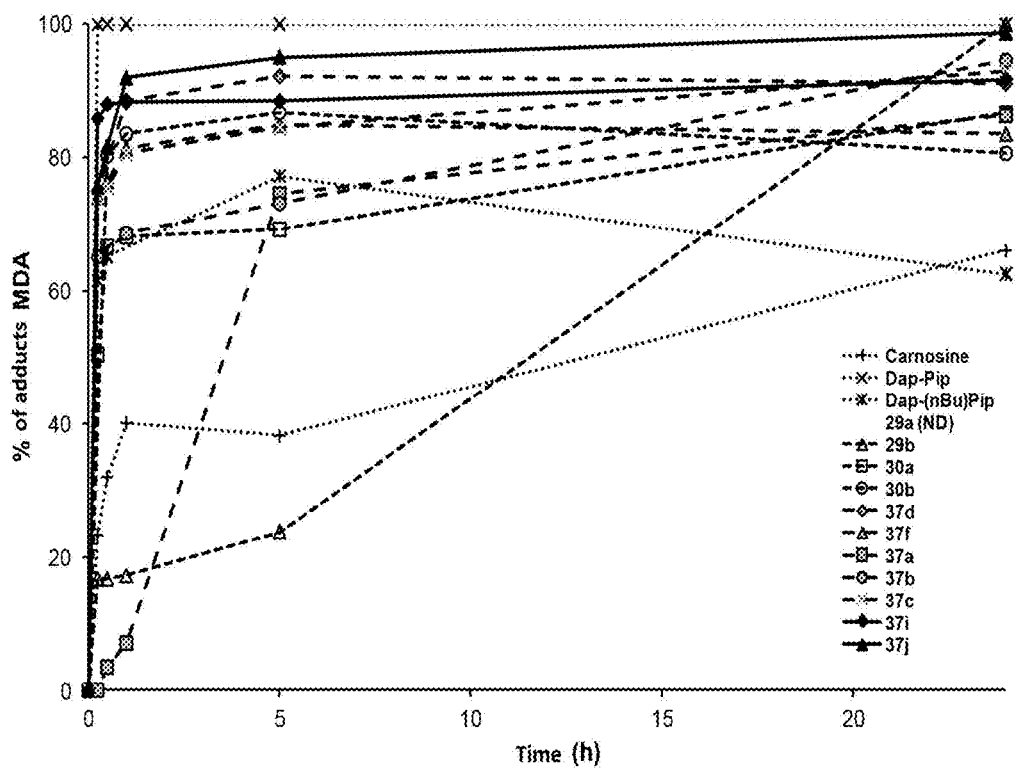

FIG. 4: Kinetic study of the formation of adducts between the MDA and the compounds according to the invention FIG. 5: Mass spectrum providing evidence of the formation of at least one adduct between the MDA and the compound 37a after 5 h of incubation at 37° C.

Figure 6:
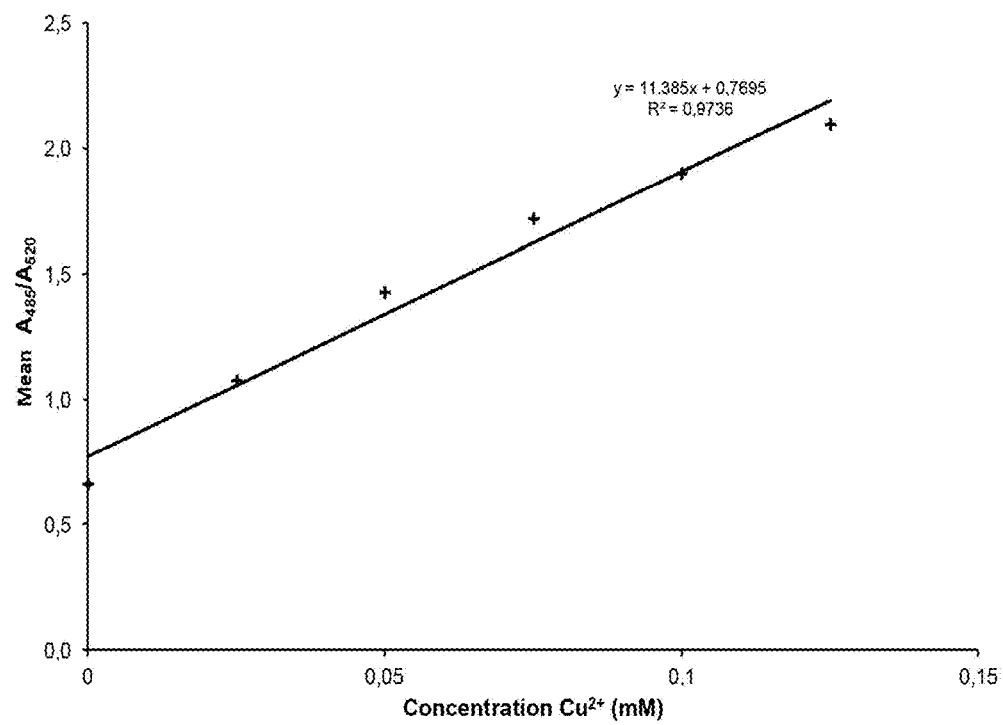

FIG. 6: Calibration curve carried out in Hexamine buffer 0.01 M/KCl 0.01 M (pH=5)

Figure 7:
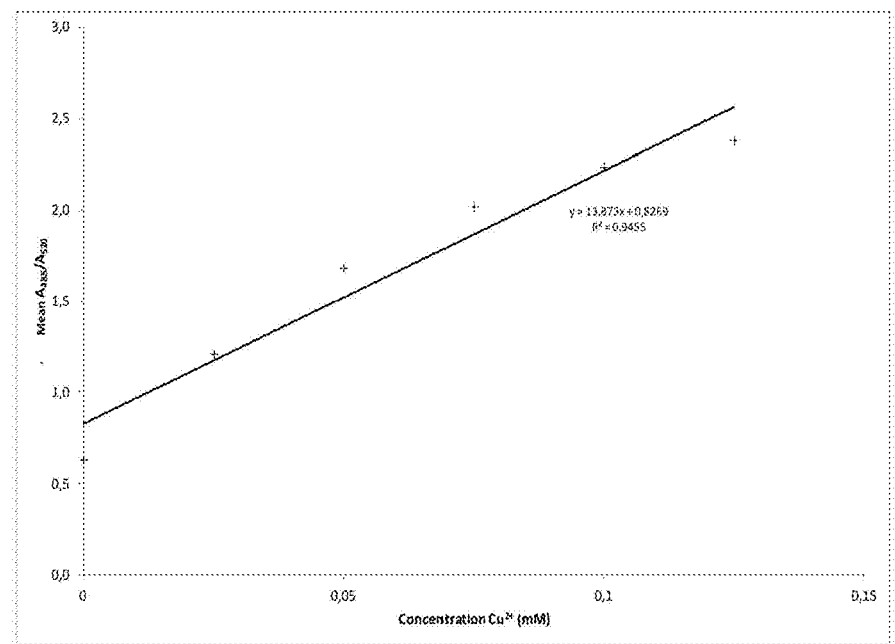

FIG. 7: Calibration curve carried out in a mixture of Hexamine buffer 0.01 M/KCl 0.01 M (pH=5) and of MeOH 75/25

Figure 8:
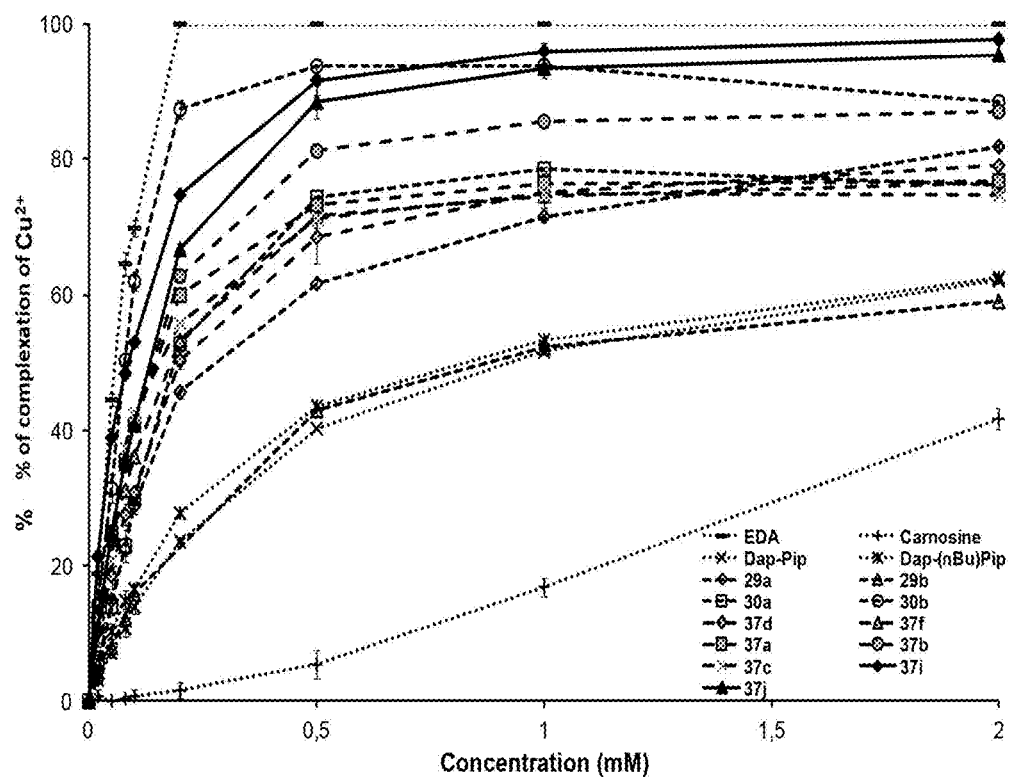

FIG. 8: Comparison of the complexation % of the $Cu^{2+}$ of different compounds according to the invention according to their concentration FIG. 9: Two compounds related to compound 37b tested for the $Cu^{2+}$ chelating properties thereof FIG. 10: Comparison of the complexation % of the $Cu^{2+}$ of the compound 37b and of two related compounds having only one free $Cu^{2+}$ chelating end according to their concentration FIG. 11: Calibration curve of trolox (Net AUC vs concentration). The values shown are expressed by the mean±SEM of triplicates constituting a representative experiment from the three independent experiments conducted.

Figure 12:
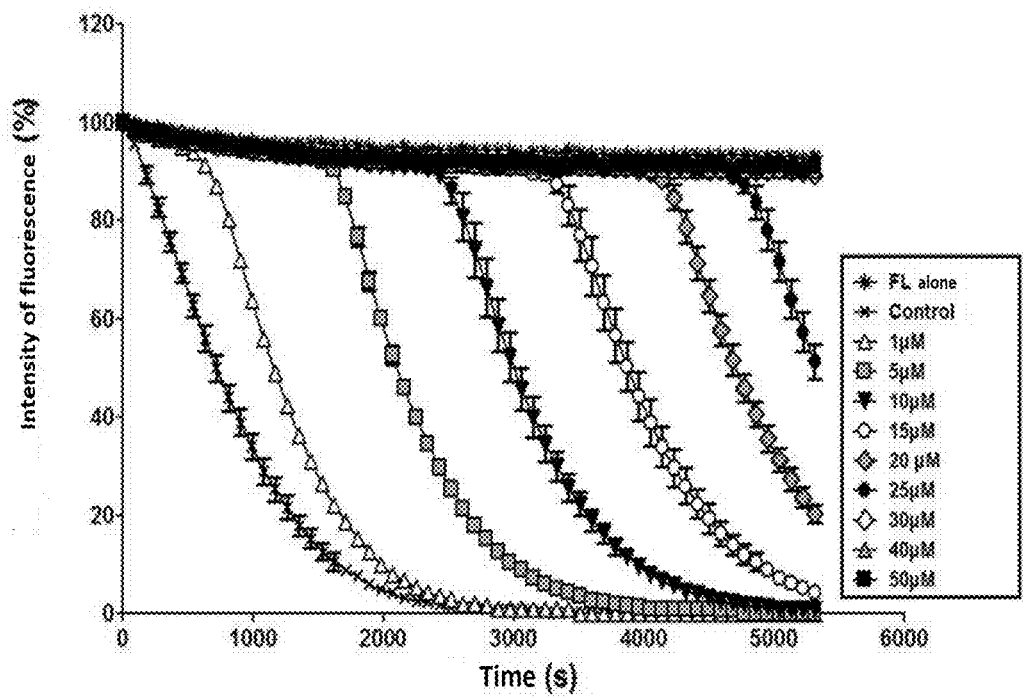

FIG. 12: Decay curve of the fluorescence of the fluorescein induced by the AAPH. The values shown concern the results obtained in the absence (control) or in the presence of trolox at different concentrations and are expressed by the mean±SEM of triplicates constituting a representative experiment from the three independent experiments conducted.

Figure 13:
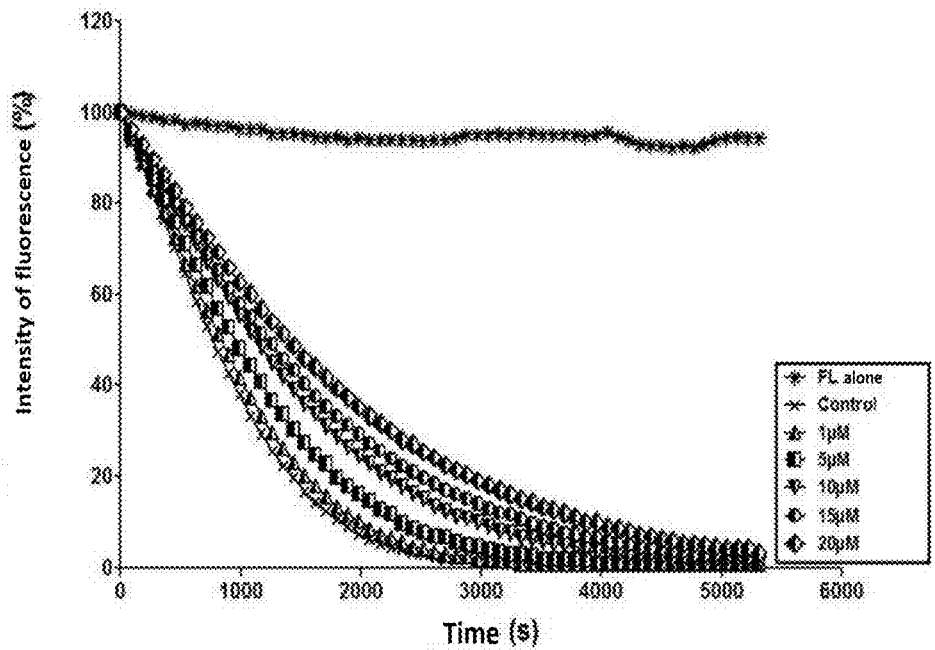

FIG. 13: Decay curve of the fluorescence of the fluorescein induced by the AAPH. The values shown concern the results obtained in the absence (control) or in the presence of carnosine at different concentrations and are expressed by the mean±SEM of triplicates constituting a representative experiment from the three independent experiments conducted.

Figure 14:
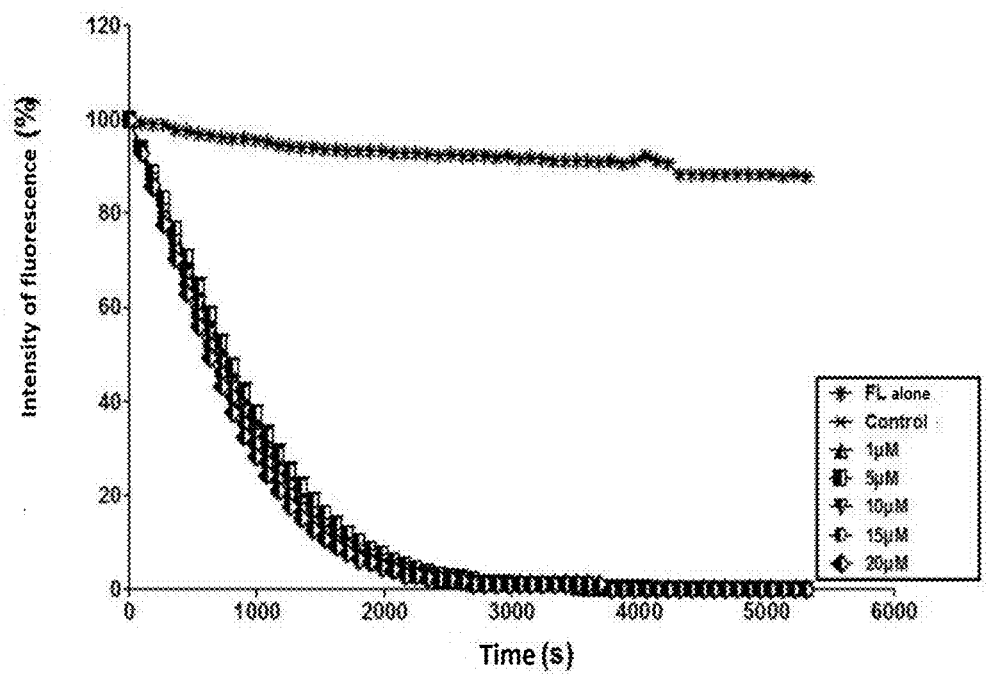

FIG. 14: Decay curve of the fluorescence of the fluorescein induced by the AAPH. The values shown concern the results obtained in the absence (control) or in the presence of Dap-Pip at different concentrations and are expressed by the mean±SEM of triplicates constituting a representative experiment from the three independent experiments conducted.

Figure 15:
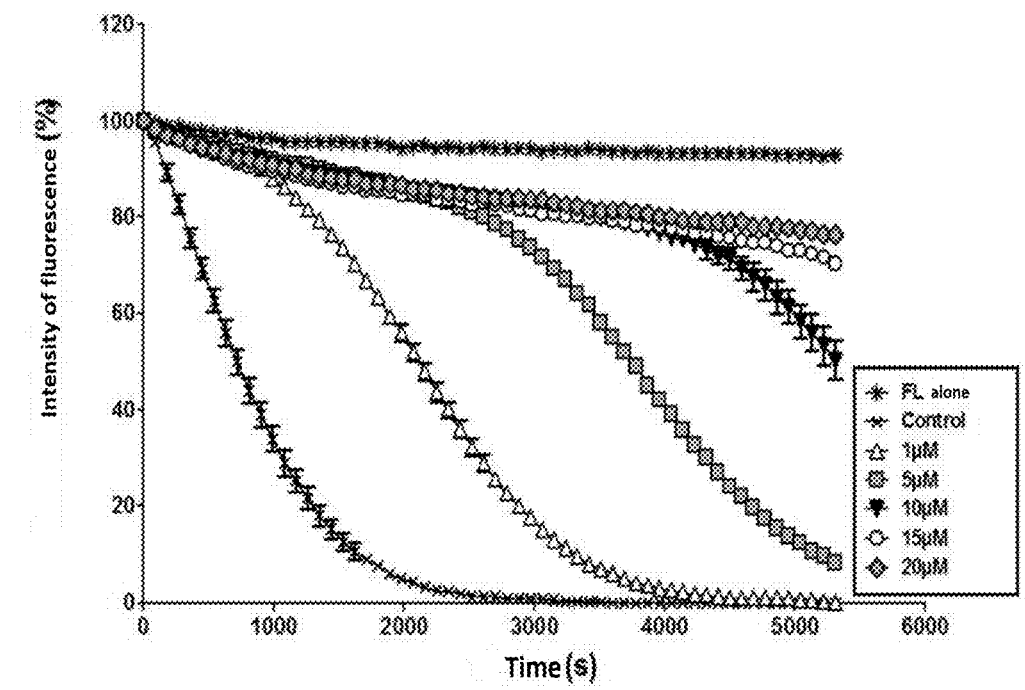

FIG. 15: Decay curve of the fluorescence of the fluorescein induced by the AAPH. The values shown concern the results obtained in the absence (control) or in the presence of the compound 29a at different concentrations and are expressed by the mean±SEM of triplicates constituting a representative experiment from the three independent experiments conducted.

Figure 16:
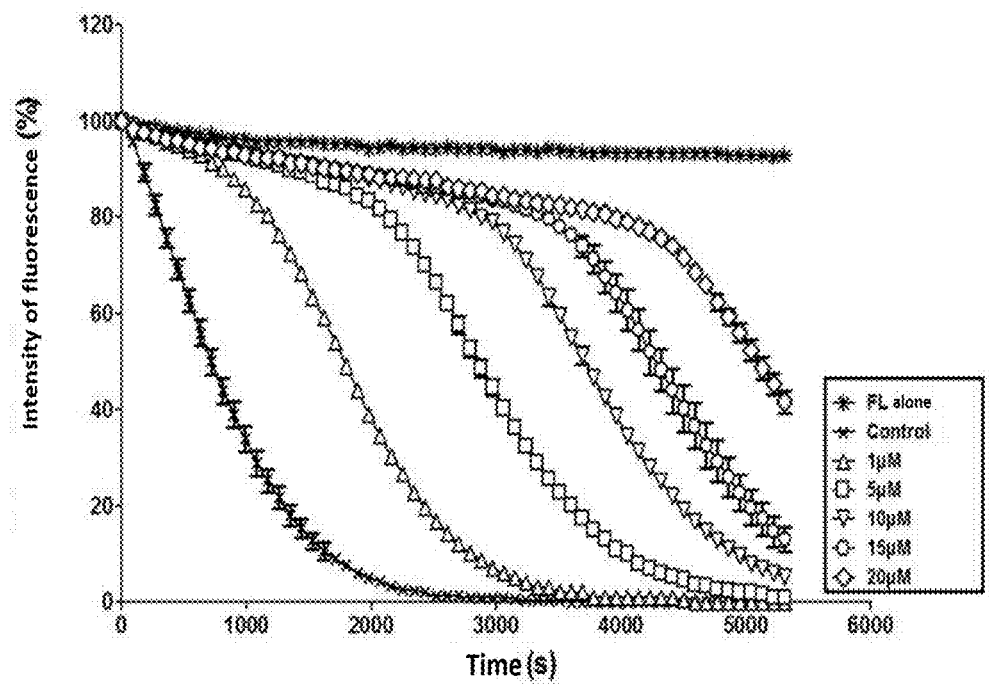

FIG. 16: Decay curve of the fluorescence of the fluorescein induced by the AAPH. The values shown concern the results obtained in the absence (control) or in the presence of the compound 29b at different concentrations and are expressed by the mean±SEM of triplicates constituting a representative experiment from the three independent experiments conducted.

Figure 17:
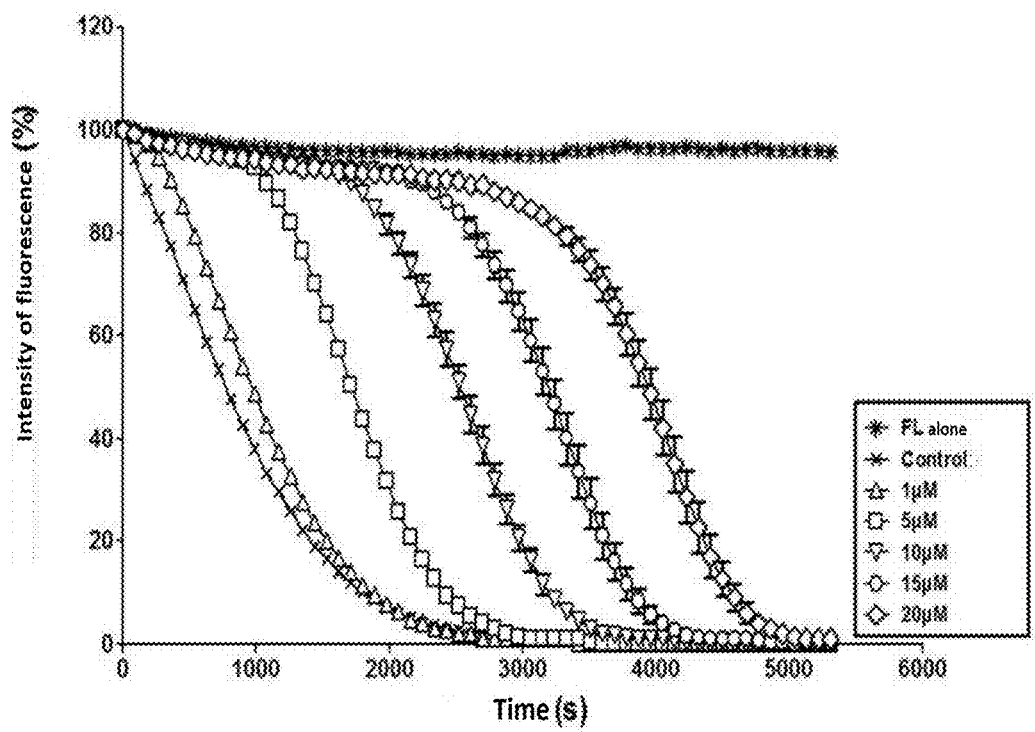

FIG. 17: Decay curve of the fluorescence of the fluorescein induced by the AAPH. The values shown concern the results obtained in the absence (control) or in the presence of the compound 30a at different concentrations and are expressed by the mean±SEM of triplicates constituting a representative experiment from the three independent experiments conducted.

Figure 18:
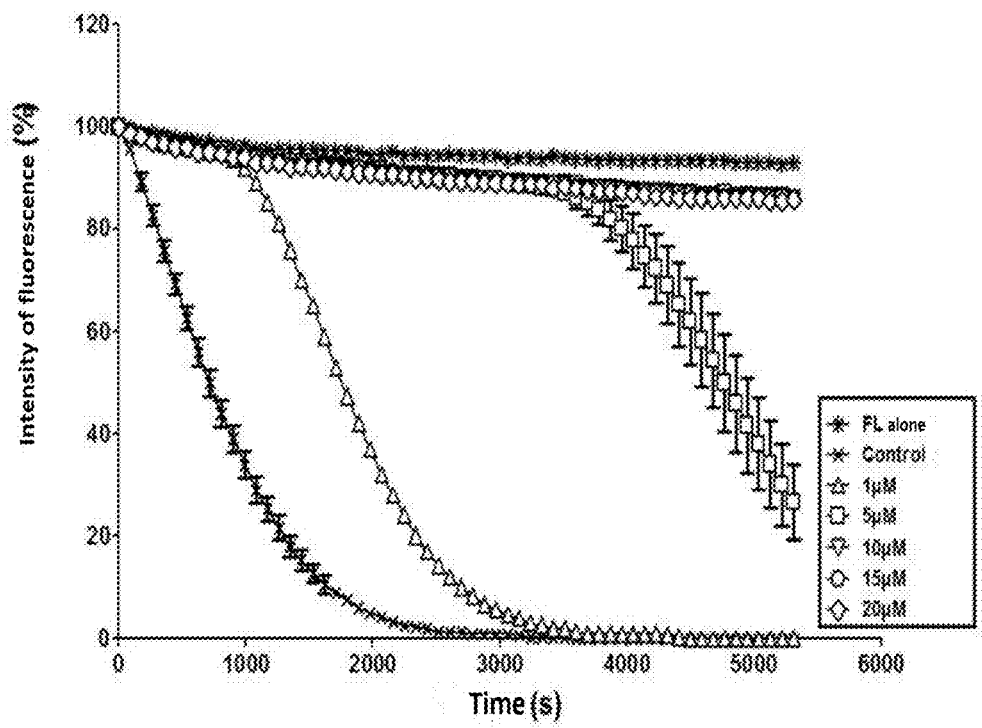

FIG. 18: Decay curve of the fluorescence of the fluorescein induced by the AAPH. The values shown concern the results obtained in the absence (control) or in the presence of the compound 30b at different concentrations and are expressed by the mean±SEM of triplicates constituting a representative experiment from the three independent experiments conducted.

Figure 19:
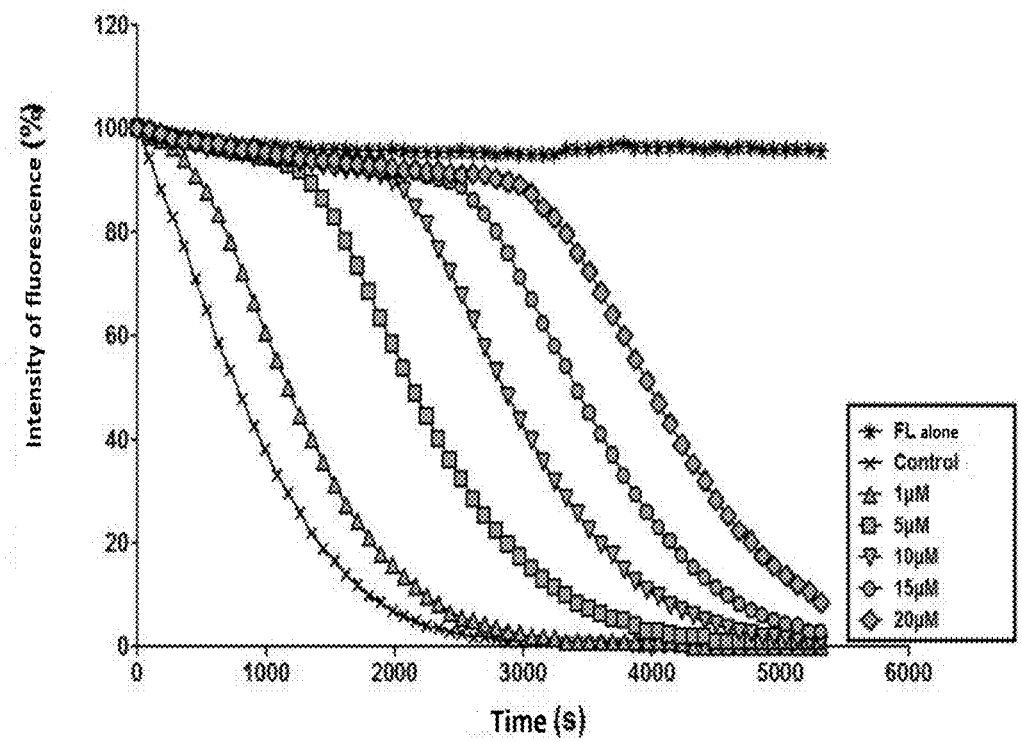

FIG. 19: Decay curve of the fluorescence of the fluorescein induced by the AAPH. The values shown concern the results obtained in the absence (control) or in the presence of the compound 37a at different concentrations and are expressed by the mean±SEM of triplicates constituting a representative experiment from the three independent experiments conducted.

Figure 20:
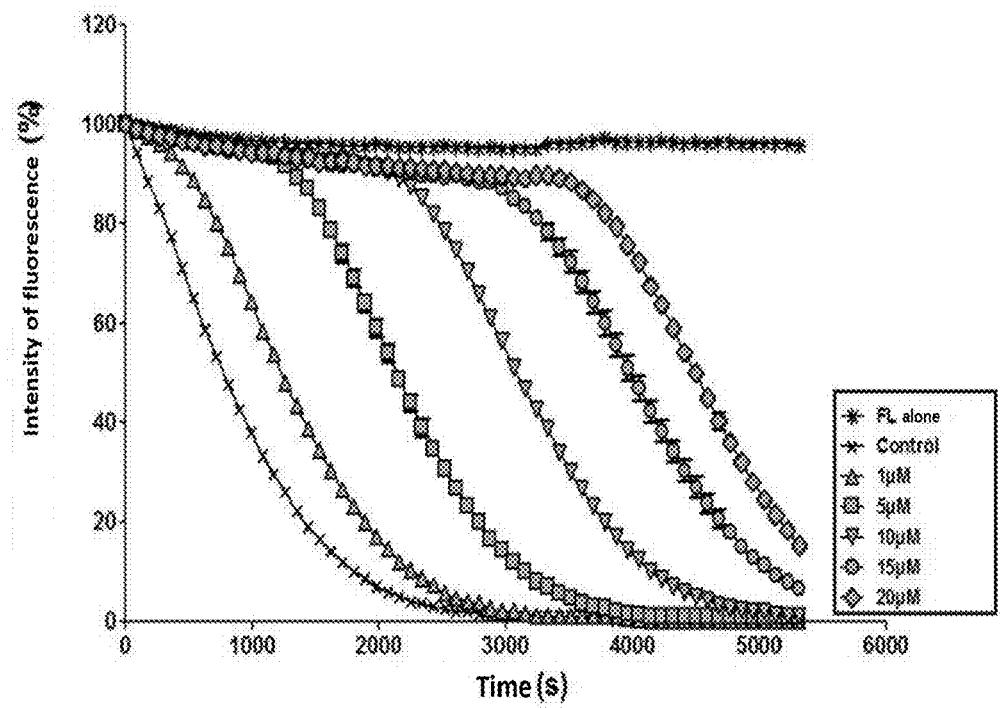

FIG. 20: Decay curve of the fluorescence of the fluorescein induced by the AAPH. The values shown concern the results obtained in the absence (control) or in the presence of the compound 37b at different concentrations and are expressed by the mean±SEM of triplicates constituting a representative experiment from the three independent experiments conducted.

Figure 21:
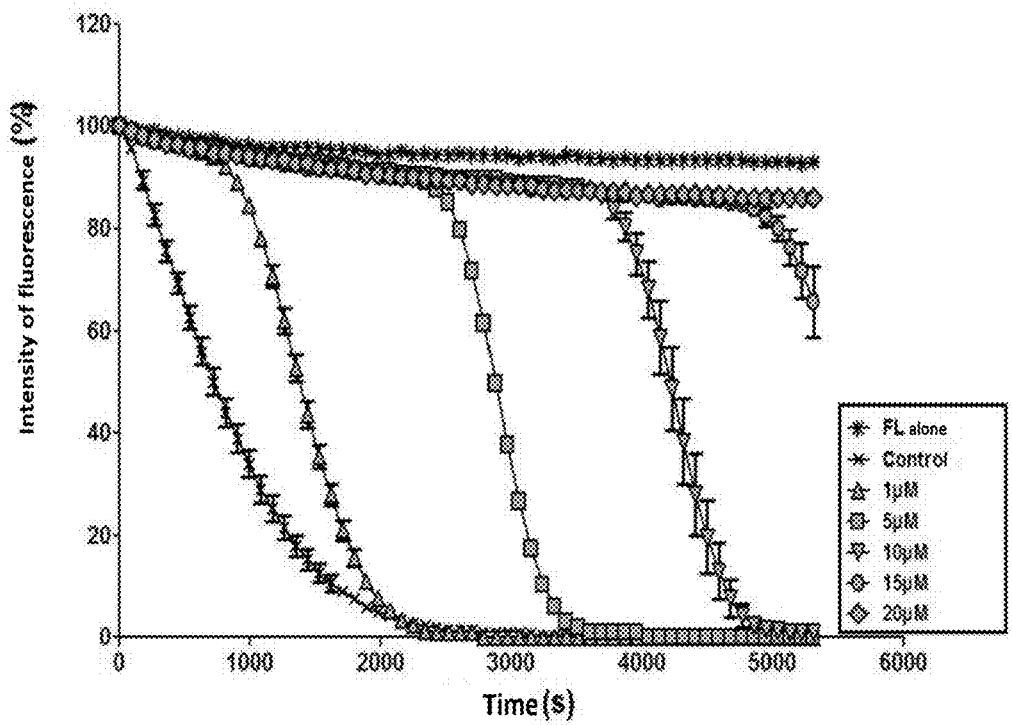

FIG. 21: Decay curve of the fluorescence of the fluorescein induced by the AAPH. The values shown concern the results obtained in the absence (control) or in the presence of the compound 37c at different concentrations and are expressed by the mean±SEM of triplicates constituting a representative experiment from the three independent experiments conducted.

Figure 22:
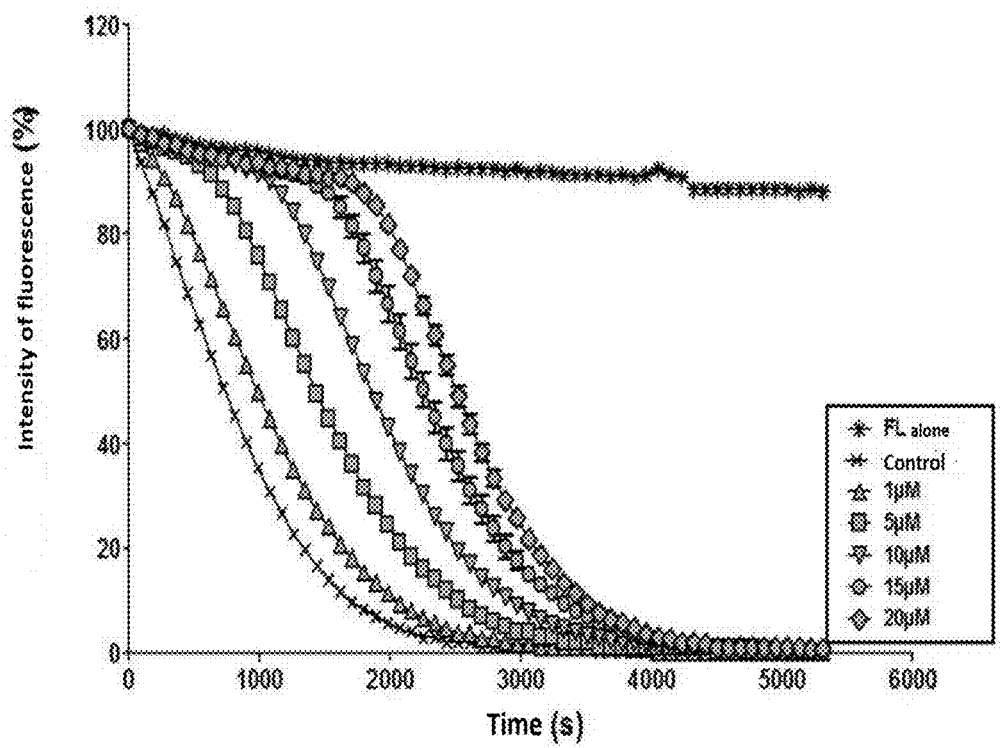

FIG. 22: Decay curve of the fluorescence of the fluorescein induced by the AAPH. The values shown concern the results obtained in the absence (control) or in the presence of the compound 37d at different concentrations and are expressed by the mean±SEM of triplicates constituting a representative experiment from the three independent experiments conducted.

Figure 23:
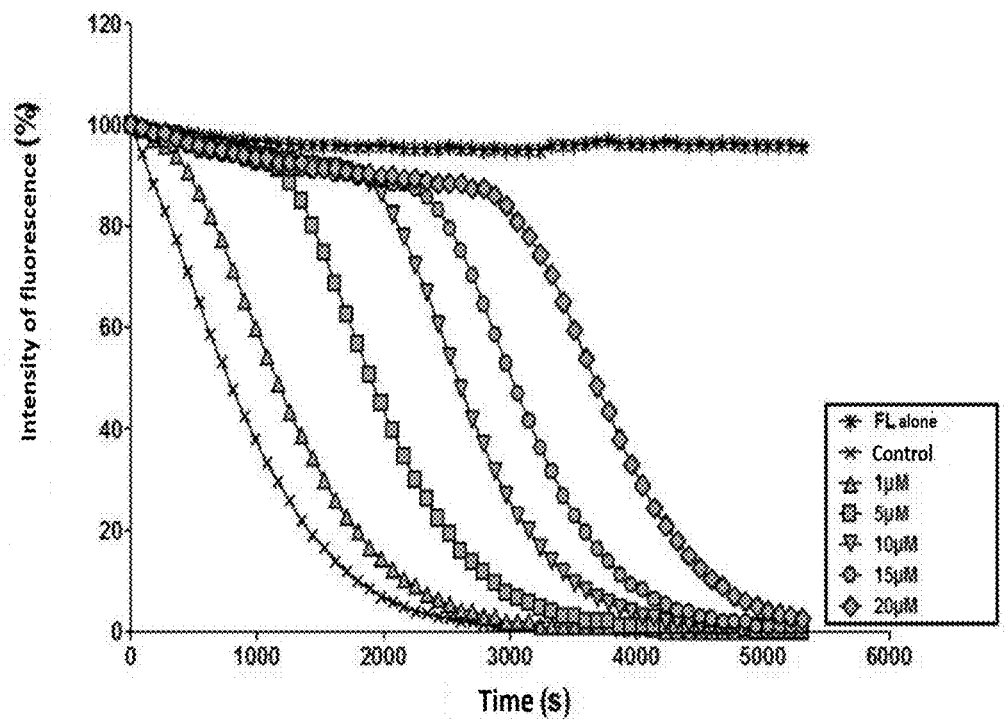

FIG. 23: Decay curve of the fluorescence of the fluorescein induced by the AAPH. The values shown concern the results obtained in the absence (control) or in the presence of the compound 37f at different concentrations and are expressed by the mean±SEM of triplicates constituting a representative experiment from the three independent experiments conducted.

Figure 24:
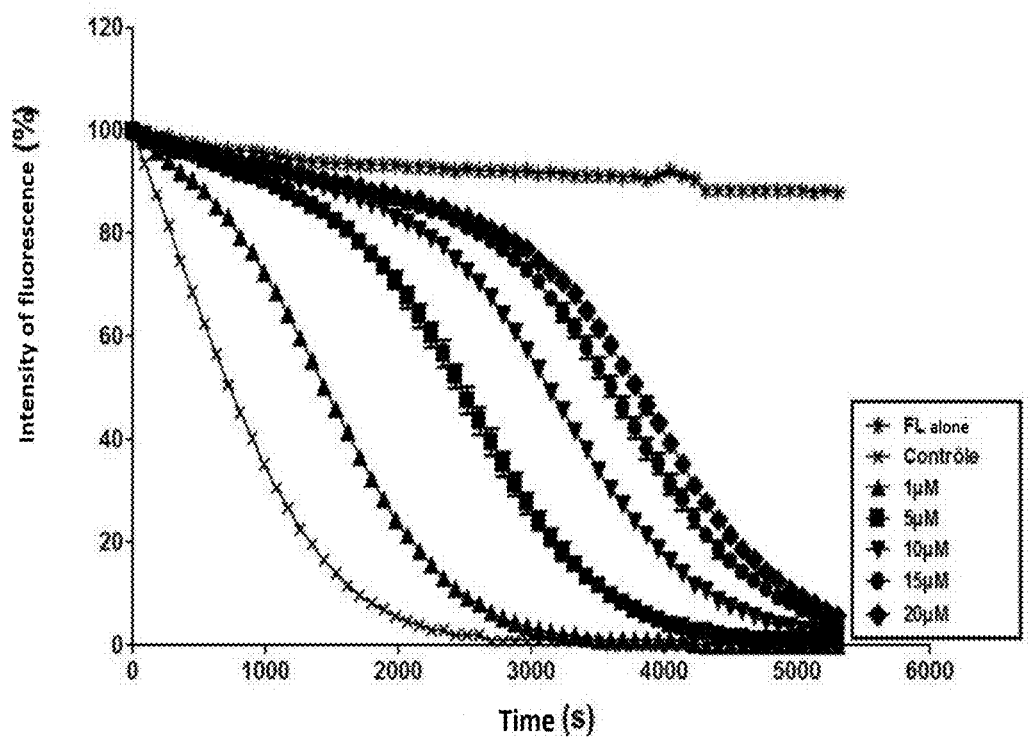

FIG. 24: Decay curve of the fluorescence of the fluorescein induced by the AAPH. The values shown concern the results obtained in the absence (control) or in the presence of the compound 37i at different concentrations and are expressed by the mean±SEM of triplicates constituting a representative experiment from the three independent experiments conducted.

Figure 25:
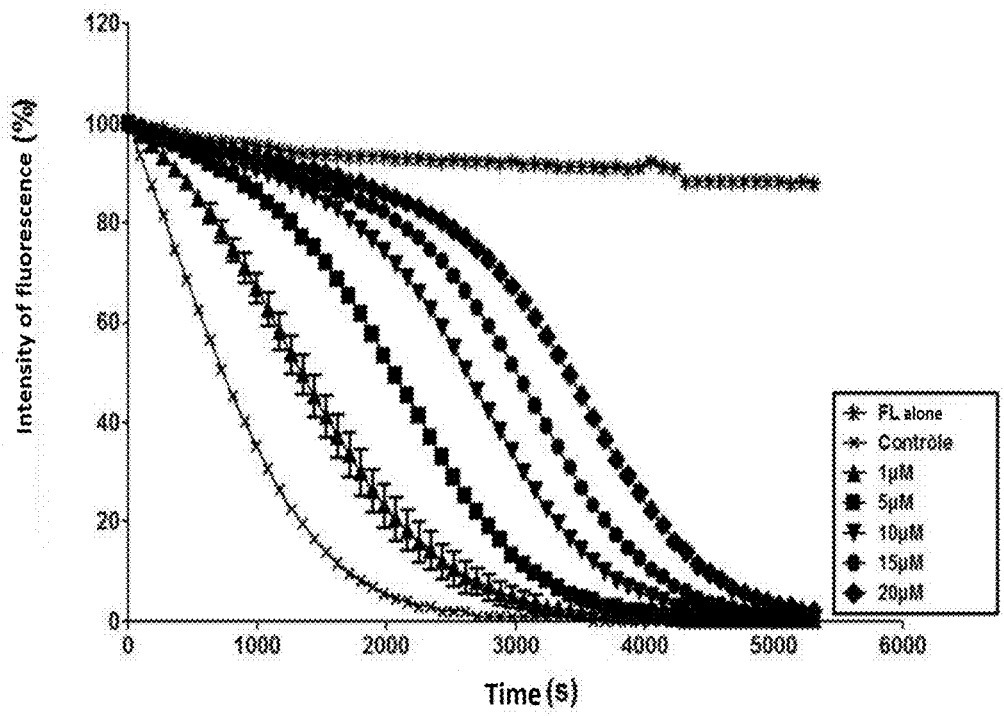

FIG. 25: Decay curve of the fluorescence of the fluorescein induced by the AAPH. The values shown concern the results obtained in the absence (control) or in the presence of the compound 37j at different concentrations and are expressed by the mean±SEM of triplicates constituting a representative experiment from the three independent experiments conducted.

Figure 26:
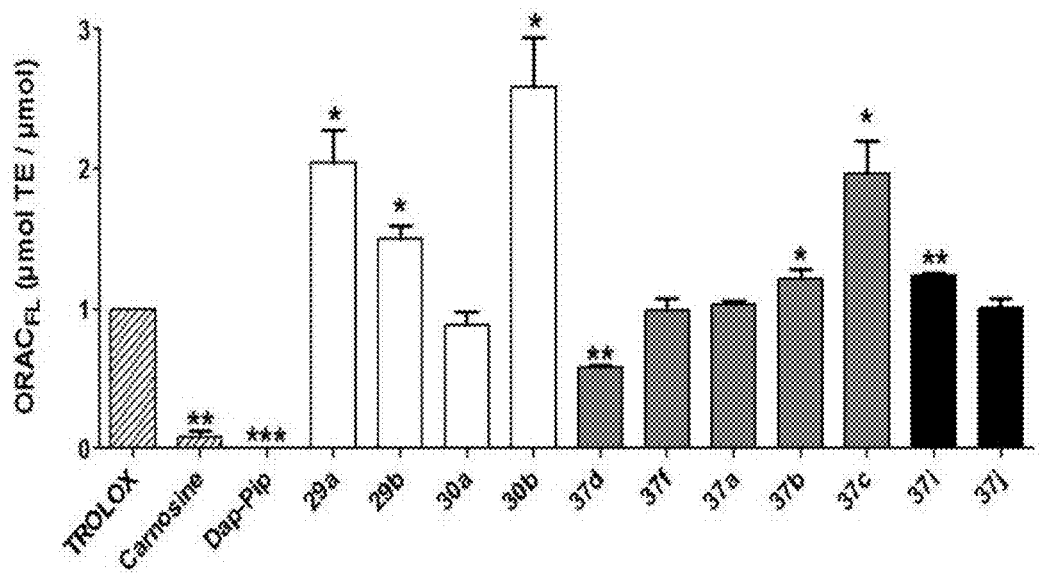

FIG. 26: Antioxidant capacity ($ORAC_{FL}$) of the compounds according to the invention at 10 μM. The results shown correspond to the mean±SEM of three independent experiments conducted in triplicate. *$p<0.05$; $p<0.01$; *$p<0.001$ vs Trolox (Student t-test: if $p<0.05$, the difference is considered to be significant).

Figure 27:
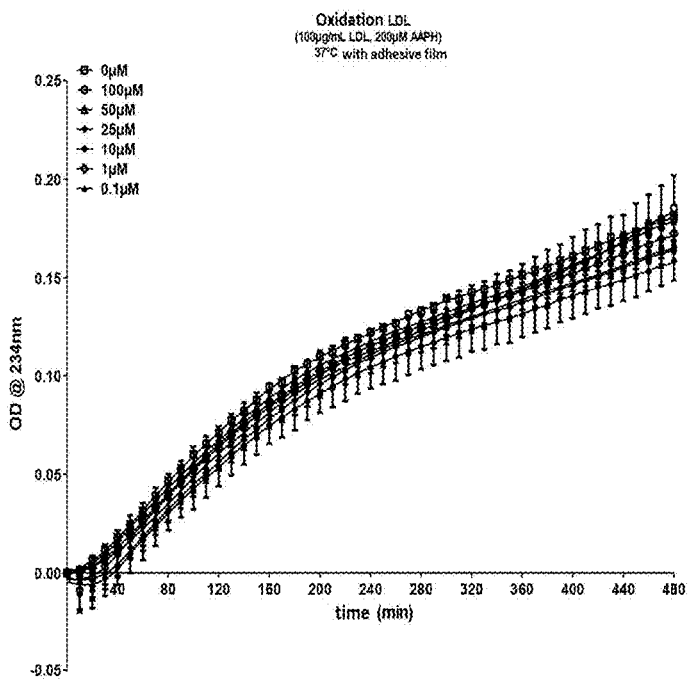

FIG. 27: Evaluation of the antiradical properties of Dap-Pip, a $2^{nd}$ generation compound FIG. 28: Evaluation of the antiradical properties of the compound 29a according to the invention FIG. 29: Evaluation of the antiradical properties of the compound 29b according to the invention FIG. 30: Evaluation of the antiradical properties of the compound 30b according to the invention FIG. 31: Evaluation of the antiradical properties of the compound 37a according to the invention FIG. 32: Evaluation of the antiradical properties of the compound 37c according to the invention FIG. 33: Comparison of the antiradical properties of vitamin E, of $2^{nd}$ generation Dap-Pip and of the various compounds according to the invention at a concentration of 10 μM FIG. 34: Comparison of the antiradical properties of vitamin E, of $2^{nd}$ generation Dap-Pip and of the various compounds according to the invention at a concentration of 1 μM FIG. 35: Study of the cytotoxicity of the compounds according to the invention on murine endothelial brain cells (bEnd.3) after 24 h of treatment. The viability of the cells is expressed by the mean±standard deviation of the triplicates. (a) compounds 29a, 29b, 30b, 37a and 37c; (b) compounds 30a and 37b.

Figure 36:
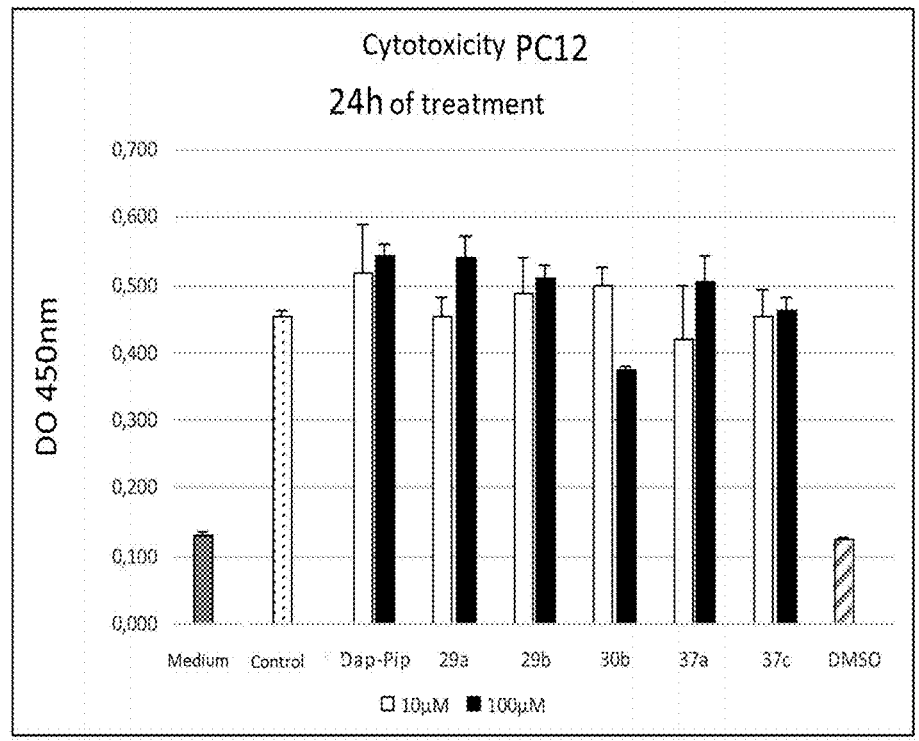
Figure 36:
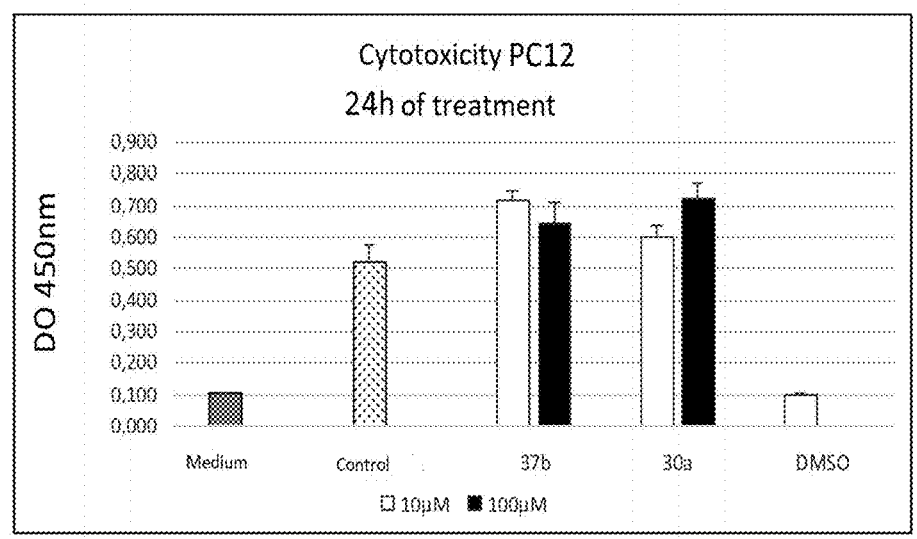

FIG. 36: Study of the cytotoxicity of the compounds according to the invention on rat pheochromocytoma cells, treated as neuronal cells (PC12) after 24 h of treatment. The viability of the cells is expressed by the mean±standard deviation of the triplicates. (a) compounds 29a, 29b, 30b, 37a and 37c; (b) compounds 30a and 37b.

Figure 37:
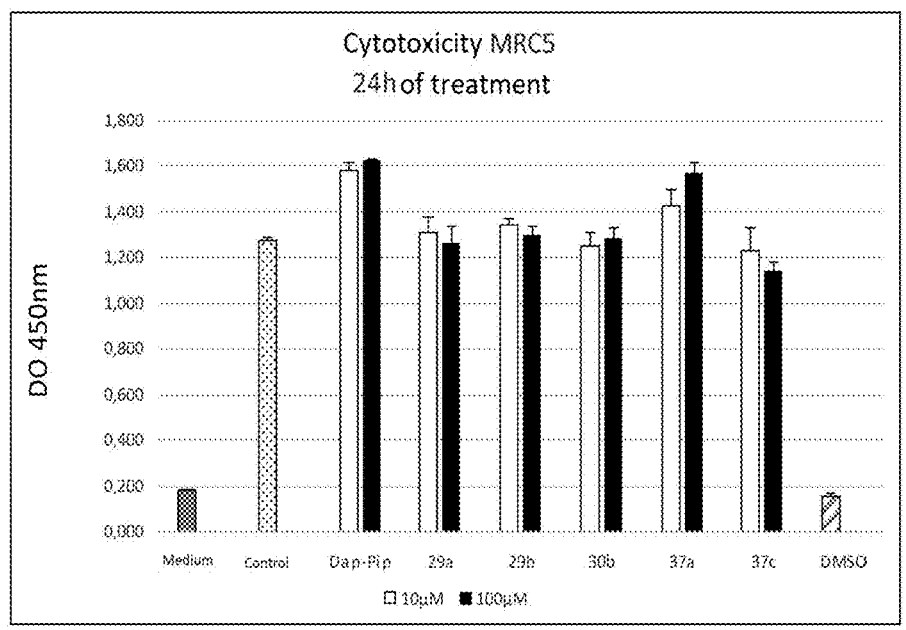
Figure 37:
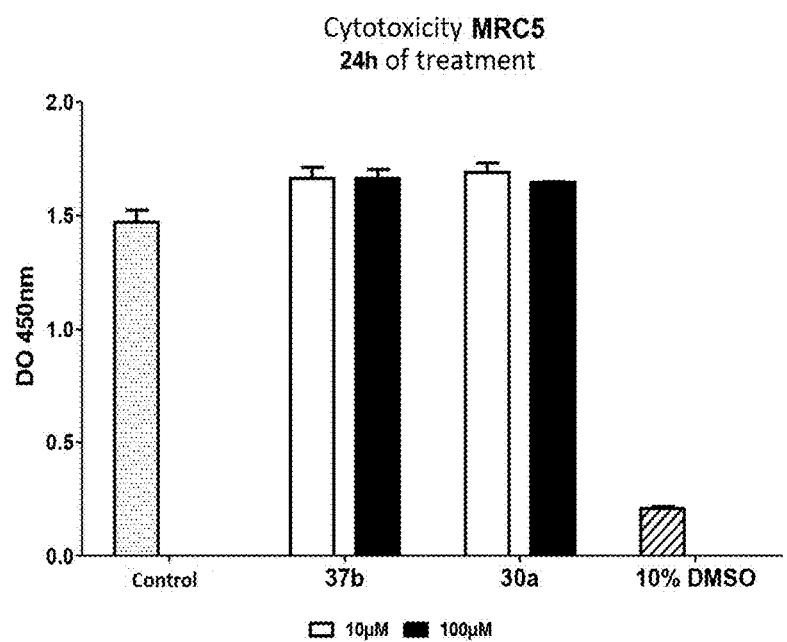

FIG. 37: Study of the cytotoxicity of the compounds according to the invention on human fibroblasts (MRC-5) after 24 h of treatment. The viability of the cells is expressed by the mean±standard deviation of the triplicates. (a) compounds 29a, 29b, 30b, 37a and 37c; (b) compounds 30a and 37b.

Figure 38:
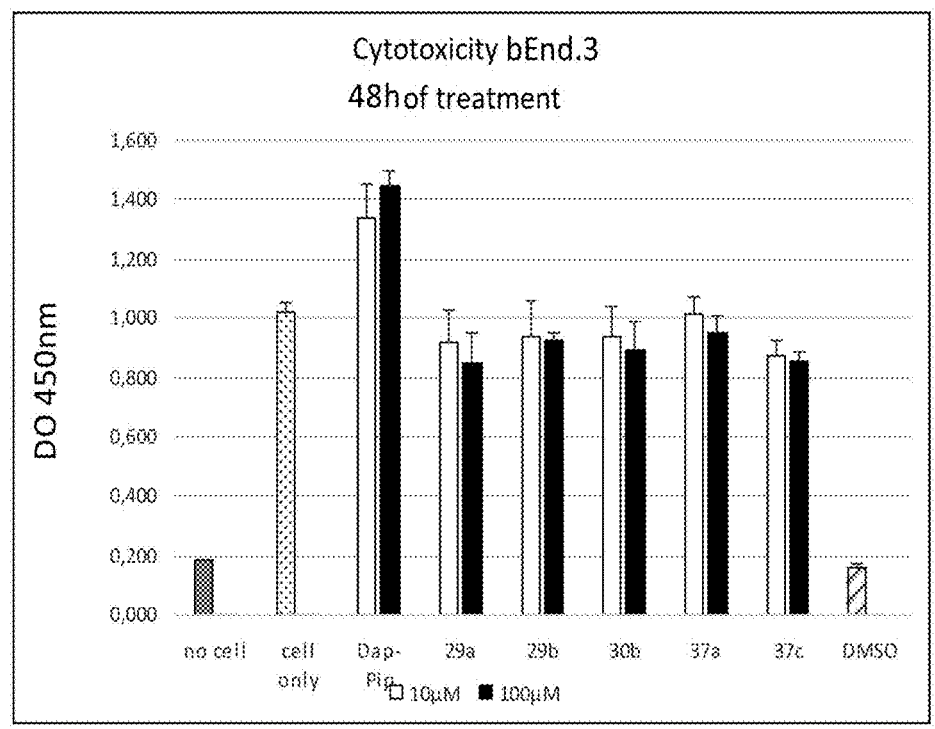
Figure 38:
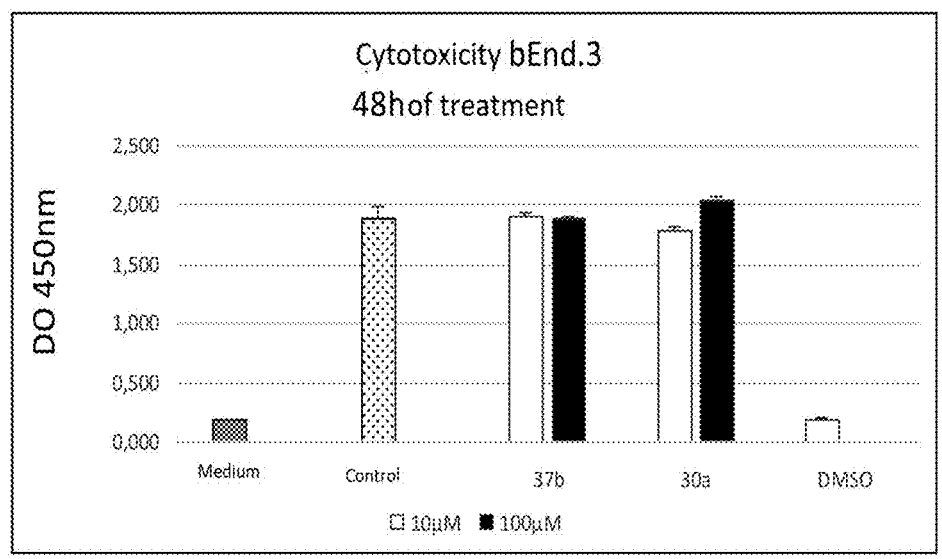

FIG. 38: Study of the cytotoxicity of the compounds according to the invention on murine endothelial brain cells (bEnd.3) after 48 h of treatment. The viability of the cells is expressed by the mean±standard deviation of the triplicates. (a) compounds 29a, 29b, 30b, 37a and 37c; (b) compounds 30a and 37b.

Figure 39:
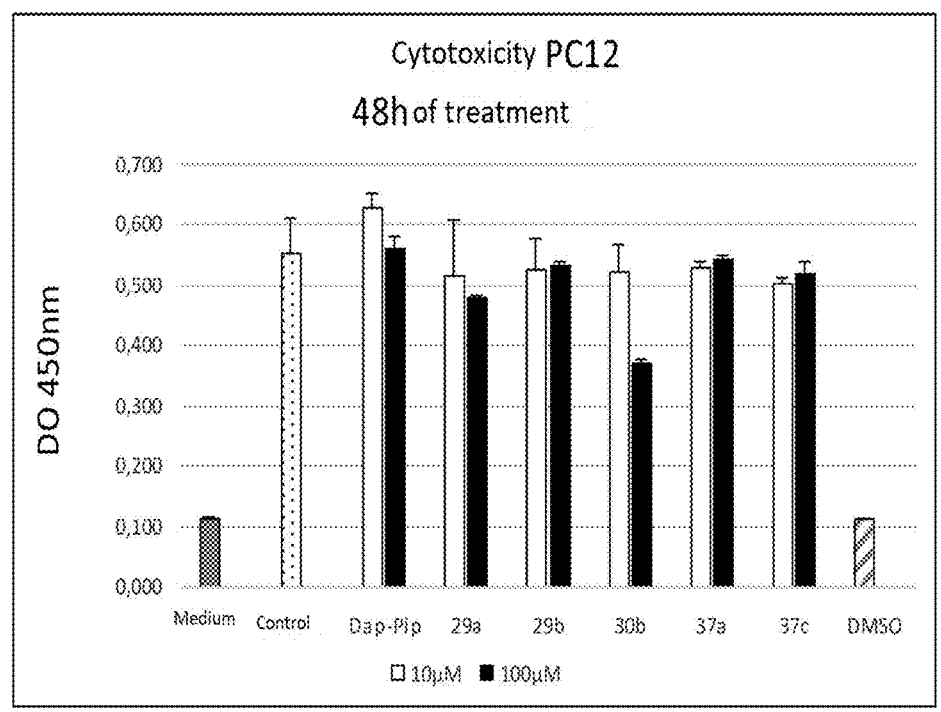
Figure 39:
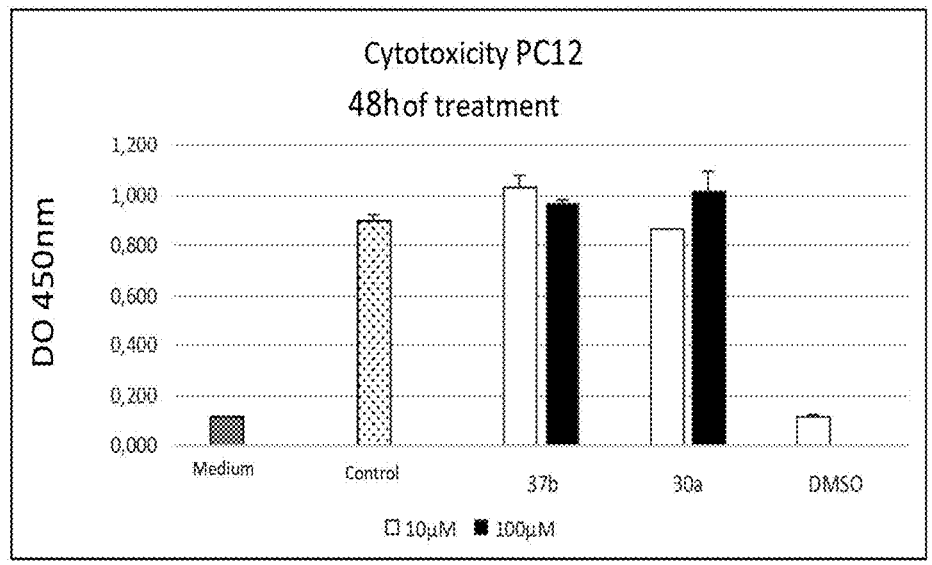

FIG. 39: Study of the cytotoxicity of the compounds according to the invention on rat pheochromocytoma cells, treated as neuronal cells (PC12) after 48 h of treatment. The viability of the cells is expressed by the mean ±standard deviation of the triplicates. (a) compounds 29a, 29b, 30b, 37a and 37c; (b) compounds 30a and 37b.

Figure 40:
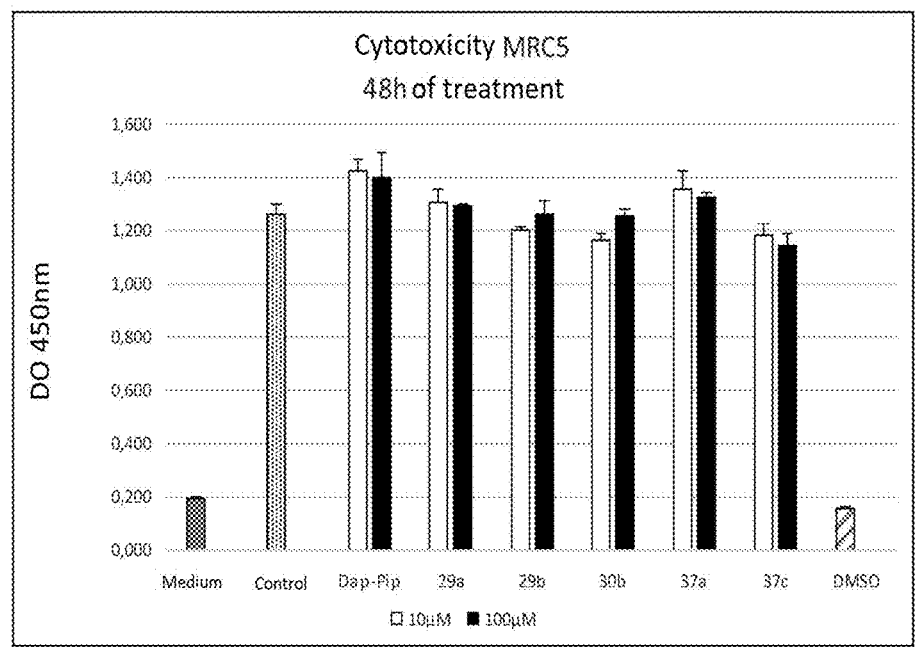
Figure 40:
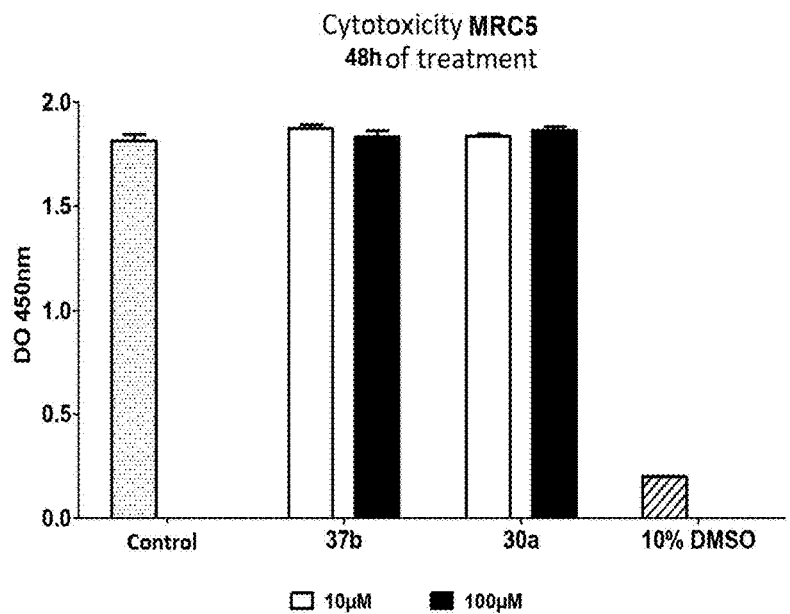

FIG. 40: Study of the cytotoxicity of the compounds according to the invention on human fibroblasts (MRC-5) after 48 h of treatment. The viability of the cells is expressed by the mean±standard deviation of the triplicates. (a) compounds 29a, 29b, 30b, 37a and 37c; (b) compounds 30a and 37b.

Figure 41:
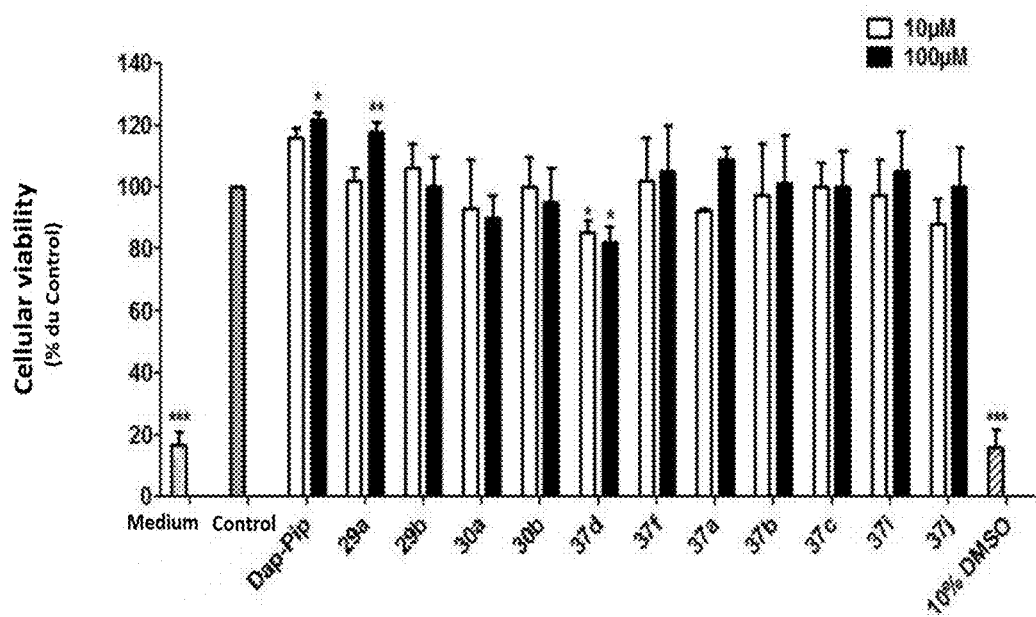

FIG. 41: Study of the cytotoxicity of the compounds according to the invention (29a, 29b, 30a, 30b, 37a, 37b, 37c, 37d, 37f, 37i and 37j) on rat pheochromocytoma cells, treated as neuronal cells (PC12) after 24 h of treatment. The viability of the cells is expressed by the mean±SEM of three independent experiments conducted in triplicate.

Figure 42:
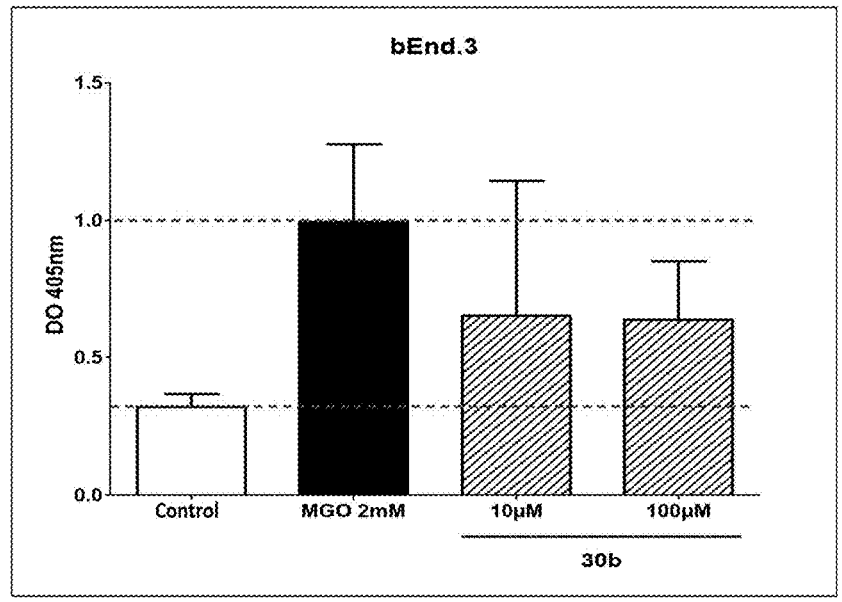

FIG. 42: Evaluation of the anti-apoptotic properties of the compound 30b on murine endothelial brain cells (bEnd.3). The cellules bEnd.3 were pretreated 30 min with 10 μM or 100 μM of 30b before the adding of 2 mM of MGO, then incubated for 24 h. The apoptosis of the cells is expressed by the mean±standard deviation of the triplicates.

Figure 43:
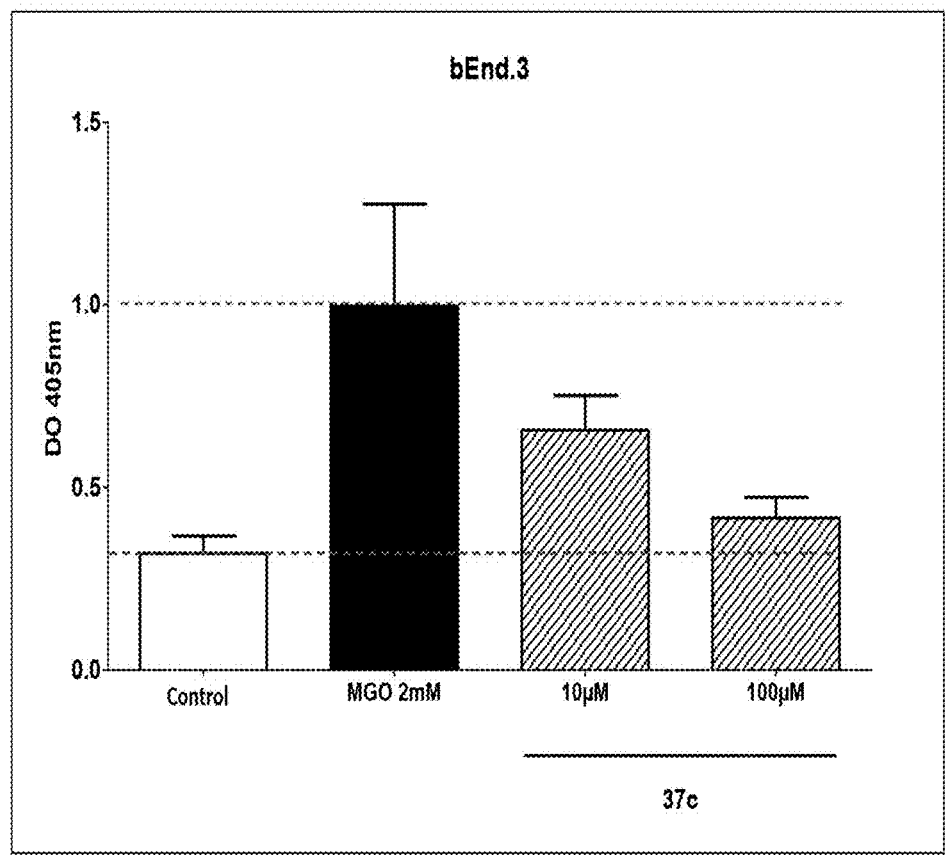

FIG. 43: Evaluation of the anti-apoptotic properties of the compound 37c on murine endothelial brain cells (bEnd.3). The cellules bEnd.3 were pretreated 30 min with 10 μM or 100 μM of 37c before the adding of 2 mM of MGO, then incubated for 24 h. The apoptosis of the cells is expressed by the mean±standard deviation of the triplicates.

Figure 44:
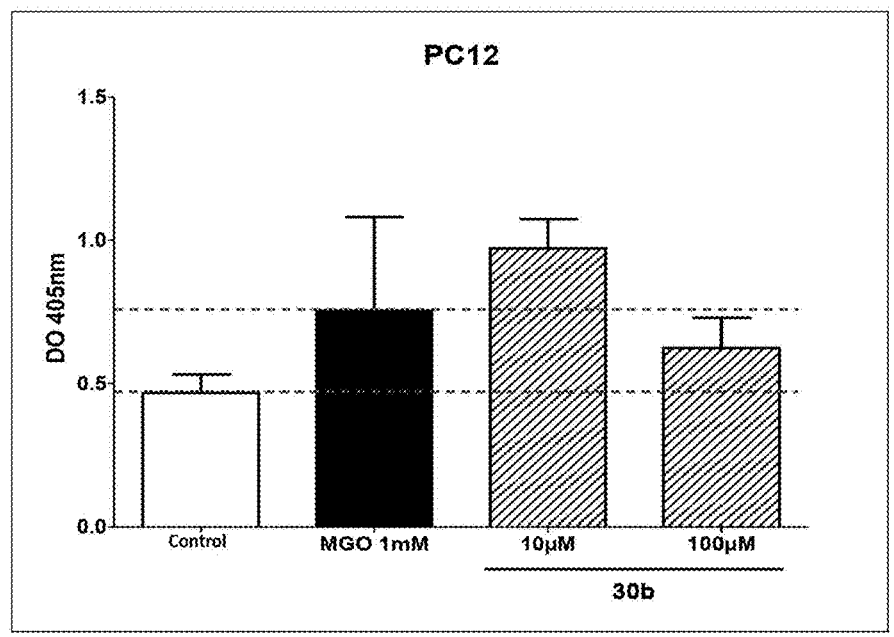

FIG. 44: Evaluation of the anti-apoptotic properties of the compound 30b on rat pheochromocytoma cells, treated as neuronal cells (PC12). The cellules PC12 were pretreated 30 min with 10 μM or 100 μM of 30b before the adding of 1 mM of MGO, then incubated for 24 h. The apoptosis of the cells is expressed by the mean±standard deviation of the triplicates.

Figure 45:
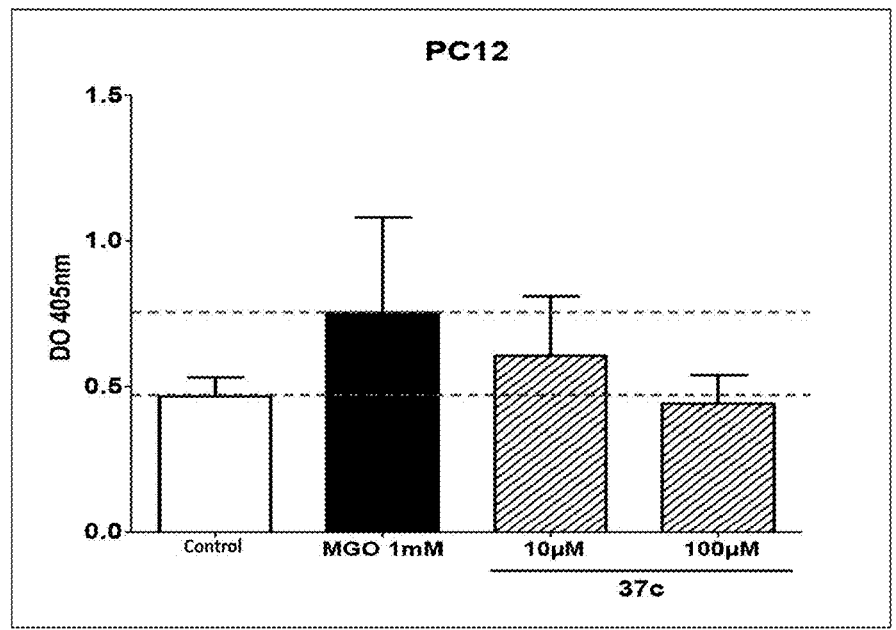

FIG. 45: Evaluation of the anti-apoptotic properties of the compound 37c on rat pheochromocytoma cells, treated as neuronal cells (PC12). The cellules PC12 were pretreated 30 min with 10 μM or 100 μM of 37c before the adding of 1 mM of MGO, then incubated for 24 h. The apoptosis of the cells is expressed by the mean±standard deviation of the triplicates.

Figure 46:
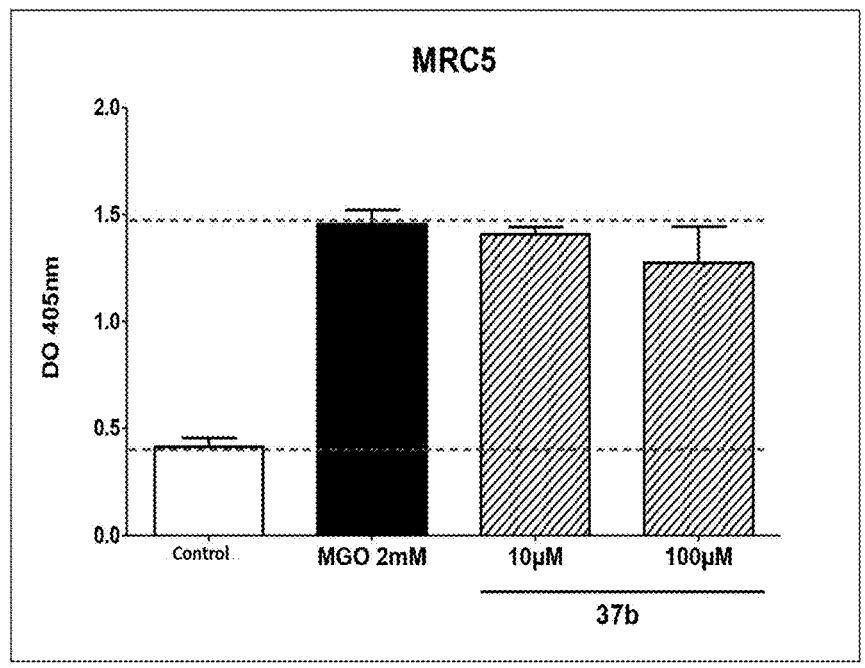

FIG. 46: Evaluation of the anti-apoptotic properties of the compound 37b on human fibroblasts (MRC-5). The cellules MRCS were pretreated for 1 h with 10 µM or 100 µM of 37b before the adding of 2 mM of MGO, then incubated for 24 h. The apoptosis of the cells is expressed by the mean ±standard deviation of the triplicates.

Figure 47:
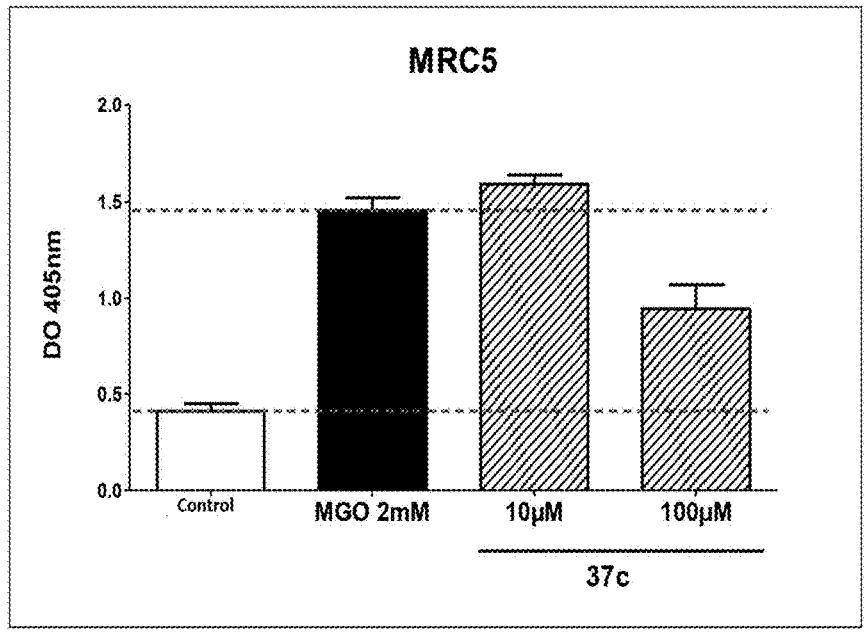

FIG. 47: Evaluation of the anti-apoptotic properties of the compound 37c on human fibroblasts (MRC-5). The cellules MRCS were pretreated for 1 h with 10 µM or 100 µM of 37c before the adding of 2 mM of MGO, then incubated for 24 h. The apoptosis of the cells is expressed by the mean±standard deviation of the triplicates.

Figure 48:
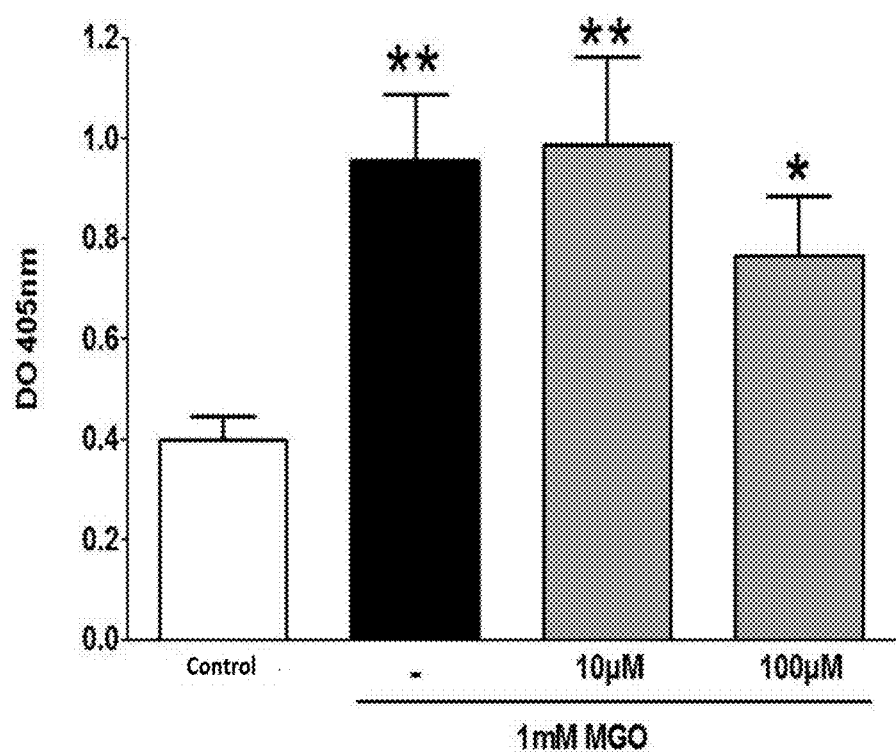

FIG. 48: Evaluation of the anti-apoptotic properties of the compound 37c on rat pheochromocytoma cells, treated as neuronal cells (PC12). The cellules PC12 were pretreated 1 h with 10 µM or 100 µM of 37c before the adding of 1 mM of MGO, then incubated for 24 h. The apoptosis of the cells is expressed by the mean±SEM of three independent experiments conducted in triplicate. *p<0.05; **p<0.01 vs control (cells not treated by MGO) (Student t-test: if p<0.05, the difference is considered to be significant).

EXAMPLES

A. Synthesis
I) Equipment and Methods

The various reaction products were purchased from Sigma-Aldrich (Lyons, France), and are used without additional purifications. The TLCs were carried out on Merck 60F254 silica plates, observed in ultraviolet light ($\lambda$=254 nm) before being revealed using phosphomolybdic acid in ethanol 95% followed by heating until maximum colouration. The preparative column chromatographies were carried out via the chromatographic technique on Kielselgel 60 silica gel (40-63 µm) (Merck) or using a Reveleris® (Grace) flash chromatography system in normal phase.

The NMR analyses were carried out on a Bruker AC300, 400 or 600 apparatus. The chemical shifts are expressed in parts per million (ppm) with respect to the deuterated solvent used as an internal reference. The coupling constants (J) are expressed in Hertz (Hz) and the signal multiplicity is symbolised as follows: s (singulet), d (doublet), t (triplet), q (quadruplet) and m (multiplet). The mass spectra were obtained on a Shimadzu LCMS-2020 apparatus for the MSs and a Micromass Q-TOF Ultima apparatus for the HRMSs, in positive electrospray ionisation mode (ESI+).

II) Synthesis of the Compounds According to the Invention

1—Synthesis of the Starting Diamine Synthons a) Derivatives from Aspartic Acid and Glutamic Acid (Scheme 1)

Scheme 1: Development of the synthons derived from aspartic and glutamic acids

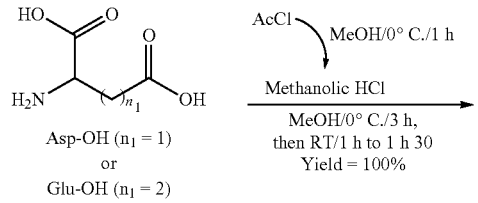

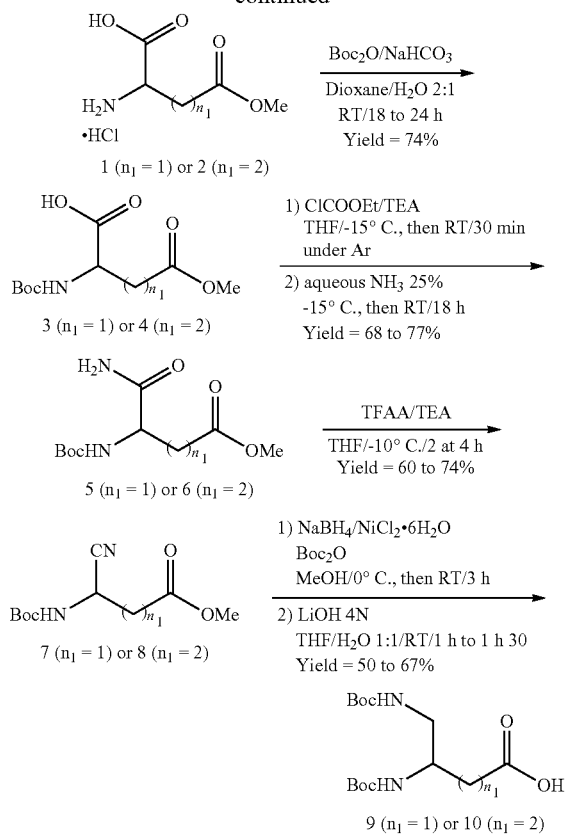

Compounds 1 (Bioconjug. Chem., 2007, 18, 1625-1636) and 2 (J. Med. Chem., 2009 52, 4650-4656):

The first step of the synthesis (

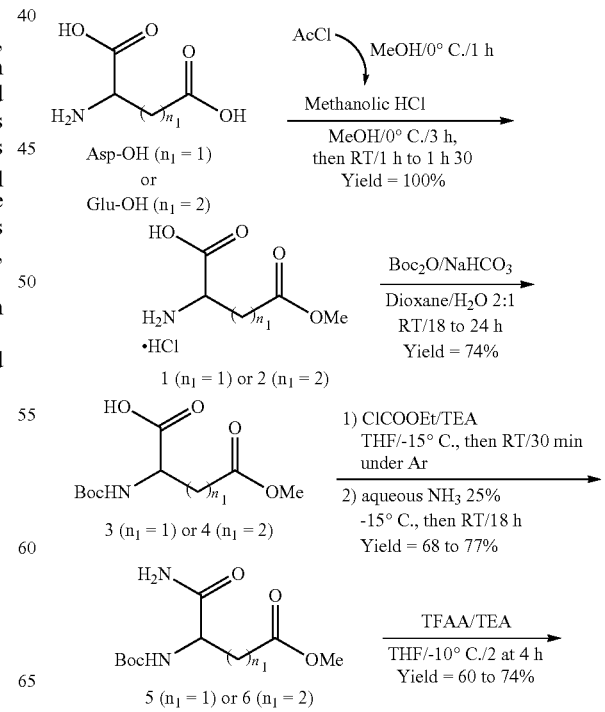

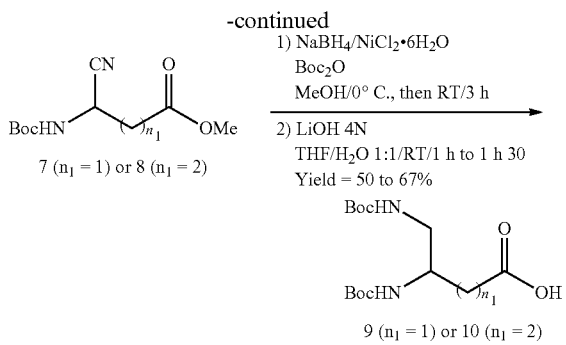

1) making it possible to obtain a methyl ester starting with the aspartic acid was previously developed by Wojciechowski et al. (Bioconjugate Chem., 2007, 18, 1625-1636) and was in this case, transposed to glutamic acid.

Compounds 3 (WO 2013/030193 A1) and 4 (J. Med. Chem., 2009 52, 4650-4656):

Ollivier et al (Tetrahedron Lett., 2010, 51, 4147-4149) and More et al. (J. Med. Chem., 2009, 52, 4650-4656) respectively described the protection conditions used for the amine group of methyl esters 1 and 2 by a t-butyloxycarbonyl group.

Compounds 5 and 6 (J. Chem. Soc., Perkin Trans. 1, 1999, 2057-2060):

To a solution of the compound 3 or 4 (38.3-40.4 mmol) in anhydrous THF (150 mL), placed under stirring at −15° C. and under Ar, are successively added triethylamine (1.1 eq) and ethyl chloroformate (1.4 eq) dissolved in anhydrous THF (50 mL)) dropwise. After stirring for 30 min at −15° C., a 25% ammonia solution (2.5-2.7 eq in a final volume final of 16 mL) is introduced into the reaction medium which is then placed under stirring at −15° C., then at room temperature for 18 h. The THF is then evaporated under reduced pressure and the desired product is extracted using ethyl acetate. The organic phase is washed with a solution of $KHSO_4$ 1N, then $NaHCO_3$ 10% and a saturated solution of NaCl, dried over $Na_2SO_4$ and finally evaporated under reduced pressure in order to respectively give the derivative 5 or 6 in the form of a white powder (68 or 77%).

Compound 5: $^1$H NMR (CDCl$_3$, 300 MHz): δ (ppm) 6.59 (s, 1H); 6.20 (s, 1H); 5.79-5.76 (s, 1H); 4.50-4.49 (m, 1H); 3.65 (s, 3H); 2.91 (dd, J=16.9 Hz and J'=4.8 Hz, 1H); 2.66 (dd, J=18.7 Hz and J'=5.7 Hz, 1H); 1.40 (s, 9H).

$^{13}$C NMR (CDCl$_3$, 75 MHz): δ (ppm) 173.2; 171.9; 155.1; 80.1; 51.7; 49.9; 35.6; 27.9 (3C).

MS (ESI+): m/z=[M+H] 247.1; [M+Na] 269.1; [M+MeCN+Na] 310.1.

HRMS (ESI+): m/z calculated for $C_{10}H_{18}N_2O_5Na$ [M+Na]=269.1113; found=269.1103.

Compounds 7 and 8:

To a solution of the compound 5 or 6 (26.4-28.8 mmol) in THF (100 mL), placed under stirring at −10° C., are added trifluoroacetic anhydride (1.5 eq) and triethylamine (3 eq) (Synth. Commun., 2009, 39, 395-406). The reaction medium is then placed under stirring at this same temperature for 2 to 4 h. The THF is then evaporated under reduced pressure and the desired product is extracted using ethyl acetate. The organic phase is washed with a solution of $KHSO_4$ N, then $NaHCO_3$ 10% and a saturated solution of NaCl, dried over $Na_2SO_4$ and finally evaporated under reduced pressure in order to respectively give the derivative 7 or 8 in the form of a yellow solid (60 or 74%) after purification on a silica column using a $CH_2Cl_2$/MeOH 98:2 mixture or by flash chromatography in normal phase using a $CH_2Cl_2$/MeOH 100:0 to 90:10 gradient.

Compound 7: $^1$H NMR (CDCl$_3$, 300 MHz) δ (ppm): 5.61 (s, 1H); 4.90 (m, 1H); 3.75 (s, 3H); 2.86-2.82 (m, 2H); 1.39 (s, 9H).

$^{13}$C NMR (CDCl$_3$, 75 MHz) δ (ppm): 159.0; 117.9; 80.3; 52.6; 37.4; 28.4 (3C).

MS (ESI+): m/z=[M+H] 229.2; [M+MeCN+Na] 292.1; [2M+Na+H] 480.2.

HRMS (ESI+): m/z calculated for $C_{10}H_{16}N_2O_4Na$ [M+Na]=251.1008; found=251.1000.

Compound 8: $^1$H NMR (CDCl$_3$, 600 MHz): δ (ppm) 5.41 (s, 1H); 4.62 (m, 1H); 3.67 (s, 3H); 2.53-2.46 (m, 2H); 2.13-2.10 (m, 2H); 1.41 (s, 9H).

$^{13}$C NMR (CDCl$_3$, 150 MHz): δ (ppm) 172.6; 154.5; 118.8; 81.2; 52.0; 41.6; 29.6; 28.2 (3C); 28.2.

MS (ESI+): m/z=[M+H] 243.1; [M+Na] 265.1; [M+K] 281.0; [M+MeCN+Na] 306.1.

HRMS (ESI+): m/z calculated for $C_{11}H_{18}N_2O_4Na$ [M+Na]=265.1164; found=265.1159.

Compounds 9 and 10:

To a solution of the compound 7 or 8 (15.3-19.8 mmol) in methanol (150 mL), placed under stirring at 0° C., are added di-t-butyl dicarbonate (2 eq) and $NiCl_2.6H_2O$ (0.1 eq). Sodium borohydride (8 eq) is then introduced in small portions over a period of 1 h and the mixture is placed under stirring at room temperature for 3 h (Tetrahedron, 2003, 59, 5417-5423). After the adding of diethylenetriamine (2 eq) and stirring again for 30 min to 1 h, the methanol is evaporated under reduced pressure and the desired product is extracted using ethyl acetate. The organic phase is washed with a saturated solution of $NaHCO_3$, then NaCl, dried over $Na_2SO_4$ and finally evaporated under reduced pressure. The intermediate compound obtained is then dissolved in a THF/H$_2$O 1:1 mixture (40 mL) and an aqueous solution of LiOH 4N (4 eq) is then introduced into the medium which is kept under stirring for 1 h to 1 h30. The THF is evaporated under reduced pressure, then the mixture is taken in diethyl ether or ethyl acetate and alkalised with a solution of $Na_2CO_3$ 10% in order to eliminate the methyl ester and the di-t-butyl dicarbonate remaining in the organic phase. The aqueous phase is then acidified using a solution of HCl 6N and the desired product is then extracted using diethyl ether or ethyl acetate. After washing with a saturated solution of NaCl, the organic phase is finally dried over $Na_2SO_4$ and evaporated under reduced pressure in order to respectively give the derivative 9 or 10 in the form of a white powder (50 or 67%).

Compound 9: $^1$H NMR (CDCl$_3$, 300 MHz): δ (ppm) 8.70-8.61 (s, 1H); 5.54-5.41 (s, 1H); 5.15 (s, 1H); 4.00-3.98 (m, 1H); 3.37-3.25 (m, 2H); 2.65-2.59 (m, 2H); 1.43 (s, 18H).

$^{13}$C NMR (CDCl$_3$, 75 MHz): δ (ppm) 174.7; 174.6; 146.2 (2C); 79.9; 79.8; 48.0; 43.4; 36.4; 28.1 (6C).

MS (ESI+): m/z=[M+H] 319.2; [M+Na] 341.2; [M+MeCN+Na] 382.2.

HRMS (ESI+): m/z calculated for $C_{14}H_{26}N_2O_6Na$ [M+Na]=341.1689; found=341.1676.

Compound 10: $^1$H NMR (CDCl$_3$, 300 MHz): δ (ppm) 8.35-8.28 (s, 1H); 5.06 (s, 1H); 4.99-4.96 (s, 1H); 3.72-3.66 (m, 1H); 3.18-3.16 (m, 2H); 2.43-2.37 (m, 2H); 1.87-1.76 (m, 2H); 1.43 (s, 18H).

$^{13}$C NMR (CDCl$_3$, 75 MHz): δ (ppm) 177.4; 156.8; 156.5; 79.6 (2C); 51.0; 44.6; 30.5; 28.3 (6C), 27.7.

MS (ESI+): m/z=[M+Na] 355.9; [M+MeCN+Na] 396.2.

HRMS (ESI+): m/z calculated for $C_{15}H_{28}N_2O_6Na$ [M+Na]=355.1845; found=355.1855.

b) Derivatives of Ornithine and of Lysine (Scheme 2)

Scheme 2: Development of the synthons derived from ornithine and from lysine

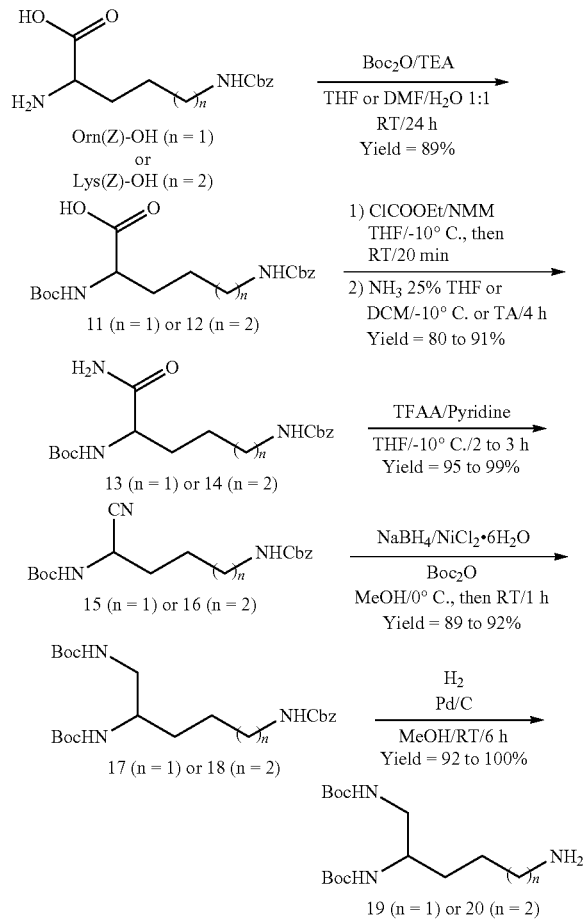

Compounds 11 and 12 (Off-the-Shelf)

Compounds 13 (WO 07/011623 A1) and 14 (WO 00/64865 A1):

To a solution of the compound 11 or 12 (1 eq) (13.7-24.5 mmol) in THF (50-150 mL), placed under stirring at −10° C., are successively added N-methylmorpholine (1.1 eq) and ethyl chloroformate (1.1 eq). After stirring for 20 min at −10° C., a 25% ammonia solution (2.5 eq in a final volume final of 16 mL) is introduced into the reaction medium which is then placed under storage for 4 h. The THF is then evaporated under reduced pressure and the desired product is extracted using ethyl acetate. The organic phase is washed with a solution of $KHSO_4$ 1N, then $NaHCO_3$ 10% and a saturated solution of NaCl, dried over $Na_2SO_4$ and finally evaporated under reduced pressure in order to respectively give the derivative 13 or 14 in the form of a white powder (91 or 80%) after recrystallisation using a AcOEt/Cyclohexane 20:80 mixture.

Compounds 15 and 16 (WO 2000/64865 A1):

To a solution of the compound 13 or 14 (8.1-10 mmol) in THF (60-70 mL), placed under stirring at −10° C., are added trifluoroacetic anhydride (1.5 eq) and pyridine (3 eq). The reaction medium is then placed under stirring at this same temperature for 2 h. The THF is then evaporated under reduced pressure and the desired product is extracted using ethyl acetate. The organic phase is washed with a solution of $KHSO_4$ 1N, then $NaHCO_3$ 10% and a saturated solution of NaCl, dried over $Na_2SO_4$ and finally evaporated under reduced pressure in order to respectively give the derivative 15 or 16 in the form of a white powder (99 or 95%) after recrystallisation using a AcOEt/Cyclohexane 20:80 mixture.

Compound 15: $^1$H NMR (CDCl$_3$, 600 MHz): δ (ppm) 7.36-7.29 (m, 5H); 5.11 (s, 1H); 5.08 (s, 2H); 4.96 (s, 1H); 4.55 (m, 1H); 3.24-3.23 (m, 2H); 1.81-1.79 (m, 2H); 1.68-1.65 (m, 2H); 1.44 (s, 9H).

$^{13}$C NMR (CDCl$_3$, 150 MHz): δ (ppm) 156.6 (2C); 136.4; 128.5 (2C); 128.2; 128.1 (2C); 118.7; 79.1; 66.8; 42.0; 40.0; 29.6; 28.2 (3C); 26.1.

MS (ESI+): m/z=[M+Na] 370.2; [2M+Na] 717.3.

HRMS (ESI+): m/z calculated for $C_{18}H_{25}N_3O_4Na$ [M+Na]=370.1743; found=370.1749.

Compounds 17 and 18:

To a solution of the compound 15 or 16 (8-10 mmol) in methanol (60-80 mL), placed under stirring at 0° C., are added di-t-butyl dicarbonate (2 eq) and NiCl$_2$.6H$_2$O (0.1 eq). Sodium borohydride (7 eq) is then introduced in small portions over a period of 30 min to 1 h and the mixture is placed under stirring at room temperature for 1 h. After the adding of diethylenetriamine (1 eq) and stirring again for 30 min to 1 h, the methanol is evaporated under reduced pressure and the desired product is extracted using ethyl acetate. The organic phase is washed with a saturated solution of NaHCO$_3$, then NaCl, dried over Na$_2$SO$_4$ and finally evaporated under reduced pressure in order to respectively give the derivative 17 or 18 in the form of a white powder (92 or 89%).

Compound 17: $^1$H NMR (CDCl$_3$, 300 MHz): δ (ppm) 7.34-7.31 (m, 5H); 5.06 (s, 2H); 5.06 (s, 1H); 4.94 (s, 1H); 4.80-4.77 (m, 1H); 3.58 (m, 1H); 3.21-3.12 (m, 4H); 1.56-1.52 (m, 2H); 1.45-1.44 (m, 2H); 1.43 (s, 18H).

$^{13}$C NMR (CDCl$_3$, 75 MHz): δ (ppm) 172.0; 156.9 (2C); 136.9; 128.8 (2C); 127.4 (3C); 79.7 (2C); 67.0; 51.5; 44.8; 41.1; 30.4; 28.7 (6C); 26.5.

MS (ESI+): m/z=[M+H] 452.1; [M+Na] 474.0.

HRMS (ESI+): m/z calculated for $C_{23}H_{37}N_3O_6Na$ [M+Na]=474.2580; found=474.2560.

Compound 18: $^1$H NMR (CDCl$_3$, 300 MHz): δ (ppm) 7.34-7.29 (m, 5H); 5.07 (s, 2H); 4.98-4.91 (s, 2H); 4.72 (s, 1H); 3.56 (m, 1H); 3.17-3.13 (m, 4H); 1.46-1.41 (m, 6H); 1.41 (m, 18H).

$^{13}$C NMR (CDCl$_3$, 75 MHz): δ (ppm) 176.3; 155.8 (2C); 136.0; 127.8 (2C); 127.4 (3C); 78.7 (2C); 65.9; 50.5; 43.9; 39.8; 31.6; 29.1; 27.6 (6C); 22.1.

MS (ESI+): m/z=[M+H] 466.3; [M+Na] 488.3.

HRMS (ESI+): m/z calculated for $C_{24}H_{39}N_3O_6Na$ [M+Na]=488.2737; found=488.2730.

Compounds 19 and 20:

To a solution of the compound 17 or 18 (1.1-5.7 mmol) in methanol (10-40 mL), is added Pd/C (10% m/m). The reaction medium is placed under vacuum and under stirring at room temperature for 30 min, then kept under a flow of H$_2$ for 6 h. It is then filtered over paper and the methanol is evaporated under reduced pressure in order to respectively give the derivative 19 or 20 in the form of a white powder (92 or 100%).

Compound 19: $^1$H NMR (CDCl$_3$, 600 MHz): δ (ppm) 4.98 (s, 1H); 4.96 (s, 1H); 3.56 (m, 1H); 3.18-3.12 (m, 2H); 2.74 (s, 2H); 2.74 (m, 2H); 1.48-1.43 (m, 4H); 1.41 (s, 18H).

$^{13}$C NMR (CDCl$_3$, 150 MHz): δ (ppm) 156.7; 156.3; 79.3 (2C); 51.2; 44.7; 41.6; 30.1; 29.3; 28.4 (6C).

MS (ESI+): m/z=[M+H] 318.2; [M+Na] 340.2.

HRMS (ESI+): m/z calculated for $C_{15}H_{31}N_3O_4$ [M+H]= 318.2393; found=318.2379.

Compound 20: $^1$H NMR (CDCl$_3$, 300 MHz): δ (ppm) 4.99 (s, 2H); 4.76-4.73 (s, 2H); 3.55 (m, 1H); 3.10 (m, 2H); 2.61-2.59 (m, 2H); 1.57 (m, 2H); 1.37 (m, 22H).

$^{13}$C NMR (CDCl$_3$, 75 MHz): δ (ppm) 170.8; 167.9; 78.9 (2C); 51.0; 44.4; 43.1; 33.1; 32.4; 28.0 (6C); 22.7.

MS (ESI+): m/z=[M+H] 332.2; [M+Na] 354.2.

HRMS (ESI+): m/z calculated for $C_{16}H_{33}N_3O_4$ [M+H]= 332.2549; found=332.2564.

2—Coupling of the $R_a$ or $NR'_aR_b$ Group a) Pseudo-Peptide Coupling

α—Method A (Scheme 3)

NaHCO$_3$ and saturated NaCl, dried over Na$_2$SO$_4$ and finally evaporated under reduced pressure in order to give the compound 21a-b, 22a-b, 23c-f or 23j (25 to 82%) after purification on a silica column (CH$_2$Cl$_2$/MeOH 98:2 at 95:5) (Table 2).

β—Method B (Scheme 4)

Scheme 3: Pseudo-peptide coupling of the $R'_a$ or $NR'_aR_b$ group (Method A)

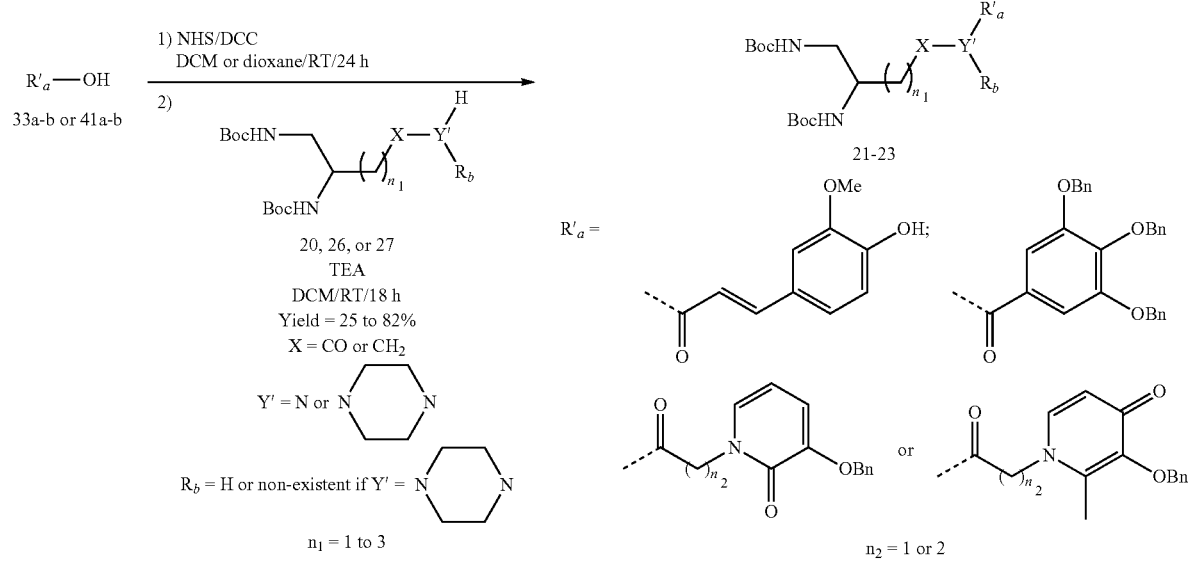

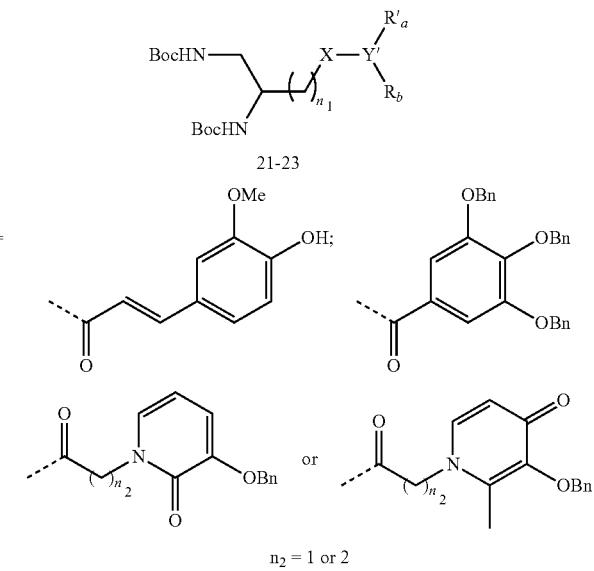

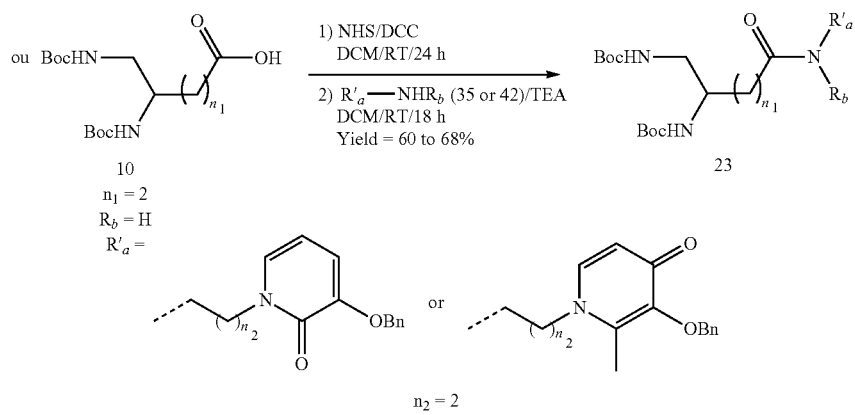

1$^{st}$ step: To a solution of the derivative 10, 33a-b, 41a-b, carrying an acid function (0.4-3.0 mmol) in dichloromethane or 1,4-dioxane (10-25 mL), are successively added N-hydroxysuccinimide (1.1 to 1.5 eq) and DCC (1 to 1.2 eq). The reaction medium is kept under stirring at room temperature for 24h, then filtered under a vacuum. The filtrate is then evaporated under reduced pressure to give the activated intermediate of the acid.

2$^{nd}$ step: The amine derivative 20, 26, 27, 35 or 42 (1 to 1.7 eq) is dissolved in dichloromethane (8-30 mL) and set to react with triethylamine (0 to 4 eq) at room temperature for 30 min. The activated intermediate of the acid (1 eq) is then introduced into the reaction medium which is then placed under stirring at room temperature for 18 h. The organic phase is then washed with a solution of HCl 1N, then Scheme 4: Pseudo-peptide coupling of the $R'_a$ group (Method B)

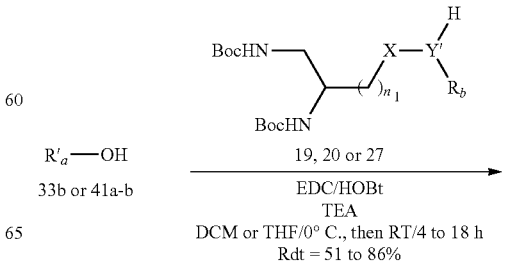

-continued

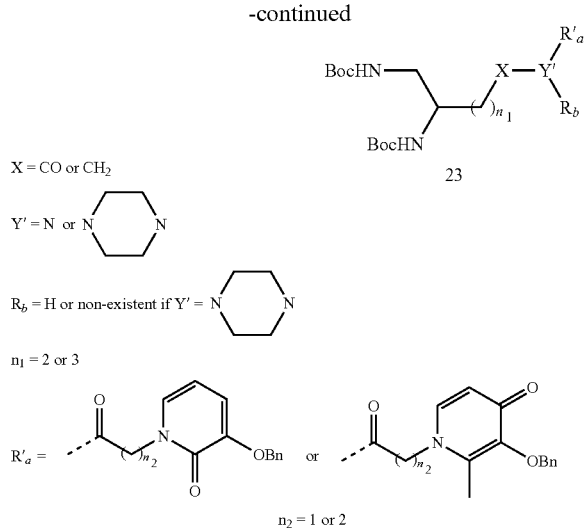

X = CO or CH$_2$

Y' = N or piperazine

R$_b$ = H or non-existent if Y' = piperazine n$_1$ = 2 or 3

R'$_a$ = pyridinone-OBn (n$_2$) or methylpyridinone-OBn (n$_2$)

n$_2$ = 1 or 2

To a solution of the derivative carrying an acid function 33b, 41a-b (1-6.5 mmol) in dichloromethane, DMF or THF (25-100 mL), placed under stirring at 0° C., are successively added 1-ethyl-3-(3-dimethylaminopropyl)-carbodiimide chlorhydrate (1.2 eq), 1-hydroxybenzotriazole monohydrate (1.1-1.2 eq). After 30 min of stirring at 0° C., the amine derivative 19, 20 or 27 (1 eq) is introduced with triethylamine (1.2 eq) in the reaction medium which is then kept under stirring at room temperature for 4 to 18 h. After evaporation of the DMF or of the THF and taking of the residue in dichloromethane, the organic phase is washed with a saturated solution of NaCl, dried over Na$_2$SO$_4$ and finally evaporated under reduced pressure in order to give after purification on a silica column (AcOEt/Cyclohexane 60:40 or AcOEt/MeOH 80:20) the compounds 23a-b, 23g-i or 23k (51 to 86%) (Table 2).

TABLE 2

Compounds 21-23

| Compound | n$_1$ | X | Y' | R'$_a$ | R$_b$ | Yield (%) (Method) | Aspect |
|---|---|---|---|---|---|---|---|
| 21a | 2 | CO | piperazine | OMe, OH substituted cinnamoyl | Non-existent | 55 (A) | White powder |
| 21b | 3 | CH$_2$ | N | OMe, OH substituted cinnamoyl | H | 71 (A) | White powder |
| 22a | 2 | CO | piperazine | 3,4,5-tri-OBn benzoyl | Non-existent | 81 (A) | Colourless oil |
| 22b | 3 | CH$_2$ | N | 3,4,5-tri-OBn benzoyl | H | 58 (A) | Yellow powder |
| 23a | 2 | CH$_2$ | N | pyridinone-OBn propanoyl | H | 92 (B) | Brown powder |

TABLE 2-continued

Compounds 21-23

| Compound | $n_1$ | X | Y' | R'$_a$ | R$_b$ | Yield (%) (Method) | Aspect |
|---|---|---|---|---|---|---|---|
| 23b | 3 | CH$_2$ | N | 3-OBn-pyridin-2(1H)-one propanoyl | H | 86 (B) | Brown powder |
| 23c | 2 | CO | N | 3-OBn-pyridin-2(1H)-one propanoyl | H | 68 (A) | White powder |
| 23d | 1 | CO | piperazine | 3-OBn-pyridin-2(1H)-one propanoyl | Non-existent | 39 (A) | Brown powder |
| 23e | 2 | CO | piperazine | 3-OBn-pyridin-2(1H)-one acetyl | Non-existent | 56 (A) | White powder |
| 23f | 2 | CO | piperazine | 3-OBn-pyridin-2(1H)-one propanoyl | Non-existent | 25 (A) | White powder |
| 23g | 2 | CH$_2$ | N | 3-OBn-2-methyl-pyridin-4(1H)-one acetyl | H | 65 (B) | White powder |
| 23h | 3 | CH$_2$ | N | 3-OBn-2-methyl-pyridin-4(1H)-one acetyl | H | 62 (B) | White powder |
| 23i | 3 | CH$_2$ | N | 3-OBn-2-methyl-pyridin-4(1H)-one propanoyl | H | 69 (B) | Pasty white solid |
| 23j | 2 | CO | N | 3-OBn-2-methyl-pyridin-4(1H)-one propyl | H | 60 (A) | Yellow powder |

TABLE 2-continued

Compounds 21-23

| Compound | $n_1$ | X | Y' | $R'_a$ | $R_b$ | Yield (%) (Method) | Aspect |
|---|---|---|---|---|---|---|---|
| 23k | 2 | CO | piperazine | pyridinone with OBn, Me, CH2C(O)– | Non-existent | 51 (B) | White powder |

Compound 21a: $^1$H NMR (CDCl$_3$, 300 MHz): δ (ppm) 7.63 (d, J=15.0 Hz, 1H); 7.09 (dd, J$_1$=8.4 Hz, J$_2$=1.8 Hz, 1H); 6.99 (d, J=1.8 Hz, 1H); 6.91 (d, J=8.1 Hz, 1H); 6.67 (d, J=15.3 Hz, 1H); 6.08 (s, 1H); 4.93 (s, 2H); 3.92 (s, 3H); 3.73-3.50 (m, 9H); 3.20 (t, J=5.4 Hz, 2H); 2.45-2.39 (m, 2H); 1.86-1.80 (m, 2H); 1.42 (s, 18H).
$^{13}$C NMR (CDCl$_3$, 75 MHz): δ (ppm) 170.8; 170.5; 165.5 (2C); 147.2; 146.4; 143.4; 127.1; 121.7; 114.4; 113.3; 109.5; 77.5 (2C); 55.6; 51.0; 44.8; 44.2 (2C); 41.3 (2C); 29.1; 27.9 (6C); 27.5.
MS (ESI+): m/z=[M+H] 577.3; [M+Na] 599.3.
HRMS (ESI+): m/z calculated for C$_{29}$H$_{44}$N$_4$O$_8$ [M+Na]=599.3057; found=599.3043.
Compound 21b: $^1$H NMR (CDCl$_3$, 300 MHz): δ (ppm) 7.52 (d, J=15.6 Hz, 1H); 7.02 (dd, J$_1$=8.1 Hz, J$_2$=1.8 Hz, 1H); 6.96 (d, J=1.8 Hz, 1H); 6.87 (d, J=8.1 Hz, 1H); 6.31 (d, J=15.6 Hz, 1H); 6.28 (s, 1H); 5.01-4.99 (s, 1H); 4.84-4.82 (s, 1H); 3.86 (s, 3H); 3.59-3.58 (m, 1H); 3.34-3.33 (m, 2H); 3.16 (m, 2H); 1.57-1.55 (m, 2H); 1.42 (m, 22H).
$^{13}$C NMR (CDCl$_3$, 75 MHz): δ (ppm) 167.4 (2C); 157.3; 148.3; 147.8; 141.6; 128.4; 122.9; 119.5; 115.8; 110.8; 80.4 (2C); 56.8; 52.2; 45.3; 39.9; 33.1; 30.6; 29.3 (6C); 23.7.
MS (ESI+): m/z=[M+H] 508.2; [M+Na] 530.2.
HRMS (ESI+): m/z calculated for C$_{26}$H$_{41}$N$_3$O$_7$Na [M+Na]=530.2842; found=530.2856.
Compound 22a: $^1$H NMR (CDCl$_3$, 300 MHz): δ (ppm) 7.40-7.33 (m, 12H); 7.28-7.26 (m, 3H); 6.65 (s, 2H); 5.12 (s, 4H); 5.10 (s, 2H); 3.65-3.19 (m, 11H); 2.42-2.39 (m, 2H); 1.90-1.84 (m, 2H); 1.70-1.64 (m, 2H); 1.43 (s, 18H).
$^{13}$C NMR (CDCl$_3$, 75 MHz): δ (ppm) 171.0; 169.9; 156.5; 156.2; 152.5 (2C); 139.7; 137.3; 136.5 (2C); 129.9; 128.4 (6C); 128.0; 127.8 (2C); 127.1 (6C); 107.1 (2C); 79.2 (2C); 75.0; 71.0 (2C); 51.2; 45.0 (2C); 44.4; 41.5 (2C); 33.7; 29.3; 28.2 (6C).
MS (ESI+): m/z=[M+H] 823.3; [M+Na] 845.3.
HRMS (ESI+): m/z calculated for C$_{47}$H$_{58}$N$_4$O$_9$Na [M+Na]=845.4101; found=845.4138.
Compound 22b: $^1$H NMR (CDCl$_3$, 300 MHz): δ (ppm) 7.38-7.28 (m, 12H); 7.28-7.26 (m, 3H); 7.17 (s, 2H); 6.62 (s, 1H); 5.13 (s, 4H); 5.09 (s, 2H); 4.97 (s, 1H); 4.78-4.75 (s, 1H); 3.63-3.62 (m, 1H); 3.40 (m, 2H); 3.20-3.18 (m, 2H); 1.62 (m, 2H); 1.46-1.44 (m, 22H).
$^{13}$C NMR (CDCl$_3$, 75 MHz): δ (ppm) 167.2; 156.2 (2C); 152.8 (2C); 141.1; 137.6; 136.9 (2C); 130.3; 128.6 (6C); 128.3; 128.1 (2C); 127.7 (6C); 107.0 (2C); 79.6 (2C); 75.3 (2C); 71.5; 51.4; 44.2; 39.5; 32.1; 29.2; 28.5 (2C); 22.8.
MS (ESI+): m/z=[M−3Bn+3H+Na] 506.3; [M+H+Na] 777.2.
HRMS (ESI+): m/z calculated for C$_{44}$H$_{55}$N$_3$O$_8$Na [M+Na]=776.3887; found=776.3905.
Compound 23a: $^1$H NMR (CDCl$_3$, 300 MHz): δ (ppm) 7.38-7.28 (m, 5H); 7.22-7.19 (s, 1H); 7.08 (dd, J$_1$=6.9 Hz, J$_2$=1.5 Hz, 1H); 6.70 (dd, J$_1$=7.5 Hz, J$_2$=1.2 Hz, 1H); 6.04 (t, J=7.2 Hz, 1H); 5.07-5.01 (s, 2H); 4.93-4.90 (s, 1H); 4.28-4.18 (m, 2H); 3.51-3.47 (m, 1H); 3.05-3.03 (m, 4H); 2.63 (t, J=6.0 Hz, 2H); 2.27-1.40 (s, 9H); 1.38 (s, 9H); 1.32-1.17 (m, 4H).
$^{13}$C NMR (CDCl$_3$, 75 MHz): δ (ppm) 169.7 (2C); 157.7; 156.1; 148.1; 135.4; 130.0; 128.1 (2C); 127.7; 127.2 (2C); 115.1; 104.4; 78.7 (2C); 70.3; 50.5; 46.5; 44.6; 38.6; 34.5; 29.4; 27.9 (6C); 25.0.
MS (ESI+): m/z=[M+H] 573.2; [M+Na] 595.1.
HRMS (ESI+): m/z calculated for C$_{30}$H$_{44}$N$_4$O$_7$Na [M+Na]=595.3108; found=595.3098.
Compound 23b: $^1$H NMR (CDCl$_3$, 300 MHz): δ (ppm) 7.36-7.25 (m, 5H); 7.06 (dd, J$_1$=6.9 Hz, J$_2$=1.5 Hz, 1H); 6.99 (s, 1H); 6.66 (dd, J$_1$=7.5 Hz, J$_2$=1.5 Hz, 1H); 6.00 (t, J=7.2 Hz, 1H); 5.00 (s, 1H); 5.00 (s, 2H); 4.83-4.80 (s, 1H); 4.21 (t, J=6.3 Hz, 2H); 3.50-3.48 (m, 1H); 3.07-3.00 (m, 4H); 2.65 (t, J=6.0 Hz, 2H); 1.38 (s, 18H); 1.33-1.23 (m, 6H).
$^{13}$C NMR (CDCl$_3$, 75 MHz): δ (ppm) 170.1 (2C); 158.1 (2C); 148.5; 135.9; 130.3; 128.5 (2C); 128.1; 127.4 (2C); 115.6; 104.7; 79.2 (2C); 70.6; 51.1; 47.0; 44.6; 38.8; 35.0; 32.0; 28.9; 28.3 (6C); 22.7.
MS (ESI+): m/z=[M+H] 587.5; [M+Na] 609.3.
HRMS (ESI+): m/z calculated for C$_{31}$H$_{46}$N$_4$O$_7$Na [M+Na]=609.3264; found=609.3254.
Compound 23c: $^1$H NMR (CDCl$_3$, 300 MHz): δ (ppm) 7.40 (s, 1H); 7.38-7.25 (m, 5H); 6.95 (d, J=6.0 Hz, 1H); 6.67 (d, J=6.8 Hz, 1H); 6.10 (t, J=7.2 Hz, 1H); 5.40-5.23 (s, 2H); 5.03 (s, 2H); 4.00 (t, J=5.1 Hz, 2H); 3.61-3.59 (m, 1H); 3.11 (m, 4H); 2.33-2.26 (m, 2H); 1.87-1.61 (m, 4H); 1.35 (s, 18H).
$^{13}$C NMR (CDCl$_3$, 75 MHz): δ (ppm) 172.3 (2C); 156.4; 156.2; 148.2; 135.6; 128.5; 128.2 (2C); 128.0; 127.8 (2C); 115.5; 105.8; 79.0 (2C); 70.4; 50.9; 46.8; 44.2; 35.7; 32.6; 30.3; 28.8; 28.0 (6C).
MS (ESI+): m/z=[M+H] 573.5; [M+Na] 595.4.
HRMS (ESI+): m/z calculated for C$_{30}$H$_{44}$N$_4$O$_7$Na [M+Na]=595.3108; found=595.3078.
Compound 23d: $^1$H NMR (CDCl$_3$, 300 MHz): δ (ppm) 7.32-7.18 (m, 5H); 7.01 (d, J=6.1 Hz, 1H); 6.56 (d, J=5.4 Hz, 1H); 5.92 (t, J=6.9 Hz, 1H); 5.62-5.60 (s, 1H); 5.03-4.97 (s, 1H); 4.97 (s, 2H); 4.14 (t, J=6.3 Hz, 2H); 3.81-3.79 (m, 1H); 3.54-3.32 (m, 8H); 3.23-3.13 (m, 2H); 2.79 (t, J=6.0 Hz, 2H); 2.57-2.38 (m, 2H); 1.30 (s, 18H). $^{13}$C NMR (CDCl$_3$, 75 MHz): δ (ppm) 168.7; 168.6; 157.8; 156.2; 155.2; 142.0; 135.6; 129.8; 128.1 (2C); 127.5; 126.8 (2C); 115.1; 104.1; 79.1 (2C); 70.2; 48.6; 46.7; 44.8 (2C); 43.1; 41.0 (2C); 34.7; 31.2; 27.9 (6C). MS (ESI+): m/z=[M+H] 642.3; [M+Na] 664.3.
HRMS (ESI+): m/z calculated for C$_{33}$H$_{47}$N$_5$O$_8$Na [M+Na]=664.3322; found=664.3322.
Compound 23e: $^1$H NMR (CDCl$_3$, 400 MHz): δ (ppm) 7.38 (d, J=7.1 Hz, 2H); 7.32 (t, J=7.5 Hz, 2H); 7.26 (t, J=7.8 Hz, 1H); 7.27 (m, 1H); 6.65 (d, J=7.5 Hz, 1H); 6.05 (t, J=7.0

Hz, 1H); 5.06 (s, 2H); 5.04-5.02 (s, 2H); 4.76-4.69 (m, 2H); 3.75-3.41 (m, 9H); 3.17-3.14 (m, 2H); 2.40-2.34 (m, 2H); 1.85-1.63 (m, 2H); 1.39 (s, 18H).

$^{13}$C NMR (CDCl$_3$, 100 MHz): δ (ppm) 171.3; 165.6 (2C); 158.0; 156.1; 148.3; 135.9; 129.6; 128.5 (2C); 127.9; 127.2 (2C); 115.9; 104.8; 79.3 (2C); 70.7; 51.4; 49.2; 45.2; 44.8; 44.4; 42.0; 41.4; 29.7; 28.3 (6C); 27.8.

MS (ESI+): m/z=[M−Boc+2H] 542.3; [M+H] 642.3; [M+Na] 664.3.

HRMS (ESI+): m/z calculated for C$_{33}$H$_{47}$N$_5$O$_8$Na [M+Na]=664.3322; found=664.3324.

Compound 23f: $^1$H NMR (CDCl$_3$, 300 MHz): δ (ppm) 7.42 (d, J=6.6 Hz, 2H); 7.37-7.28 (m, 3H); 7.11 (d, J=5.9 Hz, 1H); 6.65 (d, J=6.2 Hz, 1H); 6.02 (t, J=7.2 Hz, 1H); 5.08 (s, 2H); 4.94-4.93 (s, 2H); 4.24 (t, J=6.3 Hz, 2H); 3.54-3.32 (m, 9H); 3.17 (t, J=5.4 Hz, 2H); 2.89 (t, J=6.3 Hz, 2H); 2.41-2.34 (m, 2H); 1.94-1.82 (m, 2H); 1.40 (s, 18H).

$^{13}$C NMR (CDCl$_3$, 75 MHz): δ (ppm) 171.4 (2C); 158.6; 156.7; 149.1; 140.1; 138.2; 130.7; 128.9 (2C); 128.4; 127.7 (2C); 115.9; 104.9; 87.1; 87.0; 71.1; 51.8; 47.6; 45.9 (2C); 45.0; 41.9 (2C); 32.0; 30.1; 28.7 (6C); 28.3.

MS (ESI+): m/z=[M+H] 656.3; [M+Na] 678.3.

HRMS (ESI+): m/z calculated for C$_{34}$H$_{49}$N$_5$O$_8$Na [M+Na]=678.3479; found=678.3474.

Compound 23g: $^1$H NMR (CD$_3$OD, 300 MHz): δ (ppm) 7.61 (d, J=7.5 Hz, 1H); 7.41-7.31 (m, 5H); 6.46 (d, J=7.5 Hz, 1H); 5.05 (s, 2H); 4.68 (s, 2H); 3.58-3.54 (m, 1H); 3.23-3.18 (m, 2H); 3.12-2.97 (m, 2H); 2.07 (s, 3H); 1.58-1.30 (m, 22H).

$^{13}$C NMR (CD$_3$OD, 75 MHz): δ (ppm) 175.6; 168.5; 163.7; 158.7; 147.3; 145.9; 143.0; 138.8; 130.4 (2C); 129.8 (2C); 129.6; 117.4; 80.4; 80.3; 75.0; 57.2; 52.2; 45.8; 40.9; 31.2; 29.1 (6C); 27.2; 13.3.

MS (ESI+): m/z=[M+Na] 595.3.

HRMS (ESI+): m/z calculated for C$_{30}$H$_{44}$N$_4$O$_7$Na [M+Na]=595.3108; found=595.3121.

Compound 23h: $^1$H NMR (CD$_3$OD, 300 MHz): δ (ppm) 7.62 (d, J=7.2 Hz, 1H); 7.42-7.32 (m, 5H); 6.47 (d, J=7.2 Hz, 1H); 5.06 (s, 2H); 4.68 (s, 2H); 3.56-3.54 (m, 1H); 3.23-3.18 (m, 2H); 3.14-2.98 (m, 2H); 2.08 (s, 3H); 1.49-1.35 (m, 24H).

$^{13}$C NMR (CD$_3$OD, 75 MHz): δ (ppm) 175.3; 168.2; 161.1; 158.7; 147.0; 145.6; 142.7; 138.5; 130.2 (2C); 129.5 (2C); 129.3; 117.1; 80.1; 80.0; 74.7; 56.9; 52.1; 45.5; 40.6; 33.1; 30.1; 28.9 (6C); 24.4; 13.0.

MS (ESI+): m/z=[M+Na] 609.3.

HRMS (ESI+): m/z calculated for C$_{31}$H$_{46}$N$_4$O$_7$Na [M+Na]=609.3264; found=609.3271.

Compound 23i: $^1$H NMR (CDCl$_3$, 400 MHz): δ (ppm) 7.70 (s, 1H); 7.37-7.30 (m, 6H); 6.28 (d, J=5.6 Hz, 1H); 5.40 (s, 1H); 5.18 (s, 1H); 5.06 (s, 2H); 4.10-4.06 (m, 2H); 3.51-3.49 (m, 1H); 3.24-3.04 (m, 4H); 2.65-2.50 (m, 4H); 2.12 (s, 3H); 1.44-1.37 (m, 4H); 1.37 (s, 18H).

$^{13}$C NMR (CDCl$_3$, 75 MHz): δ (ppm) 173.6; 169.1; 157.0; 156.4; 145.8; 141.6; 139.2; 137.2; 128.9; 128.4 (2C); 128.3 (2C); 116.9; 79.2 (2C); 72.9; 52.3; 50.1; 44.4; 39.1; 36.2; 35.0; 31.9; 28.4 (6C); 22.7; 12.4.

MS (ESI+): m/z=[M+H] 601.3; [M+Na] 623.3.

HRMS (ESI+): m/z calculated for C$_{32}$H$_{49}$N$_4$O$_7$ [M+H]= 601.3601; found=601.3621.

Compound 23j: $^1$H NMR (CDCl$_3$, 300 MHz): δ (ppm) 7.58-7.55 (s, 1H); 7.37-7.24 (m, 6H); 6.32 (d, J=5.6 Hz, 1H); 5.47-5.45 (s, 2H); 5.08 (s, 2H); 3.80-3.77 (m, 2H); 3.54-3.53 (m, 1H); 3.24-3.10 (m, 4H); 2.22 (t, J=4.9 Hz, 2H); 2.03 (s, 3H); 1.93-1.70 (m, 4H); 1.36 (s, 18H).

$^{13}$C NMR (CDCl$_3$, 75 MHz): δ (ppm) 173.8; 173.3; 156.9 (2C); 146.3; 141.4; 139.0; 137.4; 129.0 (2C); 128.4 (2C); 128.2; 117.1; 79.6 (2C); 73.1; 51.9; 51.3; 44.4; 36.2; 32.9; 30.7; 29.2; 28.4 (6C), 12.4.

MS (ESI+): m/z=[M+H] 587.3; [M+Na] 609.3.

HRMS (ESI+): m/z calculated for C$_{31}$H$_{46}$N$_4$O$_7$Na [M+Na]=609.3264; found=609.3265.

Compound 23k: $^1$H NMR (CDCl$_3$, 400 MHz): δ (ppm) 7.35-7.28 (m, 6H); 6.42 (d, J=7.2 Hz, 1H); 5.17 (s, 2H); 5.03 (s, 2H); 4.83 (m, 2H); 3.60-3.42 (m, 9H); 3.19 (m, 2H); 2.43-2.37 (m, 2H); 2.04 (s, 3H); 1.88-1.67 (m, 2H); 1.43 (s, 18H).

$^{13}$C NMR (CDCl$_3$, 100 MHz): δ (ppm) 173.1; 171.4; 164.5; 157.0; 156.3; 145.6; 144.1; 140.8; 137.6; 129.0 (2C); 128.7 (2C); 128.4; 116.3; 79.6 (2C); 73.8; 55.3; 51.6; 45.1; 44.7; 42.5; 41.7; 41.4; 29.7; 28.6 (6C); 28.0; 13.0.

MS (ESI+): m/z=[M+H] 656.4; [M+Na] 678.3.

HRMS (ESI+): m/z calculated for C$_{34}$H$_{49}$N$_5$O$_8$Na [M+Na]=678.3479; found=678.3464.

γ—Coupling of the Synthons Coming from Aspartic and Glutamic Acids with the Piperazine (Scheme 5)

Scheme 5: Coupling of derivatives of aspartic and glutamic acids with the piperazine

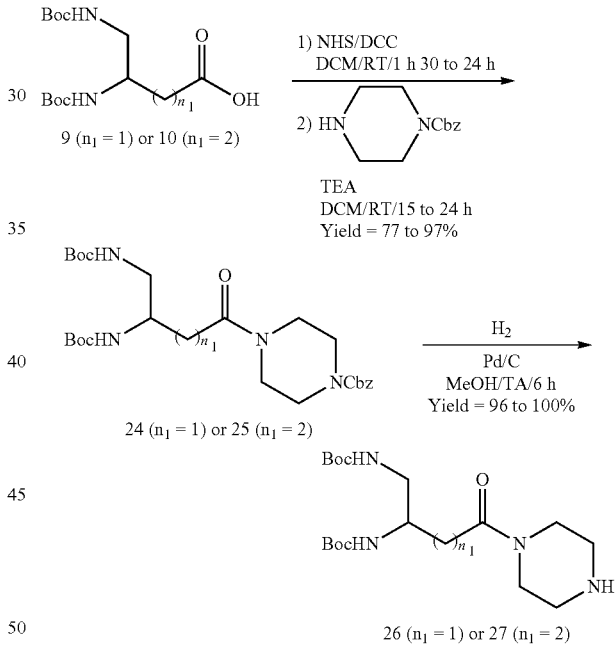

The benzyl piperazine-1-carboxylate was synthesised by adapting a method developed by Dener et al (WO 1998/04537 A1) by way of t-butyl 4-benzyloxycarbonylpiperazine-1-carboxylate. As such, the t-butyl piperazine-1-carboxylate is obtained according to a procedure described by Moussa et al. (*J. Med. Chem.*, 2010, 53, 6228-6239). Then, it is set to react (18.8 mmol) with triethylamine (1.2 eq) in dichloromethane (50 mL) at 0° C. for 10 min. A solution of benzyl chloroformate (1.2 eq) in dichloromethane (30 mL) is then introduced into the medium which is placed under stirring at room temperature for 18 h. The dichloromethane is then evaporated under reduced pressure and the residue is taken in ethyl acetate. The organic phase is finally washed with a solution of KHSO$_4$ 1M and of NaHCO$_3$ 5%, then a saturated solution of NaCl, dried over Na$_2$SO$_4$ and finally evaporated under reduced pressure in order to give the t-butyl 4-benzyloxycarbonylpiperazine-1-carboxylate in the form of a white powder (87%) after purification on a silica column (CH$_2$Cl$_2$/MeOH 99:1). This intermediate (10.9 mmol) is finally dissolved in 1,4-dioxane (15 mL) in the presence of an off-the-shelf solution of HCl 4N in 1,4-dioxane (20 eq). The reaction medium is then placed under stirring at room temperature for 45 min. The 1,4-dioxane is evaporated under reduced pressure and the residue is crushed in ether in order to give benzyl piperazine-1-carboxylate in the form of a white powder (92%), after filtration under a vacuum.

Compounds 24 and 25:

1$^{st}$ step: To a solution of the compound 9 or 10 (3.1-4.5 mmol) in dichloromethane (25-30 mL), are successively added N-hydroxysuccinimide (1.2-1.5 eq) and DCC (1.1-1.2 eq). The reaction medium is kept under stirring at room temperature for 1 h30 to 24 h, then filtered under a vacuum. The filtrate is then evaporated under reduced pressure to give the activated intermediate of the acid.

2$^{nd}$ step: The benzyl piperazine-1-carboxylate (1.2 eq) is dissolved in dichloromethane (40 mL) and set to react with triethylamine (3 eq) at room temperature for 30 min. The activated intermediate of the acid (1 eq) is then introduced into the reaction medium which is then placed under stirring at room temperature for 15 to 24 h. The organic phase is then washed with a solution of HCl 1N, then a saturated solution of NaHCO$_3$ and of NaCl, dried over Na$_2$SO$_4$ and finally evaporated under reduced pressure in order to give the compound 24 or 25 in the form of a white powder (77 or 97%) after purification on a silica column (CH$_2$Cl$_2$/MeOH 98:2).

Compound 24: $^1$H NMR (CDCl$_3$, 300 MHz): δ (ppm) 7.33 (m, 5H); 5.69 (s, 1H); 5.12 (s, 2H); 5.03 (s, 1H); 3.89 (m, 1H); 3.62-3.45 (m, 10H); 2.65-2.41 (m, 2H); 1.40 (s, 18H).

$^{13}$C NMR (CDCl$_3$, 75 MHz): δ (ppm) 173.0; 163.7; 161.1; 147.7; 132.4; 128.9 (2C); 128.5; 128.3 (2C); 81.2 (2C); 67.8; 49.7; 45.9; 44.1 (2C); 41.8 (2C); 35.3; 28.7 (6C).

MS (ESI+): m/z=[M+H] 521.3; [M+Na] 543.2.

HRMS (ESI+): m/z calculated for C$_{26}$H$_{40}$N$_4$O$_7$Na [M+Na]=543.2795; found=543.2794.

Compound 25: $^1$H NMR (CDCl$_3$, 300 MHz): δ (ppm) 7.36-7.32 (m, 5H); 5.13 (s, 2H); 4.92 (s, 2H); 3.60-3.44 (m, 9H); 3.20-3.16 (m, 2H); 2.41-2.38 (m, 2H); 1.83-1.81 (m, 2H); 1.40 (s, 18H).

$^{13}$C NMR (CDCl$_3$, 75 MHz): δ (ppm) 170.8; 164.1; 163.8; 154.7; 136.0; 128.2 (2C); 127.8; 127.6 (2C); 79.0 (2C); 67.1; 51.1; 44.8 (2C); 44.3; 43.4; 41.1 (2C); 29.2; 28.0 (6C); 27.5.

MS (ESI+): m/z=[M+H] 535.3; [M+Na] 557.3.

HRMS (ESI+): m/z calculated for C$_{27}$H$_{42}$N$_4$O$_7$Na [M+Na]=557.2951; found=557.2945.

Compounds 26 and 27:

To a solution of the compound 24 or 25 (0.7-2.7 mmol) in methanol (8-30 mL), is added Pd/C (10% m/m). The reaction medium is placed under vacuum and under stirring at room temperature for 30 min, then kept under a flow of H$_2$ for 6 h. It is then filtered over paper and the methanol is evaporated under reduced pressure in order to respectively give the derivative 26 or 27 in the form of a white powder (100 or 96%).

Compound 26: $^1$H NMR (CDCl$_3$, 300 MHz): δ (ppm) 7.33 (s, 1H); 5.69-5.66 (s, 1H); 5.12 (s, 1H); 3.89-3.88 (m, 1H); 3.66-3.23 (m, 8H); 2.93-2.83 (m, 2H); 2.67-2.43 (m, 2H); 1.41 (s, 18H).

$^{13}$C NMR (CDCl$_3$, 75 MHz): δ (ppm) 167.1; 157.5; 155.4; 79.1 (2C); 48.6; 45.0; 44.6; 43.1; 40.9; 34.8; 27.9 (6C).

MS (ESI+): m/z=[M+H] 387.3; [M+Na] 409.3.

HRMS (ESI+): m/z calculated for C$_{18}$H$_{34}$N$_4$O$_5$Na [M+Na]=409.2427; found=409.2418.

Compound 27: $^1$H NMR (CDCl$_3$, 300 MHz): δ (ppm) 5.13-5.09 (s, 2H); 3.56-3.52 (m, 3H); 3.39-3.36 (m, 2H); 3.15-3.12 (m, 2H); 2.80-2.76 (m, 4H); 2.37-2.31 (m, 2H); 1.81-1.63 (m, 2H); 1.37 (s, 18H).

$^{13}$C NMR (CDCl$_3$, 75 MHz): δ (ppm) 170.8; 156.5; 156.2; 80.3; 79.1; 51.3; 46.0; 45.3; 44.5; 42.6; 41.5; 29.4; 28.2 (6C); 27.7.

MS (ESI+): m/z=[M+H] 401.4; [M+Na] 423.3.

HRMS (ESI+): m/z calculated for C$_{19}$H$_{36}$N$_4$O$_5$Na [M+Na]=423.2583; found=423.2573.

b) Compounds Carrying a Group Derived from Ferulic Acid or from Gallic Acid

α—Preparation of the Synthon R'$_a$—OH Coming from Gallic Acid

The triple O-benzylation of the phenolic groups from gallic acid is described in literature (*Carbohydr. Res.*, 2007, 342, 1510-1513).

β—Debenzylation of the R'$_a$ Group Coming from Gallic Acid (Scheme 6)

Scheme 6: Debenzylation of the R'$_a$ group coming from gallic acid

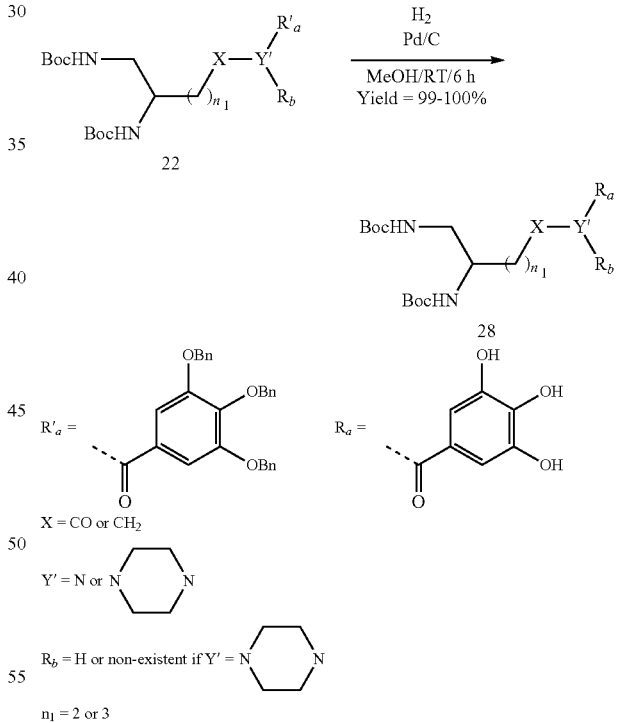

To a suspension of the compound 22a or 22b (0.5 mmol) in methanol (20 mL), is added Pd/C (10% m/m). The reaction medium is placed under vacuum and under stirring at room temperature for 30 min, then kept under a flow of H$_2$ for 6 h. It is then filtered over paper and the methanol is evaporated under reduced pressure in order to respectively give the derivative 28a or 28b (soluble in methanol, contrary to the starting product) in the form of a white powder or of an orange oil (99 or 100%).

Compound 28a: ¹H NMR (CD$_3$OD, 400 MHz): δ (ppm) 6.45 (s, 2H); 3.59-3.43 (m, 8H); 3.32-3.31 (m, 1H); 3.06-3.01 (m, 2H); 2.47-2.45 (m, 2H); 2.01-1.70 (m, 2H); 1.43 (s, 18H).

¹³C NMR (CD$_3$OD, 100 MHz): δ (ppm) 172.4; 171.9; 157.3 (2C); 157.0; 145.8 (2C); 135.3; 125.0; 106.3 (2C); 78.7 (2C); 50.5; 45.1 (2C); 43.8; 42.3 (2C); 33.5; 29.1; 27.4 (6C).

MS (ESI+): m/z=[M+H] 553.1; [M+Na] 575.1.

HRMS (ESI+): m/z calculated for C$_{26}$H$_{40}$N$_4$O$_9$Na [M+Na]=575.2693; found=575.2719.

Compound 28b: ¹H NMR (CDCl$_3$, 300 MHz): δ (ppm) 7.25 (s, 3H); 6.84 (s, 2H); 5.43 (s, 1H); 5.24-5.21 (s, 2H); 3.15-3.04 (m, 5H); 1.41-1.35 (m, 22H); 1.20-1.16 (m, 2H).

¹³C NMR (CDCl$_3$, 75 MHz): δ (ppm) 168.4; 156.7; 156.4; 144.3 (2C); 135.7; 124.6; 106.9 (2C); 79.1 (2C); 50.7; 44.2; 39.5; 31.9; 29.2; 27.9 (6C); 22.6.

MS (ESI+): m/z=[M+H] 484.2; [M+Na] 506.3.

HRMS (ESI+): m/z calculated for C$_{23}$H$_{37}$N$_3$O$_8$Na [M+Na]=506.2478; found=506.2501.

γ—Final Deprotection of the Diamine Group (Scheme 7)

Scheme 7: Final deprotection of the diamine group

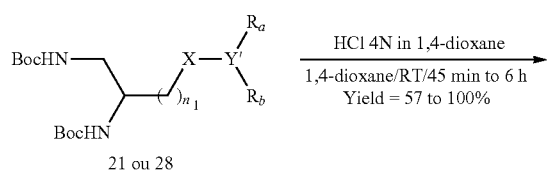

21 ou 28

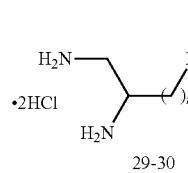

29-30

X = CO or CH$_2$

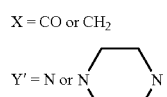

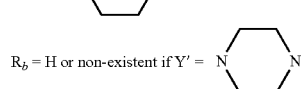

n$_1$ = 2 or 3

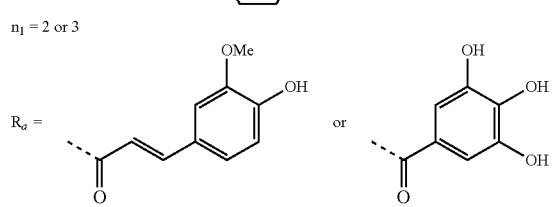

The compound 21a, 21b, 28a or 28b (0.3-0.4 mmol) is dissolved in 1,4-dioxane (7-12 mL) in the presence of an off-the-shelf solution of HCl 4N in 1,4-dioxane (20 eq). The reaction medium is then placed under stirring at room temperature for 45 min at 6 h. The 1,4-dioxane is evaporated under reduced pressure and the residue is crushed in ether. After evaporation under a vacuum (highly hygroscopic products), the precipitate obtained is lyophilised in order to respectively give the derivative 29a, 29b, 30a or 30b in the form of a yellow or beige powder (75, 66, 100 or 57%).

Compound 29a: ¹H NMR (d$_6$-DMSO, 300 MHz): δ (ppm) 9.52 (s, 1H); 8.57 (s, 2H); 8.46 (s, 2H); 7.44 (d, J=15.0 Hz, 1H); 7.33 (s, 1H); 7.10 (m, 2H); 6.79 (d, J=8.4 Hz, 1H); 3.83 (s, 3H); 3.71-3.45 (m, 9H); 3.12 (m, 2H); 2.60-2.58 (m, 2H); 1.89 (m, 2H).

¹³C NMR (d$_6$-DMSO, 75 MHz): δ (ppm) 169.7; 165.0; 162.9; 148.5; 142.4; 126.4; 122.5; 115.3; 114.2; 111.2; 55.7; 48.7; 39.7 (5C); 28.1; 25.3.

MS (ESI+): m/z=[M+H] 377.2.

HRMS (ESI+): m/z calculated for C$_{19}$H$_{29}$N$_4$O$_4$ [M+H]=377.2189; found=377.2198.

Compound 29b: ¹H NMR (d$_6$-DMSO, 300 MHz): δ (ppm) 8.49 (s, 4H); 8.11-8.09 (s, 1H); 7.30 (d, J=15.9 Hz, 1H); 7.11 (d, J=1.8 Hz, 1H); 6.97 (dd, J$_1$=8.4 Hz and J$_2$=1.8 Hz, 1H); 6.79 (d, J=8.1 Hz, 1H); 6.49 (d, J=15.9 Hz, 1H); 3.78 (s, 3H); 3.42-3.39 (m, 1H); 3.17-3.05 (m, 4H); 1.64-1.62 (m, 2H); 1.46-1.40 (m, 4H).

¹³C NMR (d$_6$-DMSO, 75 MHz): δ (ppm) 165.3; 148.2; 147.7; 138.7; 126.3; 121.4; 119.0; 115.6; 110.7; 55.4; 48.9; 38.1 (2C); 29.5; 28.6; 21.7.

MS (ESI+): m/z=[M+H] 308.1.

HRMS (ESI+): m/z calculated for C$_{16}$H$_{26}$N$_3$O$_3$ [M+H]=308.1974; found=308.1986.

Compound 30a: ¹H NMR (d$_6$-DMSO, 300 MHz): δ (ppm) 8.65 (s, 2H); 8.55 (s, 2H); 6.37 (s, 2H); 3.49-3.48 (m, 9H); 3.13 (m, 2H); 2.59 (t, J=4.8 Hz, 2H); 1.90-1.88 (m, 2H).

¹³C NMR (d$_6$-DMSO, 75 MHz): δ (ppm) 169.5; 169.3; 145.3 (2C); 134.5; 124.9; 106.3 (2C); 48.5; 40.0 (2C); 39.7; 38.3; 27.8; 25.0.

MS (ESI+): m/z=[M+H] 352.9.

HRMS (ESI+): m/z calculated for C$_{16}$H$_{25}$N$_4$O$_5$ [M+H]=353.1825; found=353.1813.

Compound 30b: ¹H NMR (d$_6$-DMSO, 300 MHz): δ (ppm) 8.47 (s, 4H); 8.11 (s, 1H); 6.82 (s, 2H); 3.24-3.07 (m, 5H); 1.65-1.35 (m, 6H).

¹³C NMR (d$_6$-DMSO, 75 MHz): δ (ppm) 166.5; 145.4; 136.1; 125.0; 106.8 (2C); 49.0; 40.4 (2C); 29.6; 28.8; 21.8.

MS (ESI+): m/z=[M+H] 284.2.

HRMS (ESI+): m/z calculated for C$_{13}$H$_{22}$N$_3$O$_4$ [M+H]=284.1610; found=284.1612.

c) Compounds Carrying a Hydroxypyridinone Group[22]

α—Preparation of the Synthons R'$_a$—OH and R'$_a$—NHR$_b$

Preparation of the Synthons R'$_a$—OH and R'$_a$—NHR$_b$ of the 3-benzyloxypyridin-2-one Type (Scheme 7):

Scheme 7: Preparation of the synthons R'$_a$—OH and R'$_a$—NHR$_b$ of the 3-benzyloxypyridine-2-one type

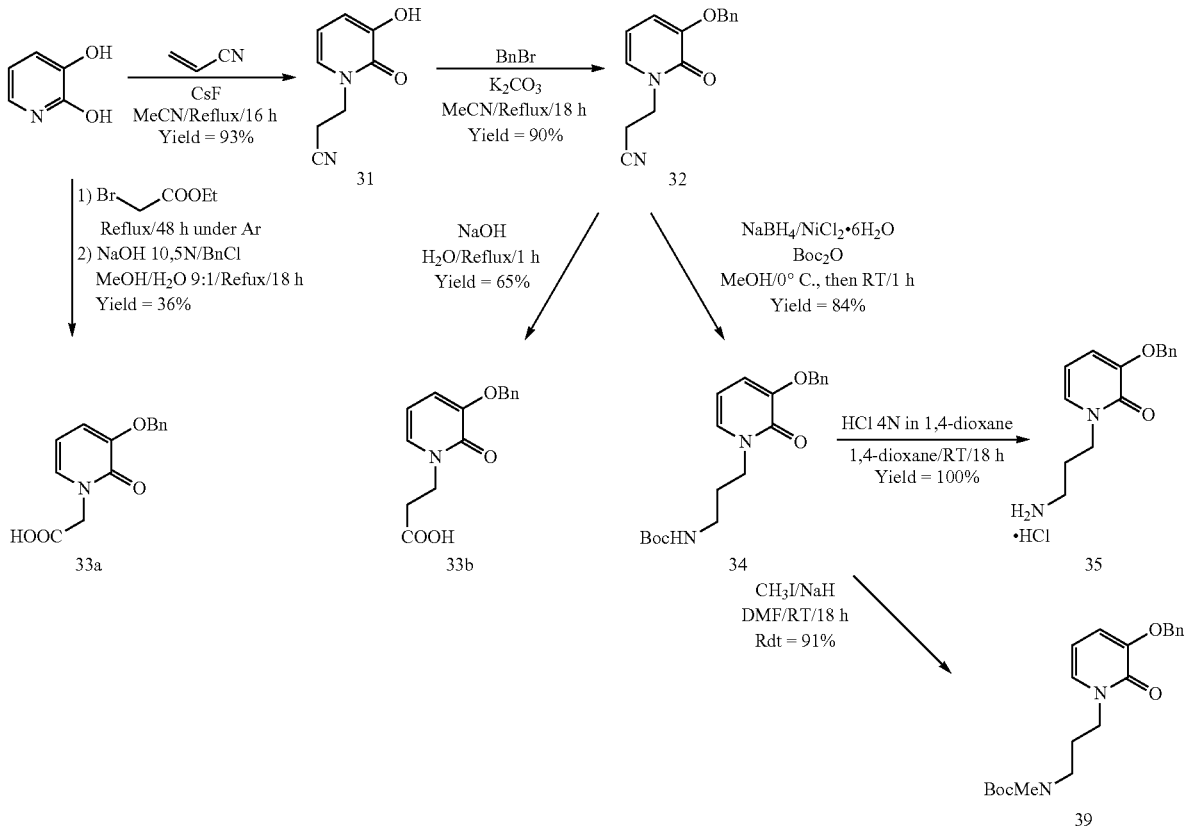

Compound 31 (Synthesis, 2011, 57-64):

To a solution of 2,3-dihydroxypyridine (135 mmol) in acetonitrile (120 mL), are added cesium fluoride (0.1 eq) and acrylonitrile (3 eq) (Tetrahedron Lett., 2002, 43, 7379-7383; Synthesis, 2011, 57-64). The reaction medium is heated under reflux for 16 h. The acetonitrile is then evaporated under reduced pressure and the desired product is extracted using ethyl acetate. The organic phase is washed with a solution of Na$_2$CO$_3$ 10%, then a saturated solution of NaCl, dried over Na$_2$SO$_4$ and finally evaporated under reduced pressure in order to give the derivative 31 in the form of a white powder (93%) after recrystallisation in a AcOEt/Cyclohexane 50:50 mixture.

Compound 32 (Synthesis, 2011, 57-64):

The derivative 32 was prepared according to the synthesis described by Arumugam et al. (*Synthesis*, 2011, 57-64) in 2011.

Compound 33a (J. Med. Chem., 1990, 33, 1749-1755; Molecules, 2015, 20, 19393-19405):

1$^{st}$ step: 2,3-dihydroxypyridine (50 mmol) is added to ethyl bromoacetate (5 eq). The reaction medium is then heated under reflux for 48 h under Ar and the desired product is finally obtained after precipitation in ethyl acetate and filtration under vacuum.

2$^{nd}$ step: To a solution of this intermediate (18 mmol) in a MeOH/H$_2$O 9:1 mixture (150 mL), is added a solution of NaOH 10.5N (2 eq). The reaction medium is then heated under reflux for 30 min. Benzyl chloride (2 eq) is then introduced dropwise over a period of 30 min at room temperature and the mixture is again heated under reflux for 18 h. After filtration under vacuum and evaporation of the methanol under reduced pressure, the aqueous phase is extracted using dichloromethane, then acidified using HCl 6N. The desired product is finally extracted using dichloromethane. The organic phase is washed with a saturated solution of NaCl, dried over Na$_2$SO$_4$ and evaporated under reduced pressure in order to give the derivative 33a in the form of a white powder (36%).

Compound 33b:

To a solution of the compound 32 (1 eq) in water (20 mL/mmol), is added sodium hydroxide (12.5 eq). The reaction medium is then heated under reflux for 1 h, then extracted using ethyl acetate in order to eliminate the remaining raw material. The aqueous phase is then acidified using a solution of HCl 6N and the desired compound is extracted using ethyl acetate. The organic phase is washed using a solution of saturated NaCl, dried over Na$_2$SO$_4$ and finally evaporated under reduced pressure in order to give the derivative 33 in the form of a yellowish powder (65%).

Compound 33b: $^1$H NMR (CDCl$_3$, 300 MHz): δ (ppm) 7.43-7.32 (m, 5H); 7.25 (dd, J$_1$=6.9 Hz and J$_2$=1.5 Hz, 1H); 6.87 (dd, J$_1$=7.3 Hz and J$_2$=1.8 Hz, 1H); 6.09 (t, J=7.2 Hz, 1H); 4.99 (s, 2H); 4.07 (t, J=6.9 Hz, 2H); 2.65 (t, J=6.9 Hz, 2H).

$^{13}$C NMR (CDCl$_3$, 75 MHz): δ (ppm) 171.9; 156.5; 147.5; 136.2; 130.1; 128.0 (2C); 127.5; 127.4 (2C); 115.1; 103.4; 69.4; 45.0; 32.5.

MS (ESI+): m/z=[M+H] 273.8.

HRMS (ESI+): m/z calculated for C$_{15}$H$_{15}$NO$_4$Na [M+Na]= 296.0899; found=296.0893.

Compound 34:

To a solution of the compound 32 (7.9 mmol) in methanol (80 mL), placed under stirring at 0° C., are added di-t-butyl dicarbonate (2 eq) and $NiCl_2.6H_2O$ (0.1 eq). Sodium borohydride (7 eq) is then introduced in small portions over a period of 30 min and the mixture is placed under stirring at room temperature for 1 h. After the adding of diethylenetriamine (1 eq) and stirring again for 1 h, the methanol is evaporated under reduced pressure and the desired product is extracted using ethyl acetate. The organic phase is washed with a saturated solution of $NaHCO_3$, then NaCl, dried over $Na_2SO_4$ and finally evaporated under reduced pressure in order to give the derivative 34 in the form of a whitish powder (84%).

Compound 34: $^1$H NMR ($CDCl_3$, 400 MHz): δ (ppm) 7.33 (d, J=7.6 Hz, 2H); 7.25 (t, J=6.8 Hz, 2H); 7.19 (t, J=6.8 Hz, 1H); 6.80 (d, J=6.3 Hz, 1H); 6.55 (d, J=7.4 Hz, 1H); 5.96 (t, J=7.3 Hz, 1H); 5.49 (s, 1H); 5.01 (s, 2H); 3.95 (t, J=6.3 Hz, 2H); 3.01-2.96 (m, 2H); 1.81-1.75 (m, 2H); 1.33 (s, 9H).

$^{13}$C NMR ($CDCl_3$, 100 MHz): δ (ppm) 158.3; 155.9; 148.5; 135.8; 128.4; 128.3 (2C); 127.8; 127.1 (2C); 115.1; 105.2; 78.6; 70.5; 46.0; 36.3; 29.7; 28.3 (3C).

MS (ESI+): m/z=[M+H] 358.9; [M+Na] 380.9.

HRMS (ESI+): m/z calculated for $C_{20}H_{26}N_2O_4Na$ [M+Na]=381.1790; found=381.1782.

Compound 35:

The compound 34 (2.4 mmol) is dissolved in 1,4-dioxane (10 mL) in the presence of an off-the-shelf solution of HCl 4N in 1,4-dioxane (20 eq). The reaction medium is then placed under stirring at room temperature for 18 h. The 1,4-dioxane is evaporated under reduced pressure and the residue is crushed in ether in order to give the derivative 35 in the form of a beige powder (100%), after filtration under a vacuum.

Compound 35: $^1$H NMR ($d_6$-DMSO, 300 MHz): δ (ppm) 8.06-8.05 (s, 2H); 7.45-7.33 (m, 6H); 6.93 (d, J=7.5 Hz, 1H); 6.18 (t, J=7.2 Hz, 1H); 5.01 (s, 2H); 4.00 (t, J=6.9 Hz, 2H); 2.75 (t, J=7.2 Hz, 2H); 1.98-1.93 (m, 2H).

$^{13}$C NMR ($d_6$-DMSO, 75 MHz): δ (ppm) 175.1; 147.6; 136.1; 129.5; 128.0 (2C); 127.5 (3C); 115.3; 104.1; 69.4; 45.4; 35.9; 26.5.

MS (ESI+): m/z=[M+H] 259.1; [M+H+MeCN] 300.2.

HRMS (ESI+): m/z calculated for $C_{15}H_{19}N_2O_2$ [M+H]= 259.1436; found=259.1447.

Compound 39:

To a solution of the compound 34 (1.5 mmol) in DMF (3 mL), is added sodium hydride (1.4 eq). After 10 min of stirring at room temperature, methyl iodine (1.2 eq) is introduced and the mixture is placed under stirring at room temperature for 18 h (Org. Lett., 2014, 16, 3196-3199). After evaporation of the DMF under reduced pressure, the residue is taken in ethyl acetate. The organic phase is washed with a saturated solution of NaCl, dried over $Na_2SO_4$ and finally evaporated under reduced pressure in order to give the derivative 39 in the form of a yellow oil (91%) after purification on a silica column (AcOEt/MeOH 50:50).

Compound 39: $^1$H NMR ($CDCl_3$, 400 MHz): δ (ppm) 7.40 (d, J=8.0 Hz, 2H); 7.31 (t, J=8.5 Hz, 2H); 7.26 (t, J=7.2 Hz, 1H); 6.93-6.86 (m, 1H); 6.61 (d, $J_1$=7.4 Hz and $J_2$=1.6 Hz, 1H); 5.99 (t, J=7.1 Hz, 1H); 5.07 (s, 2H); 3.92 (t, J=7.2 Hz, 2H); 3.27 (m, 2H); 2.82 (s, 3H); 1.96 (t, J=7.2 Hz, 2H); 1.41 (s, 9H).

$^{13}$C NMR ($CDCl_3$, 100 MHz): δ (ppm) 158.2; 149.0; 136.4; 128.6 (2C); 128.0; 127.4 (2C); 115.5; 104.8; 79.6; 70.8; 47.8; 45.8; 34.1; 28.5 (3C); 27.1.

MS (ESI+): m/z=[M+H] 373.2; [M+Na] 395.2.

HRMS (ESI+): m/z calculated for $C_{21}H_{29}N_2O_4$ [M+H]= 373.2127; found=373.2137.

Preparation of the Synthons R'$_a$—OH and R'$_a$—NHR$_b$ of the 3-benzyloxy-2-methylpyridin-4-one Type (Scheme 8):

Scheme 8: Preparation of the synthons R'$_a$—OH and R'$_a$—NHR$_b$ of the 3-benzyloxy-2-methylpyridin-4-one type

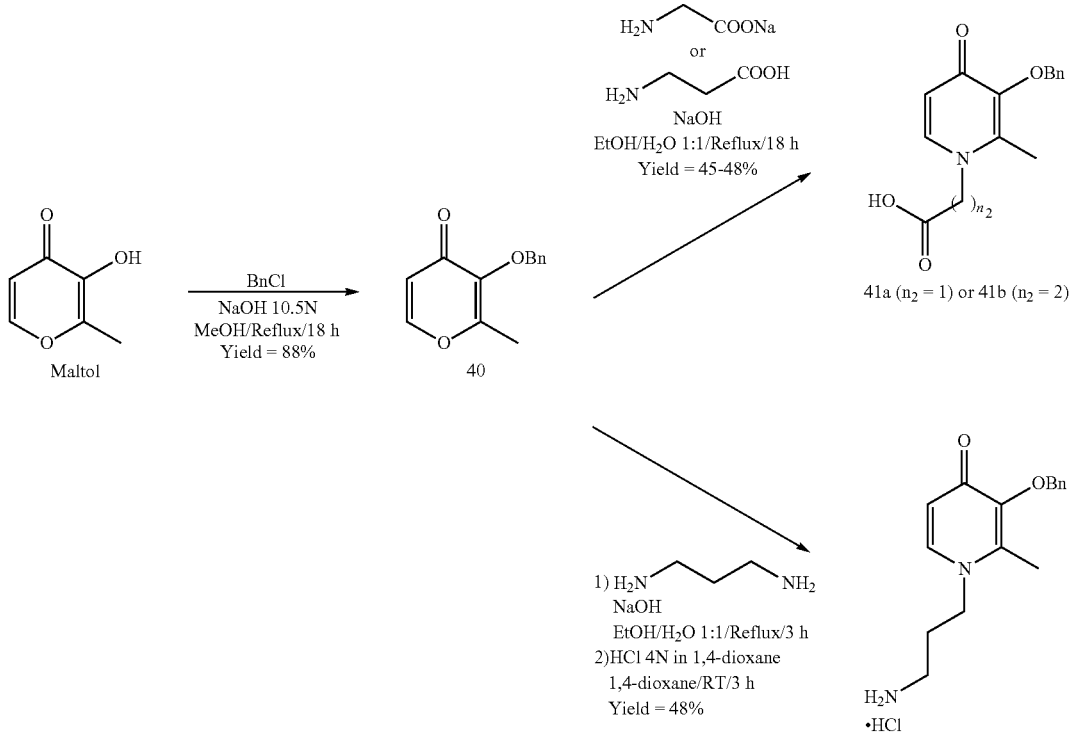

Compound 40 (J. Med. Chem., 1998, 41, 3347-3359, J. Inorg. Biochem., 2000, 78, 303-311):

To a solution of maltol (79.3 mmol) in methanol (80 mL), is added a solution of NaOH 10.5N (1.1 eq). The reaction medium is then heated under reflux for 30 min. Benzyl chloride (1.2 eq) is then introduced dropwise over a period of 30 min at room temperature and the mixture is again heated under reflux for 18 h. After filtration under vacuum, the methanol is evaporated under reduced pressure, the residue is then taken in water and the desired product is extracted using dichloromethane. The organic phase is washed with a solution of NaOH 5%, then a saturated solution of NaCl, dried over $Na_2SO_4$ and finally evaporated under reduced pressure in order to give the derivative 40 in the form of a yellow oil (88%).

Compounds 41a (J. Heterocyclic Chem., 1994, 31, 947-56) and 41b (J. Inorg. Biochem., 2000, 78, 303-311):

To a solution of NaOH (3 eq) in a $EtOH/H_2O$ 1:1 mixture (100 mL), are added the compound 40 (18.5 mmol) and sodium glycinate or β-alanine (2 eq) (*Bioconjugate Chem.* 2005, 16, 1597-1609). The reaction medium is then heated under reflux for 18 h. After evaporation under a vacuum of the ethanol, the residue is taken in water and extracted using ethyl acetate in order to eliminate the remaining raw material. The aqueous phase is then concentrated under reduced pressure and acidified using a solution of HCl 6N and the derivative 41a or 41b is finally obtained after precipitation, filtration under vacuum and washing with water, in the form of a whitish powder (48 or 45%).

Compound 42 (Dalton Trans., 2004, 3772-3781):

To a solution of NaOH (0.5 eq) in a $EtOH/H_2O$ 1:1 mixture (20 mL), are added the compound 40 (18.5 mmol) and 1,3-diaminopropane (1.1 eq). The reaction medium is then heated under reflux for 18 h. After evaporation under a vacuum of the ethanol, the aqueous phase is acidified using HCl 6N and extracted using ethyl acetate in order to eliminate the remaining raw material. The aqueous phase is then neutralised using a solution of NaOH 6N and the desired product is extracted using ethyl acetate. The organic phase is washed with a saturated solution of NaCl, dried over $Na_2SO_4$ and finally evaporated under reduced pressure. After stirring of the intermediate compound at room temperature for 2 h in 1,4-dioxane (20 mL) in the presence of an off-the-shelf solution of HCl 4N in 1,4-dioxane (5 eq) and evaporation under reduced pressure of the 1,4-dioxane, the residue obtained is crushed in ether in order to give the derivative 42 in the form of a white powder (48%).

β—Various Pharmacomodulations Carried Out on "linker"

Reduction in the Carbonyl groups of the Compound 23f (Scheme 9):

Scheme 9: Reduction in the carbonyl groups of the compound 23f

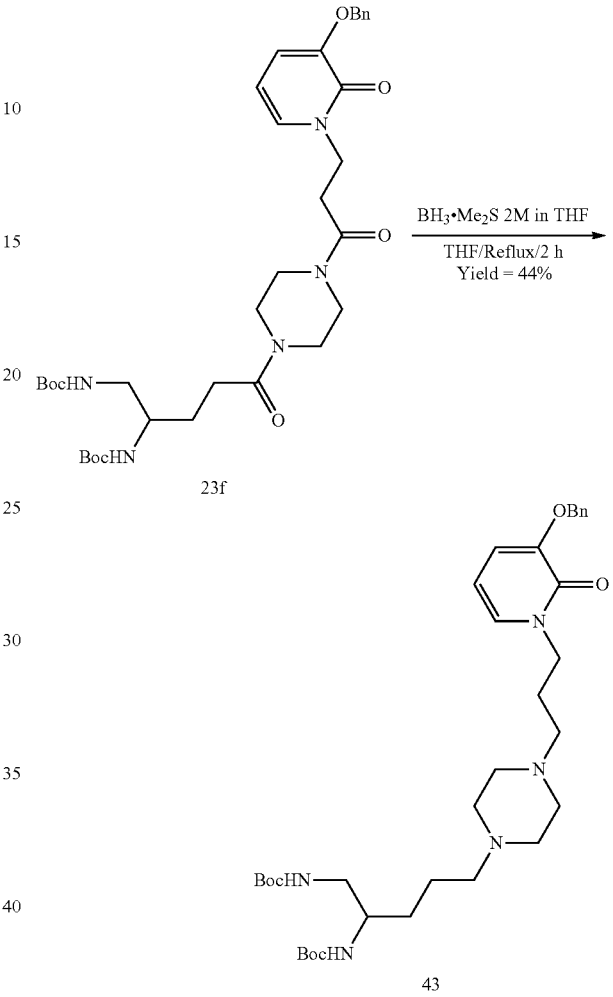

To a solution of the compound 23f (1 mmol) in THF (100 mL), is added dropwise a solution of borane/dimethyl sulphide 2M complex in THF (5 eq) (J. Med. Chem., 2005, 48, 3891-3902). The reaction medium is then heated under reflux for 2 h. After cooling, the borane is scavenged using MeOH and the mixture is again heated under reflux for 18 h. After evaporation under a vacuum of the MeOH, the residue is taken in a EtOH/NaOH 1N 5:1 mixture brought to reflux for 2 h. The aqueous phase is finally extracted using ethyl acetate after evaporation of the ethanol. The organic phase is washed with a saturated solution of NaCl, dried over $Na_2SO_4$ and evaporated under reduced pressure in order to give the derivative 43 in the form of a colourless oil (44%) after purification on a silica column (AcOEt/MeOH 50:50).

Compound 43: $^1$H NMR ($CDCl_3$, 400 MHz): δ (ppm) 7.40 (d, J=7.3 Hz, 2H); 7.32 (t, J=7.2 Hz, 2H); 7.26 (t, J=7.8 Hz, 1H); 6.93 (d, J=6.8 Hz, 1H); 6.61 (d, J=7.4 Hz, 1H); 5.96 (t, J=7.1 Hz, 1H); 5.27 (s, 3H); 5.08 (m, 2H); 4.98 (s, 1H); 3.99 (t, J=6.8 Hz, 2H); 3.57 (m, 1H); 3.14 (m, 2H); 2.43-2.31 (m, 10H); 1.92 (t, J=6.8 Hz, 2H); 1.54-1.52 (m, 2H); 1.40 (m, 20H).

$^{13}$C NMR (CDCl$_3$, 100 MHz): δ (ppm) 158.5 (2C); 149.0; 136.8; 129.8; 128.7 (2C); 128.1; 127.5 (2C); 115.7; 104.5; 79.4 (2C); 70.9; 58.2; 54.8 (2C); 53.4; 53.0; 51.2; 48.2; 45.1; 30.7; 29.9; 28.6 (6C); 26.0; 23.2.

MS (ESI+): m/z=[M+H] 628.3; [M+Na] 650.3.

HRMS (ESI+): m/z calculated for C$_{34}$H$_{54}$N$_5$O$_6$ [M+H]= 628.4074; found=628.4080.

Preparation of an N-Methylated and Decarbonylated Analogue of the Compound 23c (Scheme 10):

intermediate amine derivative (1 eq) is introduced with triethylamine (1.2 eq) in the reaction medium which is then kept under stirring at room temperature for 18 h. After evaporation of the DMF and taking of the residue in the ethyl acetate, the organic phase is washed with a solution of HCl 1N, NaHCO$_3$, then saturated NaCl, dried over Na$_2$SO$_4$ and finally evaporated under reduced pressure in order to give after purification on a silica column (AcOEt/MeOH 50:50) the compound 45 (89%).

Scheme 10: Preparation of an N-methylated and decarbonylated analogue of the compound 23c

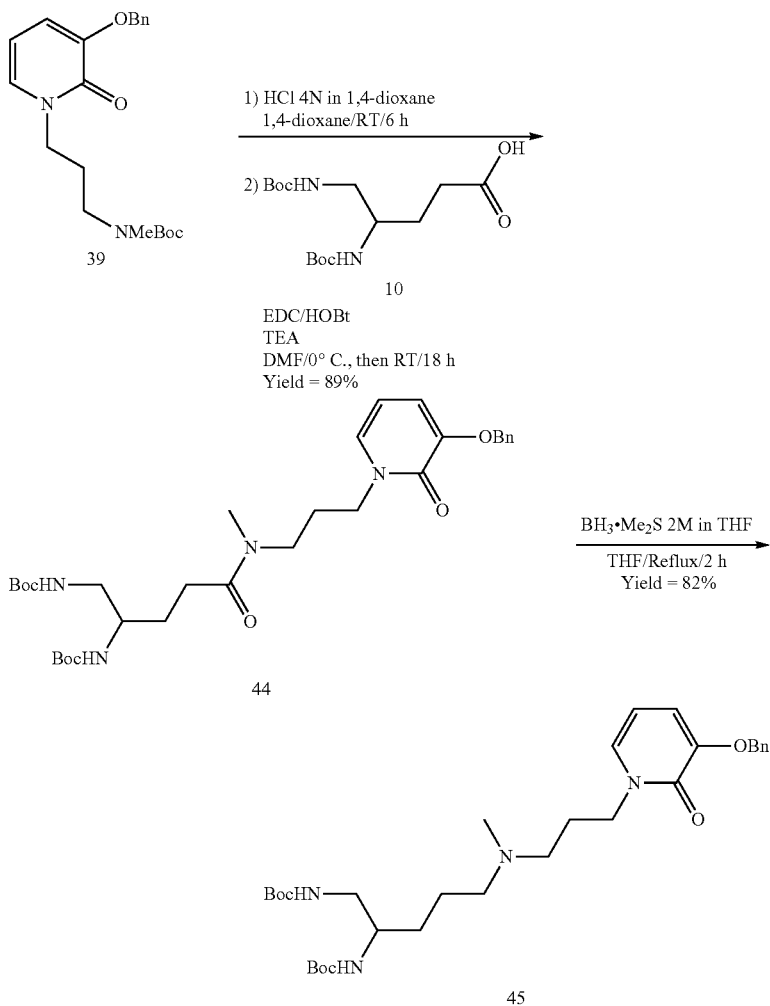

Compound 44

1$^{st}$ step: The compound 39 (0.7 mmol) is dissolved in 1,4-dioxane (2 mL) in the presence of an off-the-shelf solution of HCl 4N in 1,4-dioxane (20 eq). The reaction medium is then placed under stirring at room temperature for 6 h. The dioxane is evaporated under reduced pressure and the residue is crushed in ether in order to give the corresponding ammonia chlorhydrate in the form of a precipitate.

2$^{nd}$ step: To a solution of the compound 10 (0.8 mmol) in DMF (20 mL), placed under stirring at 0° C., are successively added 1-ethyl-3-(3-dimethylaminopropyl)-carbodiimide chlorhydrate (1.2 eq), 1-hydroxybenzotriazole monohydrate (1.1 eq). After 30 min of stirring at 0° C., the Compound 44: $^1$H NMR (CDCl$_3$, 400 MHz): δ (ppm) 7.39 (d, J=7.1 Hz, 2H); 7.31 (t, J=7.6 Hz, 2H); 7.27-7.25 (m, 1H); 7.01 (d, J=6.5 Hz, 1H); 6.61 (d, J=7.5 Hz, 1H); 5.99 (t, J=7.1 Hz, 1H); 5.06 (s, 2H); 5.02 (m, 2H); 3.95-3.88 (m, 2H); 3.60-3.59 (m, 1H); 3.46-3.29 (m, 2H); 3.17-3.15 (m, 2H); 2.95 (s, 3H); 2.43-2.29 (m, 2H); 2.02-1.92 (m, 2H); 1.85-1.77 (m, 2H); 1.39 (s, 18H).

$^{13}$C NMR (CDCl$_3$, 100 MHz): δ (ppm) 173.0; 158.4 (2C); 149.2; 136.6; 129.7; 128.8 (2C); 128.3; 127.6 (2C); 115.9; 104.9; 79.5; 79.4; 71.0; 51.7; 48.1; 45.3; 45.1; 35.4; 30.1; 28.6 (6C); 27.9; 27.0.

MS (ESI+): m/z=[M+Na] 609.3.

HRMS (ESI+): m/z calculated for C$_{31}$H$_{46}$N$_4$O$_7$Na [M+Na]=609.3264; found=609.3268.

Compound 45

To a solution of the compound 44 (0.5 mmol) in THF (30 mL), is added dropwise a solution of borane/dimethyl sulphide 2M complex in THF (2.5 eq). The reaction medium is then heated under reflux for 2 h. After cooling, the borane is scavenged using MeOH and the mixture is again heated under reflux for 18 h. After evaporation under a vacuum of the MeOH, the residue is taken in a EtOH/NaOH 1N 5:1 mixture brought to reflux for 2 h. The aqueous phase is finally extracted using ethyl acetate after evaporation of the ethanol. The organic phase is washed with a saturated solution of NaCl, dried over $Na_2SO_4$ and evaporated under reduced pressure in order to give the derivative 45 in the form of a brown powder (82%) after purification on a silica column (AcOEt/MeOH 70:30).

Compound 45: $^1$H NMR ($CDCl_3$, 400 MHz): δ (ppm) 7.41 (d, J=7.3 Hz, 2H); 7.33 (t, J=6.7 Hz, 2H); 7.26 (t, J=6.8 Hz, 1H); 6.94 (d, J=6.9 Hz, 1H); 6.63 (d, J=7.4 Hz, 1H); 6.00 (t, J=7.2 Hz, 1H); 5.08 (s, 2H); 5.08 (s, 2H); 5.06-5.01 (m, 2H); 3.99 (t, J=6.7 Hz, 2H); 3.58 (m, 1H); 3.16-3.15 (m, 2H); 2.37-2.30 (m, 4H); 2.17 (s, 3H); 1.92 (t, J=7.1 Hz, 2H); 1.51-1.50 (m, 2H); 1.40 (m, 20H).

$^{13}$C NMR ($CDCl_3$, 100 MHz): δ (ppm) 158.2 (2C); 149.0; 136.5; 129.6; 128.6 (2C); 128.0; 127.4 (2C); 115.7; 104.6; 79.3 (2C); 70.8; 57.2; 54.4; 51.3; 48.1; 45.0; 41.6; 30.7; 28.5 (6C); 23.4; 21.1.

MS (ESI+): m/z=[M+H] 573.4; [M+Na] 595.3.

HRMS (ESI+): m/z calculated for $C_{31}H_{49}N_4O_6$ [M+H]= 573.3652; found=573.3664.

Preparation of an Aliphatic "Linker" Carrier Devoid of an Amide Function (Scheme 11):

Scheme 11: Preparation of a derivative carrying an aliphatic "linker" devoid of an amide function

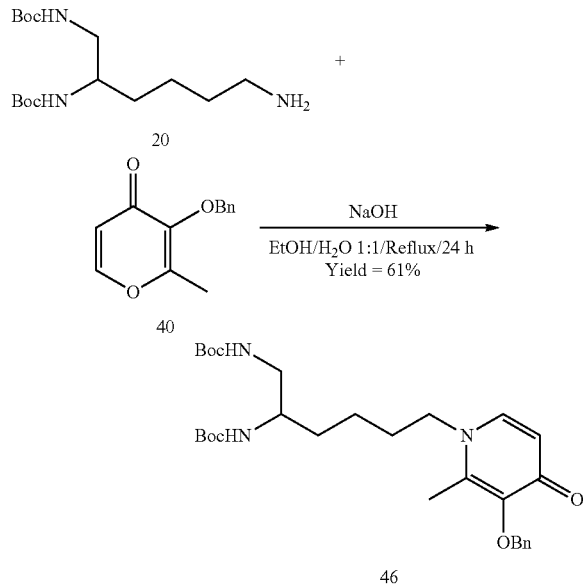

Compound 46:

To a solution of NaOH (0.5 eq) in a EtOH/$H_2O$ 1:1 mixture (120 mL), are added the compound 40 (5.1 mmol) and the compound 20 (0.7 eq). The reaction medium is then heated under reflux for 24 h (Dalton Trans., 2004, 3772-3781). After evaporation under a vacuum of the ethanol, the aqueous phase is neutralised using HCl 6N and extracted using ethyl acetate. The organic phase is washed with a saturated solution of NaCl, dried over $Na_2SO_4$ and finally evaporated under reduced pressure in order to give the derivative 46 in the form of a yellow powder (61%) after purification on a silica column (AcOEt/MeOH 90:10).

Compound 46: $^1$H NMR ($CDCl_3$, 400 MHz): δ (ppm) 7.38 (d, J=6.7 Hz, 2H); 7.32-7.26 (m, 3H); 7.16 (d, J=7.5 Hz, 1H); 6.39 (d, J=7.5 Hz, 1H); 5.03 (s, 2H); 4.95-4.93 (s, 2H); 3.71-3.76 (m, 2H); 3.59 (m, 1H); 3.14 (m, 2H); 2.06 (s, 3H); 1.66-1.55 (m, 2H); 1.40-1.35 (m, 22H).

$^{13}$C NMR ($CDCl_3$, 100 MHz): δ (ppm) 173.5; 156.6 (2C); 146.4; 141.0; 138.3; 137.9; 129.3 (2C); 128.4 (2C); 128.1; 117.5; 79.7 (2C); 73.1; 53.9; 51.2; 44.7; 32.6; 30.9; 28.5 (6C); 23.0; 12.5.

MS (ESI+): m/z=[M+H] 530.3.

HRMS (ESI+): m/z calculated for $C_{29}H_{44}N_3O_6$ [M+H]= 530.3230; found=530.3245.

γ—Debenzylation of the R'$_a$ Group (Scheme 12)

Scheme 12: Debenzylation of the R'$_a$ group

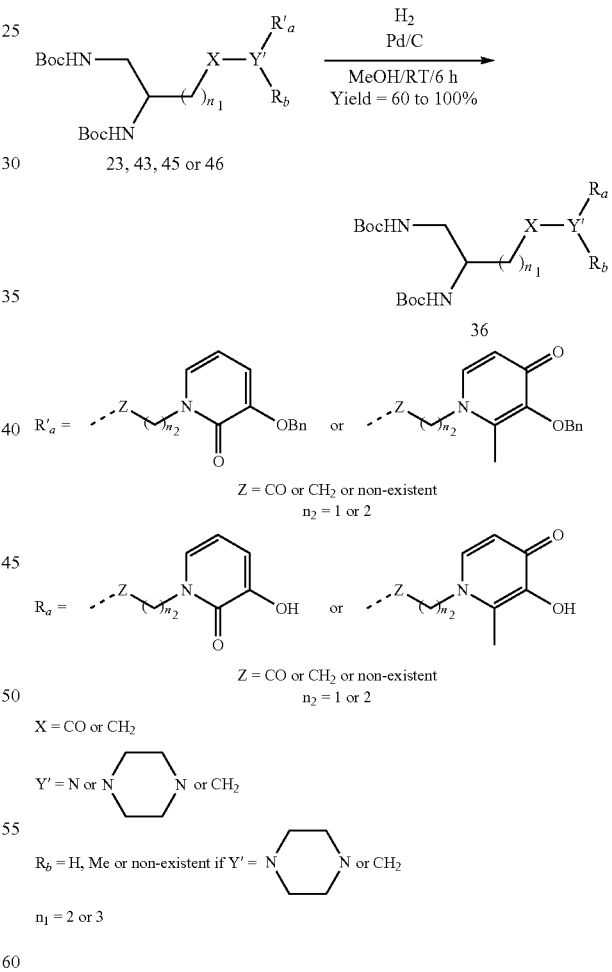

To a solution of the compound 23a-k, 43, 45 or 46 (0.2-1.6 mmol) in methanol (5-40 mL), is added Pd/C (10% m/m). The reaction medium is placed under vacuum and under stirring at room temperature for 30 min, and then kept under a flow of $H_2$ for 6 h. It is then filtered over paper and the methanol is evaporated under reduced pressure in order to give the derivative 36a-n (60 to 100%) (Table 3).

TABLE 3

Compounds 36

| Compound | $n_1$ | X | Y' | R'$_a$ | R$_b$ | Yield (%) | Aspect |
|---|---|---|---|---|---|---|---|
| 36a | 2 | CH$_2$ | N | 3-hydroxy-pyridin-2(1H)-one propanoyl | H | 100 | White powder |
| 36b | 3 | CH$_2$ | N | 3-hydroxy-pyridin-2(1H)-one butanoyl | H | 87 | Yellow powder |
| 36c | 2 | CO | N | 3-hydroxy-pyridin-2(1H)-one propyl | H | 100 | Brown oil |
| 36d | 1 | CO | piperazine | 3-hydroxy-pyridin-2(1H)-one propanoyl | Non-existent | 100 | Brown powder |
| 36e | 2 | CO | piperazine | 3-hydroxy-pyridin-2(1H)-one acetyl | Non-existent | 95 | White powder |
| 36f | 2 | CO | piperazine | 3-hydroxy-pyridin-2(1H)-one propanoyl | Non-existent | 82 | Brown powder |
| 36g | 2 | CH$_2$ | N | 3-OBn-2-methyl-pyridin-4(1H)-one acetyl | H | 78 | White powder |
| 36h | 3 | CH$_2$ | N | 3-OBn-2-methyl-pyridin-4(1H)-one acetyl | H | 71 | White powder |
| 36i | 3 | CH$_2$ | N | 3-hydroxy-2-methyl-pyridin-4(1H)-one propanoyl | H | 100 | Orange oil |

TABLE 3-continued

Compounds 36

| Compound | $n_1$ | X | Y' | $R'_a$ | $R_b$ | Yield (%) | Aspect |
|---|---|---|---|---|---|---|---|
| 36j | 2 | CO | N | pyridinone structure | H | 60 | White powder |
| 36k | 2 | CO | piperazine | pyridinone structure | Non-existent | 100 | White powder |
| 36l | 2 | CH$_2$ | piperazine | pyridinone structure | Non-existent | 94 | Brown powder |
| 36m | 2 | CH$_2$ | N | pyridinone structure | CH$_3$ | 96 | Brown powder |
| 36n | 1 | CH$_2$ | CH$_2$ | pyridinone structure | Non-existent | 91 | Brown powder |

Compound 36a: $^1$H NMR (CDCl$_3$, 600 MHz): δ (ppm) 6.95 (d, J=6.7 Hz, 1H); 6.92 (s, 1H); 6.82 (d, J=7.2 Hz, 1H); 6.14 (t, J=7.1 Hz, 1H); 5.18 (s, 1H); 5.04-5.03 (s, 1H); 4.25 (m, 2H); 3.56-3.54 (m, 1H); 3.17-3.16 (m, 2H); 3.09 (m, 2H); 2.68 (t, J=6.4 Hz, 2H); 1.50-1.40 (m, 22H).

$^{13}$C NMR (CDCl$_3$, 150 MHz): δ (ppm) 170.3; 158.7; 157.0; 156.7; 146.7; 128.6; 115.2; 107.2; 79.7 (2C); 50.8; 47.3; 44.8; 39.5; 35.5; 29.9; 28.6 (6C); 25.7.

MS (ESI+): m/z=[M+H] 483.3; [M+Na] 505.3.

HRMS (ESI+): m/z calculated for C$_{23}$H$_{38}$N$_4$O$_7$Na [M+Na]=505.2638; found=505.2644.

Compound 36b: $^1$H NMR (CDCl$_3$, 300 MHz): δ (ppm) 6.96 (dd, J$_1$=6.9 Hz and J$_2$=1.5 Hz, 1H); 6.80 (dd, J$_1$=7.4 Hz and J$_2$=1.5 Hz, 1H); 6.52-6.51 (s, 1H); 6.12 (t, J=7.2 Hz, 1H); 5.04 (s, 1H); 4.88-4.86 (s, 1H); 4.26 (t, J=6.3 Hz, 2H); 3.55-3.53 (m, 1H); 3.13-3.08 (m, 4H); 2.68 (t, J=6.3 Hz, 2H); 1.79-1.50 (m, 2H); 1.40 (s, 18H); 1.35-1.23 (m, 4H).

$^{13}$C NMR (CDCl$_3$, 75 MHz): δ (ppm) 169.7; 158.3 (2C); 146.2; 128.2; 114.6; 106.7; 79.5 (2C); 51.1; 46.9; 44.3; 38.8; 35.1; 31.9; 28.8; 28.2 (6C); 22.6.

MS (ESI+): m/z=[M−2Boc+3H] 296.9; [M−Boc+2H] 397.0; [M+H] 497.1; [M+Na] 519.1.

HRMS (ESI+): m/z calculated for C$_{24}$H$_{40}$N$_4$O$_7$Na [M+Na]=519.2795; found=519.2801.

Compound 36c: $^1$H NMR (CDCl$_3$, 300 MHz): δ (ppm) 7.34 (s, 1H); 6.89 (dd, J$_1$=6.9 Hz and J$_2$=1.2 Hz, 1H); 6.83 (d, J=7.2 Hz, 1H); 6.19 (t, J=6.9 Hz, 1H); 5.33-5.23 (s, 2H); 4.06 (t, J=5.2 Hz, 2H); 3.67-3.64 (m, 1H); 3.28-3.17 (m, 4H); 2.30 (t, J=7.2 Hz, 2H); 1.93 (t, J=6.3 Hz, 2H); 1.95-1.60 (m, 2H); 1.40 (s, 18H).

$^{13}$C NMR (CDCl$_3$, 75 MHz): δ (ppm) 173.3; 172.4; 158.6; 156.8; 146.5; 127.0; 114.6; 107.6; 79.4 (2C); 51.2; 47.1; 44.5; 35.9; 33.0; 29.3; 28.2 (6C); 25.4.

MS (ESI+): m/z=[M+H] 483.4; [M+Na] 505.3.

HRMS (ESI+): m/z calculated for C$_{23}$H$_{38}$N$_4$O$_7$Na [M+Na]=505.2638; found=505.2652.

Compound 36d: $^1$H NMR (CDCl$_3$, 600 MHz): δ (ppm) 7.03-7.01 (m, 1H); 6.80 (d, J=7.3 Hz, 1H); 6.10 (t, J=7.1 Hz, 1H); 5.66 (s, 1H); 4.98 (s, 1H); 4.27 (t, J=7.1 Hz, 2H); 3.89 (m, 1H); 3.66-3.31 (m, 8H); 3.23-3.21 (m, 2H); 2.87-2.85 (m, 2H); 2.67-2.46 (m, 2H); 1.39 (s, 18H).

$^{13}$C NMR (CDCl$_3$, 150 MHz): δ (ppm) 169.5; 169.0; 158.6; 157.0; 156.1; 146.5; 128.9; 115.1; 107.0; 79.8; 79.7; 49.5; 47.3; 45.8 (2C); 43.9; 41.8 (2C); 35.4; 32.1; 28.6 (6C).

MS (ESI+): m/z=[M−2Boc+3H] 352.1; [M−Boc+2H] 452.2; [M+H] 552.2; [M+Na] 574.2.

HRMS (ESI+): m/z calculated for C$_{26}$H$_{41}$N$_5$O$_8$Na [M+Na]=574.2853; found=574.2849.

Compound 36e: $^1$H NMR (CDCl$_3$, 400 MHz): δ (ppm) 6.80 (d, J=6.4 Hz, 2H); 6.18 (t, J=7.1 Hz, 1H); 5.06-4.99 (s, 2H); 4.85-4.71 (m, 2H); 3.86-3.38 (m, 9H); 3.21-3.15 (m, 2H); 2.46-2.32 (m, 2H); 1.92-1.64 (m, 2H); 1.40 (s, 18H).

$^{13}$C NMR (CDCl$_3$, 100 MHz): δ (ppm) 171.6; 165.4; 158.9; 157.2; 156.6; 146.7; 128.1; 114.9; 107.2; 79.8 (2C); 51.6; 49.9; 45.2; 44.8; 42.5; 41.8; 41.5; 30.0; 28.6 (6C); 28.2.

MS (ESI+): m/z=[M+H] 552.3; [M+Na] 574.3.

HRMS (ESI+): m/z calculated for C$_{26}$H$_{41}$N$_5$O$_8$Na [M+Na]=574.2853; found=574.2832.

Compound 36f: ¹H NMR (CDCl₃, 400 MHz): δ (ppm) 7.01-7.00 (m, 1H); 7.76 (d, J=7.1 Hz, 1H); 6.09 (t, J=6.9 Hz, 1H); 5.04 (s, 2H); 4.23 (t, J=5.9 Hz, 2H); 3.67-3.36 (m, 9H); 3.12 (m, 2H); 2.83 (m, 2H); 2.36-2.30 (m, 2H); 1.80-1.62 (m, 2H); 1.35 (s, 18H).

¹³C NMR (CDCl₃, 100 MHz): δ (ppm) 171.3; 169.0; 158.6; 156.7; 156.4; 146.5; 128.6; 114.8; 106.7; 79.3 (2C); 51.4; 47.1; 45.2; 44.4 (2C); 41.6 (2C); 31.7; 29.4; 28.4 (6C); 27.7.

MS (ESI+): m/z=[M+H] 566.3; [M+Na] 588.3.

HRMS (ESI+): m/z calculated for $C_{27}H_{43}N_5O_8Na$ [M+Na]=588.3009; found=588.2980.

Compound 36g: ¹H NMR (CDCl₃, 400 MHz): δ (ppm) 7.49 (d, J=4.8 Hz, 1H); 6.33 (d, J=4.8 Hz, 1H); 4.70 (s, 2H); 3.53-3.51 (m, 1H); 3.19-3.17 (m, 2H); 3.07-2.91 (m, 2H); 2.26 (s, 3H); 1.56-1.44 (m, 4H); 1.42 (s, 18H).

¹³C NMR (CDCl₃, 100 MHz): δ (ppm) 169.9; 167.1; 157.3; 157.0; 145.5; 139.0; 131.9; 111.1; 78.6 (2C); 55.5; 50.5; 44.1; 39.2; 29.6; 27.4 (6C); 25.4; 10.7.

MS (ESI+): m/z=[M+H] 483.2.

HRMS (ESI+): m/z calculated for $C_{23}H_{38}N_4O_7Na$ [M+Na]=505.2638; found=505.2636.

Compound 36 h: ¹H NMR (CDCl₃, 400 MHz): δ (ppm) 7.57 (d, J=4.8 Hz, 1H); 6.41 (d, J=4.8 Hz, 1H); 4.77 (s, 2H); 3.57 (m, 1H); 3.14-3.11 (m, 2H); 3.02-2.98 (m, 2H); 2.34 (s, 3H); 1.58-1.49 (m, 2H); 1.40 (s, 20H); 1.39-1.35 (m, 2H).

¹³C NMR (CDCl₃, 100 MHz): δ (ppm) 169.9; 167.1; 157.3; 157.0; 145.5; 139.0; 131.9; 111.1; 78.6 (2C); 55.5; 50.7; 44.0; 39.1; 31.6; 28.7; 27.4 (6C); 22.9; 10.7.

MS (ESI+): m/z=[M+H] 497.3; [M+Na] 519.2.

HRMS (ESI+): m/z calculated for $C_{24}H_{40}N_4O_7Na$ [M+Na]=519.2795; found=519.2789.

Compound 36i: ¹H NMR (CDCl₃, 400 MHz): δ (ppm) 7.56 (d, J=7.2 Hz, 1H); 6.37 (d, J=7.2 Hz, 1H); 4.37-4.33 (m, 2H); 3.53 (m, 1H); 3.13-3.07 (m, 2H); 3.00-2.95 (m, 2H); 2.64 (t, J=6.5 Hz, 2H); 2.46 (s, 3H); 1.44 (s, 18H); 1.44-1.40 (m, 4H); 1.40-1.23 (m, 2H).

¹³C NMR (CDCl₃, 100 MHz): δ (ppm) 171.5; 170.8; 158.5; 158.2; 147.1; 139.0; 132.5; 112.5; 80.0 (2C); 51.4; 50.3; 45.4; 40.2; 37.6; 32.9; 30.0; 28.8 (6C); 24.3; 11.8.

MS (ESI+): m/z=[M+H] 511.3; [M+Na] 533.2.

HRMS (ESI+): m/z calculated for $C_{25}H_{42}N_4O_7Na$ [M+Na]=533.2951; found=533.2935.

Compound 36j: ¹H NMR (CDCl₃, 400 MHz): δ (ppm) 7.39 (m, 2H); 6.31 (m, 1H); 5.40-5.33 (s, 2H); 3.95 (m, 2H); 3.55 (m, 1H); 3.40-3.13 (m, 4H); 2.35 (s, 3H); 2.24 (m, 2H); 1.96-1.60 (m, 4H); 1.40 (s, 18H).

¹³C NMR (CDCl₃, 100 MHz): δ (ppm) 174.2; 169.8; 157.7 (2C); 146.8; 137.5; 129.3; 111.6; 80.2 (2C); 52.2; 51.6; 44.9; 36.8; 33.5; 31.4; 30.2; 28.7 (6C); 12.1.

MS (ESI+): m/z=[M+H] 497.2; [M+Na] 519.3.

HRMS (ESI+): m/z calculated for $C_{24}H_{40}N_4O_7Na$ [M+Na]=519.2795; found=519.2795.

Compound 36k: ¹H NMR (CDCl₃, 400 MHz): δ (ppm) 7.26 (m, 1H); 6.35 (m, 1H); 5.98 (s, 2H); 5.13 (m, 2H); 4.88 (m, 1H); 3.67-3.66 (m, 8H); 3.14 (m, 2H); 2.35 (m, 2H); 2.17 (s, 3H); 1.80-1.63 (m, 2H), 1.40 (s, 18H).

¹³C NMR (CDCl₃, 100 MHz): δ (ppm) 171.6; 168.9; 164.5; 156.9 (2C); 142.8; 138.6; 128.5; 111.5; 79.6 (2C); 55.0; 50.7; 45.2; 44.9; 44.6; 42.1; 41.5; 29.9; 28.4 (6C); 28.1; 12.2.

MS (ESI+): m/z=[M+H] 566.3; [M+Na] 588.3.

HRMS (ESI+): m/z calculated for $C_{27}H_{43}N_5O_8Na$ [M+Na]=588.3009; found=588.3002.

Compound 36l: ¹H NMR (CDCl₃, 400 MHz): δ (ppm) 6.83 (d, J=6.8 Hz, 1H); 6.76 (d, J=7.3 Hz, 1H); 6.11 (t, J=7.1 Hz, 1H); 5.17-5.08 (s, 2H); 4.02 (t, J=6.9 Hz, 2H); 3.56 (m, 1H); 3.15-3.12 (m, 4H); 2.91-2.83 (m, 6H); 2.57-2.56 (m, 2H); 2.12 (m, 2H); 1.80-1.78 (m, 2H); 1.37 (m, 22H).

¹³C NMR (CDCl₃, 100 MHz): δ (ppm) 159.0; 157.2; 156.3; 147.0; 127.4; 114.3; 107.1; 79.7 (2C); 56.9; 54.4; 51.1; 50.2 (2C); 48.4; 44.7 (2C); 30.1; 28.6 (6C); 27.3; 25.5; 21.2.

MS (ESI+): m/z=[M+H] 538.3.

HRMS (ESI+): m/z calculated for $C_{27}H_{48}N_5O_6$ [M+H]= 538.3605; found=538.3611.

Compound 36m: ¹H NMR (CDCl₃, 400 MHz): δ (ppm) 6.85 (d, J=6.6 Hz, 1H); 6.77 (dd, J₁=7.3 Hz and J₂=1.5 Hz, 1H); 6.12 (t, J=7.1 Hz, 1H); 5.07 (s, 2H); 4.02-3.88 (m, 2H); 3.59 (m, 1H); 3.16 (m, 2H); 2.34-2.32 (m, 4H); 2.16 (s, 3H); 1.90 (t, J=6.6 Hz, 2H); 1.51 (m, 4H); 1.41 (s, 18H).

¹³C NMR (CDCl₃, 100 MHz): δ (ppm) 159.3; 156.9 (2C); 147.1; 127.6; 113.7; 106.8; 79.5 (2C); 57.5; 54.5; 51.4; 48.3; 45.1; 42.0; 31.4; 28.6 (6C); 26.8; 24.4.

MS (ESI+): m/z=[M+H] 483.4; [M+Na] 505.3.

HRMS (ESI+): m/z calculated for $C_{24}H_{43}N_4O_6$ [M+]= 483.3183; found=483.3172.

Compound 36n: ¹H NMR (CDCl₃, 400 MHz): δ (ppm) 7.86 (m, 1H); 7.03-7.02 (m, 2H); 5.19-5.10 (m, 2H); 4.19 (m, 2H); 3.59 (m, 1H); 3.13 (m, 2H); 2.51 (s, 3H); 1.84-1.78 (m, 2H); 1.39-1.38 (m, 22H).

¹³C NMR (CDCl₃, 100 MHz): δ (ppm) 161.5; 157.1; 156.6; 144.5; 138.4; 137.5; 112.3; 79.6 (2C); 56.3; 51.2; 44.6; 32.3; 30.3; 28.6 (6C); 22.8; 12.8.

MS (ESI+): m/z=[M+H] 440.3.

HRMS (ESI+): m/z calculated for $C_{22}H_{38}N_3O_6$ [M+H] =440.2761; found=440.2749.

δ—Final Deprotection of the Diamine Group (Scheme 13)

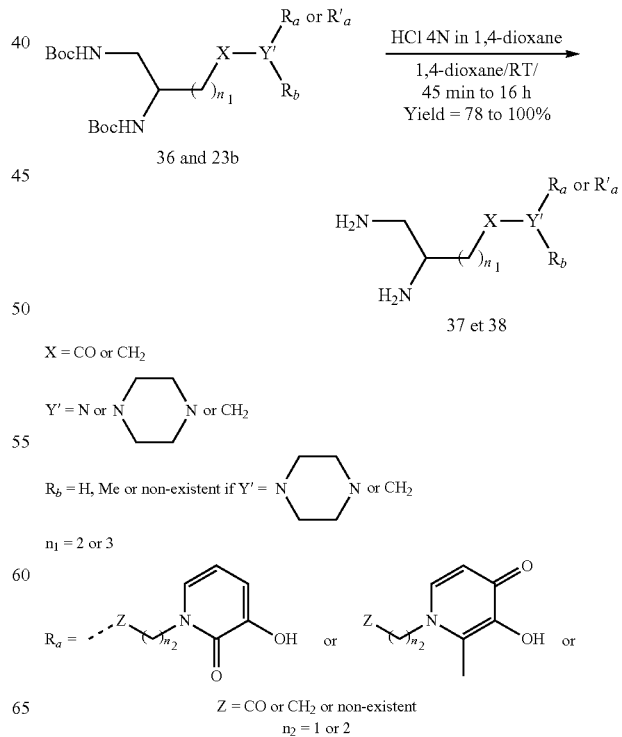

Scheme 13: Final deprotection of the diamine group

R'ₐ = 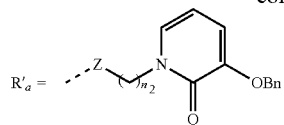

The compound 36a-n or 23b (0.2-1.7 mmol) is dissolved in 1,4-dioxane (4-10 mL) in the presence of an off-the-shelf solution of HCl 4N in 1,4-dioxane (20 eq). The reaction medium is then placed under stirring at room temperature for 45 min at 16 h. The dioxane is evaporated under reduced pressure and the residue is crushed in ether. After evaporation under a vacuum (highly hygroscopic products), the precipitate obtained is lyophilised in order to give the derivative 37a-n or 38 (78 to 100%) (Table 4).

TABLE 4

Compounds 37 and 38

| Compound | $n_1$ | X | Y' | R'ₐ | $R_b$ | Yield (%) | Aspect |
|---|---|---|---|---|---|---|---|
| 37a | 2 | CH$_2$ | N | 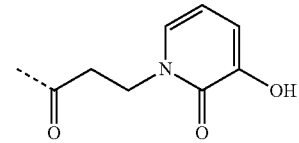 | H | 100 | Yellow powder |
| 37b | 3 | CH$_2$ | N | 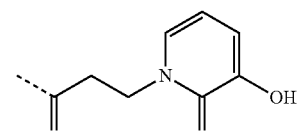 | H | 100 | Yellow powder |
| 37c | 2 | CO | N | 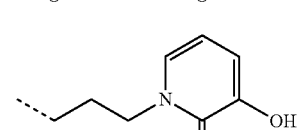 | H | 93 | White powder |
| 37d | 1 | CO |  | 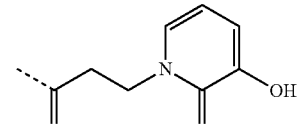 | Non-existent | 88 | White powder |
| 37e | 2 | CO |  | 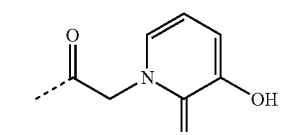 | Non-existent | 100 | Beige powder |
| 37f | 2 | CO |  | 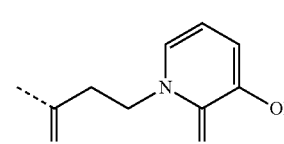 | Non-existent | 100 | Yellow powder |
| 37g | 2 | CH$_2$ | N | 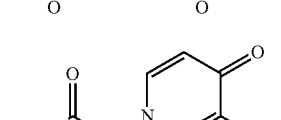 | H | 100 | White powder |
| 37h | 3 | CH$_2$ | N | 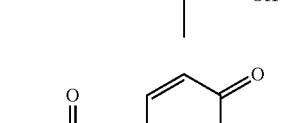 | H | 100 | White powder |

TABLE 4-continued

Compounds 37 and 38

| Compound | $n_1$ | X | Y' | $R'_a$ | $R_b$ | Yield (%) | Aspect |
|---|---|---|---|---|---|---|---|
| 37i | 3 | $CH_2$ | N | 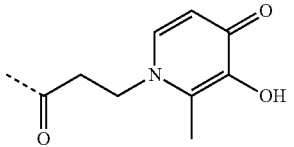 | H | 100 | White powder |
| 37j | 2 | CO | N | 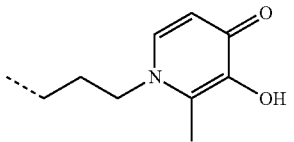 | H | 100 | White powder |
| 37k | 2 | CO | 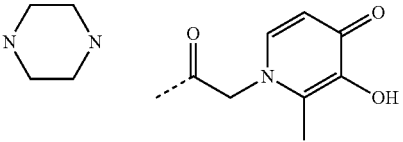 | 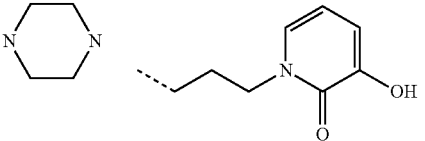 | Non-existent | 100 | White powder |
| 37l | 2 | $CH_2$ | 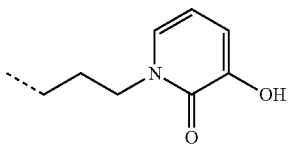 | 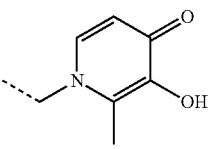 | Non-existent | 78 | White powder |
| 37m | 2 | $CH_2$ | N | 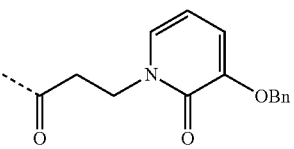 | $CH_3$ | 87 | White powder |
| 37n | 1 | $CH_2$ | $CH_2$ |  | Non-existent | 86 | White powder |
| 38 | 3 | $CH_2$ | N |  | H | 100 | Orange powder |

Compound 37a: $^1$H NMR (D$_2$O, 400 MHz): δ (ppm) 7.16 (dd, J$_1$=6.8 Hz and J$_2$=1.4 Hz, 1H); 7.05 (dd, J$_1$=7.5 Hz and J$_2$=1.4 Hz, 1H); 6.41 (t, J=7.1 Hz, 1H); 4.30 (t, J=6.4 Hz, 2H); 3.67-3.64 (m, 1H); 3.35-3.34 (m, 2H); 3.18 (t, J=6.7 Hz, 2H); 2.72 (t, J=6.4 Hz, 2H); 1.76-1.57 (m, 4H).

$^{13}$C NMR (D$_2$O, 100 MHz): δ (ppm) 173.3; 158.5; 145.5; 129.4; 118.8; 108.5; 49.0; 47.4; 40.9; 38.7; 35.3; 27.5; 24.1.

MS (ESI+): m/z=[M+H] 283.1.

HRMS (ESI+): m/z calculated for C$_{13}$H$_{23}$N$_4$O$_3$ [M+H]= 283.1770; found=283.1765.

Compound 37b: $^1$H NMR (d$_6$-DMSO, 300 MHz): δ (ppm) 8.59 (s, 4H); 8.10-8.07 (s, 1H); 7.08 (dd, J$_1$=6.9 Hz and J$_2$=7.2 Hz, 1H); 6.70 (dd, J$_1$=7.2 Hz and J$_2$=1.5 Hz, 1H); 6.07 (t, J=7.2 Hz, 1H); 4.10 (t, J=6.9 Hz, 2H); 3.40-3.38 (m, 1H); 3.09-3.00 (m, 4H); 2.53-2.49 (m, 2H); 1.63-1.58 (m, 2H); 1.19 (m, 4H).

$^{13}$C NMR (d$_6$-DMSO, 75 MHz): δ (ppm) 169.6; 157.8; 146.8; 128.6; 115.0; 105.4; 49.1; 45.9; 40.6; 38.2; 34.8; 29.7; 28.6; 21.9.

MS (ESI+): m/z=[M+H] 296.9.

HRMS (ESI+): m/z calculated for C$_{14}$H$_{25}$N$_4$O$_3$ [M+H]= 297.1927; found=297.1914.

Compound 37c: $^1$H NMR (d$_6$-DMSO, 300 MHz): δ (ppm) 8.63 (s, 2H); 8.54 (s, 2H); 8.30 (s, 1H); 7.20 (dd, J$_1$=6.8 Hz and J$_2$=1.5 Hz, 1H); 6.72 (dd, J$_1$=7.2 Hz and J$_2$=1.8 Hz, 1H); 6.11 (t, J=6.9 Hz, 1H); 3.96-3.87 (m, 2H); 3.49-3.46 (m, 1H); 3.11-3.04 (m, 4H); 2.32-2.31 (m, 2H); 1.90-1.75 (m, 4H).

$^{13}$C NMR (d$_6$-DMSO, 75 MHz): δ (ppm) 171.2; 157.6; 146.6; 128.2; 114.8; 105.5; 48.7; 46.6; 40.3; 35.8; 30.8; 28.7; 26.1.

MS (ESI+): m/z=[M+H] 283.0.

HRMS (ESI+): m/z calculated for $C_{13}H_{23}N_4O_3$ [M+H]= 283.1810; found=283.1800.

Compound 37d: $^1$H NMR (D$_2$O, 400 MHz): δ (ppm) 7.20 (d, J=6.4 Hz, 1H); 7.03 (d, J=6.6 Hz, 1H); 6.39 (t, J=6.9 Hz, 1H); 4.32-4.28 (m, 1H); 4.06-4.02 (m, 2H); 3.69-3.45 (m, 8H); 3.17-3.10 (m, 2H); 3.04-3.01 (m, 2H); 2.99-2.95 (m, 2H).

$^{13}$C NMR (D$_2$O, 100 MHz): δ (ppm) 172.8; 171.5; 168.8; 158.5; 129.5; 118.9; 108.3; 47.1; 45.5; 45.3; 44.7; 44.3; 41.5; 40.7; 33.2; 31.5.

MS (ESI+): m/z=[M+H] 352.2.

HRMS (ESI+): m/z calculated for $C_{16}H_{26}N_5O_4$ [M+H]= 352.1985; found=352.1977.

Compound 37e: $^1$H NMR (D$_2$O, 400 MHz): δ (ppm) 7.14-7.08 (m, 2H); 6.44 (m, 1H); 5.01 (s, 2H); 3.94-3.85 (m, 1H); 3.66 (m, 8H); 3.17 (m, 2H); 2.78-2.76 (m, 2H); 2.13-2.08 (m, 2H).

$^{13}$C NMR (D$_2$O, 100 MHz): δ (ppm) 172.5; 167.2; 158.7; 145.4; 130.1; 119.2; 108.3; 51.2; 49.2; 44.6; 44.1; 42.9; 41.7; 41.3; 28.5; 25.3.

MS (ESI+): m/z=[M+H] 352.2.

HRMS (ESI+): m/z calculated for $C_{16}H_{26}N_5O_4$ [M+H]= 352.1985; found=352.1981.

Compound 37f: $^1$H NMR (D$_2$O, 400 MHz): δ (ppm) 7.20 (d, J=6.3 Hz, 1H); 7.03 (d, J=6.4 Hz, 1H); 6.39 (t, J=6.8 Hz, 1H); 4.30 (t, J=6.3 Hz, 2H); 3.75-3.60 (m, 4H); 3.55-3.52 (m, 5H); 3.37-3.35 (m, 2H); 2.98-2.95 (m, 2H); 2.74-2.68 (m, 2H); 2.11-2.03 (m, 2H).

$^{13}$C NMR (D$_2$O, 100 MHz): δ (ppm) 172.7; 161.7; 158.8; 145.3; 129.5; 118.6; 108.3; 49.0; 47.0; 45.1; 44.4; 41.5; 41.2; 40.6; 31.4; 28.3; 25.2.

MS (ESI+): m/z=[M+H] 366.2.

HRMS (ESI+): m/z calculated for $C_{17}H_{28}N_5O_4$ [M+H]= 366.2146; found=366.2134.

Compound 37g: $^1$H NMR (CD$_3$OD, 400 MHz): δ (ppm) 8.22 (d, J=5.8 Hz, 1H); 7.16 (d, J=5.8 Hz, 1H); 5.29 (s, 2H); 3.66-3.61 (m, 1H); 3.35-3.31 (m, 4H); 2.53 (s, 3H); 1.90-1.73 (m, 4H).

$^{13}$C NMR (CD$_3$OD, 100 MHz): δ (ppm) 167.1; 160.7; 145.0; 144.3; 141.2; 111.5; 59.4; 51.0; 42.4; 40.1; 29.1; 26.2; 13.3.

MS (ESI+): m/z=[M+H] 283.2.

HRMS (ESI+): m/z calculated for $C_{13}H_{23}N_4O_3$ [M+H]= 283.1770; found=283.1772.

Compound 37 h: $^1$H NMR (CD$_3$OD, 400 MHz): δ (ppm) 8.15 (d, J=6.8 Hz, 1H); 7.12 (d, J=6.6 Hz, 1H); 5.22 (s, 2H); 3.58-3.56 (m, 1H); 3.29-3.25 (m, 4H); 2.48 (s, 3H); 1.81-1.73 (m, 2H); 1.62-1.49 (m, 4H).

$^{13}$C NMR (CD$_3$OD, 100 MHz): δ (ppm) 166.8; 160.4; 144.8; 143.9; 140.8; 111.4; 59.1; 50.9; 42.9; 40.3; 31.0; 29.7; 23.2; 12.9.

MS (ESI+): m/z=[M+H] 297.2; [M+Na] 319.2.

HRMS (ESI+): m/z calculated for $C_{14}H_{25}N_4O_3$ [M+H]= 297.1927; found=297.1913.

Compound 37i: $^1$H NMR (D$_2$O, 400 MHz): δ (ppm) 7.97 (d, J=6.6 Hz, 1H); 7.18 (d, J=7.0 Hz, 1H); 4.68 (t, J=6.4 Hz, 2H); 3.71-3.65 (m, 1H); 3.38-3.37 (m, 2H); 3.16 (t, J=6.7 Hz, 2H); 3.08-3.04 (s, 1H); 2.88 (t, J=6.5 Hz, 2H); 2.56 (s, 3H); 1.85-1.74 (m, 2H); 1.52-1.38 (m, 4H).

$^{13}$C NMR (D$_2$O, 100 MHz): δ (ppm) 171.3 (2C); 158.2; 142.4; 138.7; 110.9; 52.7; 49.2; 40.8; 38.9; 35.8; 29.6; 27.9; 21.6; 12.3.

MS (ESI+): m/z=[M+H] 311.2.

HRMS (ESI+): m/z calculated for $C_{15}H_{27}N_4O_3$ [M+H]= 311.2083; found=311.2075.

Compound 37j: $^1$H NMR (D$_2$O, 400 MHz): δ (ppm) 8.28 (d, J=6.5 Hz, 1H); 7.13 (d, J=6.5 Hz, 1H); 4.44 (m, 2H); 3.33-3.29 (m, 5H); 2.64 (s, 3H); 2.57 (m, 2H); 2.08-2.07 (m, 4H).

$^{13}$C NMR (D$_2$O, 100 MHz): δ (ppm) 174.9; 159.8; 145.2; 143.4; 139.4; 111.7; 55.7; 50.6; 41.9; 37.3; 32.2; 31.0; 27.1; 12.8.

MS (ESI+): m/z=[M+H] 297.2.

HRMS (ESI+): m/z calculated for $C_{14}H_{25}N_4O_3$ [M+H]= 297.1927; found=297.1931.

Compound 37k: $^1$H NMR (D$_2$O, 400 MHz): δ (ppm) 8.01 (d, J=6.8 Hz, 1H); 7.19 (d, J=6.9 Hz, 1H); 5.53 (s, 2H); 3.72-3.55 (m, 9H); 3.41-3.39 (m, 2H); 2.81-2.75 (m, 2H); 2.47 (s, 3H); 2.16-2.08 (m, 2H).

$^{13}$C NMR (D$_2$O, 100 MHz): δ (ppm) 172.4; 165.2; 159.4; 143.4; 142.5; 139.9; 111.1; 57.2; 49.1; 44.5; 44.1; 42.2; 41.4; 40.7; 28.5; 25.3; 12.5.

MS (ESI+): m/z=[M+H] 366.2.

HRMS (ESI+): m/z calculated for $C_{17}H_{28}N_5O_4$ [M+H]= 366.2141; found=366.2133.

Compound 37l: $^1$H NMR (d$_6$-DMSO, 400 MHz): δ (ppm) 6.83 (d, J=6.8 Hz, 1H); 6.76 (d, J=7.3 Hz, 1H); 6.11 (t, J=7.1 Hz, 1H); 5.17-5.08 (s, 2H); 4.02 (t, J=6.9 Hz, 2H); 3.56 (m, 1H); 3.15-3.12 (m, 4H); 2.91-2.83 (m, 6H); 2.57-2.56 (m, 2H); 2.12 (m, 2H); 1.80-1.78 (m, 2H); 1.37 (m, 22H).

$^{13}$C NMR (d$_6$-DMSO, 100 MHz): δ (ppm) 159.0; 157.2; 156.3; 147.0; 127.4; 114.3; 107.1; 79.7 (2C); 56.9; 54.4; 51.1; 50.2 (2C); 48.4; 44.7 (2C); 30.1; 28.6 (6C); 27.3; 25.5; 21.2.

MS (ESI+): m/z=[M+H] 338.3.

HRMS (ESI+): m/z calculated for $C_{17}H_{32}N_5O_2$ [M+H]= 338.2556; found=338.2552.

Compound 37m: $^1$H NMR (CD$_3$OD, 400 MHz): δ (ppm) 7.49 (m, 1H); 7.14 (m, 1H); 6.60-6.59 (m, 1H); 4.34-4.30 (m, 2H); 3.82-3.78 (m, 1H); 3.40-3.34 (m, 4H); 3.31-3.26 (m, 2H); 2.95 (s, 3H); 2.35-2.31 (m, 2H); 2.03-1.91 (m, 4H).

$^{13}$C NMR (CD$_3$OD, 100 MHz): δ (ppm) 158.8; 147.8; 130.1; 121.2; 112.2; 56.8; 54.6; 50.3; 49.8; 42.1; 40.9; 28.5; 25.4; 21.2.

MS (ESI+): m/z=[M+H] 283.2.

HRMS (ESI+): m/z calculated for $C_{14}H_{27}N_4O_2$ [M+]= 283.2134; found=283.2133.

Compound 37n: $^1$H NMR (CD$_3$OD, 400 MHz): δ (ppm) 8.25 (d, J=7.0 Hz, 1H); 7.13 (d, J=6.9 Hz, 1H); 4.42 (t, J=7.6 Hz, 2H); 3.64-3.61 (m, 1H); 3.31-3.27 (m, 2H); 2.64 (s, 3H); 1.93-1.82 (m, 4H); 1.57-1.56 (m, 2H).

$^{13}$C NMR (CD$_3$OD, 100 MHz): δ (ppm) 159.5; 145.0; 143.1; 139.6; 111.8; 57.4; 50.6; 42.0; 31.0; 30.7; 22.7; 12.7.

MS (ESI+): m/z=[M+H] 240.2.

HRMS (ESI+): m/z calculated for $C_{12}H_{22}N_3O_2$ [M+H]= 240.1712; found=240.1713.

Compound 38: $^1$H NMR (CD$_3$OD, 400 MHz): δ (ppm) 7.46 (s, 2H); 7.37-7.27 (m, 3H); 6.58 (m, 1H); 5.21 (m, 2H); 4.40 (m, 2H); 3.62 (m, 1H); 3.32-3.31 (m, 2H); 3.19 (m, 2H); 2.77 (m, 2H); 1.80 (m, 2H); 1.53 (m, 4H).

$^{13}$C NMR (CD$_3$OD, 100 MHz): δ (ppm) 171.4; 157.1; 147.2; 135.7; 130.3; 128.6 (2C); 128.2; 127.8 (2C); 119.3; 109.5; 71.0; 49.6; 40.8; 38.5; 34.7; 32.4; 29.7; 28.3; 21.8.

MS (ESI+): m/z=[M+H] 387.2.

HRMS (ESI+): m/z calculated for $C_{21}H_{31}N_4O_3$ [M+H]= 387.2396; found=387.2382.

B. Physico-Chemical Studies

I) Evaluation of the Formation of Adducts Between the Compounds According to the Invention (29a, 29b, 30a, 30b; 37a, 37b, 37c, 37d, 37f, 37i, 37j) and of α-Oxoaldehydes or of α,β-Unsaturated Aldehydes by HPLC Analysis 1—Principle The compounds to be tested are incubated at 37° C. in the presence of MGO or of MDA. A kinetic study aiming to report on the formation of adducts with the MGO or MDA is then carried out via HPLC analysis.

2—Method a) Preparation of the Solutions

The compounds to be tested (30 µmol) are dissolved in PBS (1.5 mL). An aqueous solution (qsp 1.25 mL) of MGO at 40% in water (250 µmol) is then prepared and in parallel, MDA bis-(diOEt)-acetal (250 µmol) is set to react with a solution of HCl 1N (2 eq) in water (qsp 1.25 mL) for 1 h at room temperature. An aqueous solution of NaOH 0.05N is also required to neutralise the reaction medium (5 mL).

b) Incubation of the Mixtures at 37° C.

The solution of the compound to be tested (625 µL—final concentration in the medium=10 mM) is then set to react with the solution of MGO or of MDA prepared extemporaneously (125 µL—final concentration in the medium=20 mM) in the presence of NaOH 0.05 N (0.5 mL).

The various mixtures are then incubated in the oven at 37° C. for 24 h.

c) Analysis Via HPLC

A sampling of each mixture (100 µL) is taken at regular intervals of time (0.25; 0.5; 1; 5 and 24 h) and stored at −20° C. in order to stop the reaction. After dilution in a MeCN/H$_2$O 98:2 mixture at room temperature, the HPLC analysis is carried out on a Shimadzu LCMS-2020 apparatus (UV chromatogram at 190 nm and mass spectrum in positive electrospray ionisation mode (ESI+)) after separation on the Waters Acquity column using a gradient of solvents H$_2$O+HCOOH 0.1%/MeCN+HCOOH 0.1% (98/2 for 2 min, then 55/45 for 2 min and 45/55 for 3 min) with a flow rate of 0.3 mL/min at 40° C. and an injection of volume of 1 ("detection mode: scan, interface voltage: tuning file, DL voltage: 100 V, Q-array DC: 40 V, Q-array RF: 40 V"). A blank is first of all carried out using a solution containing the reaction medium without scavenger. Then, a free scavenger solution at 10 mM is used as a negative control and the carnosine as a reference of the literature. The proportion of adducts formed with the MGO or MDA (generally, $t_R$=4.1 to 6.8 min) is then measured in relation to the quantity of remaining free scavenger (generally, $t_R$=0.8 to 4.6 min) after measurement of the area under the curve of the corresponding peaks on the UV spectrum (measurements taken for a representative sample).

3—Results and Discussion a) Evaluation of the Formation of Adducts with the MGO (FIG. 2)

Figure 3:
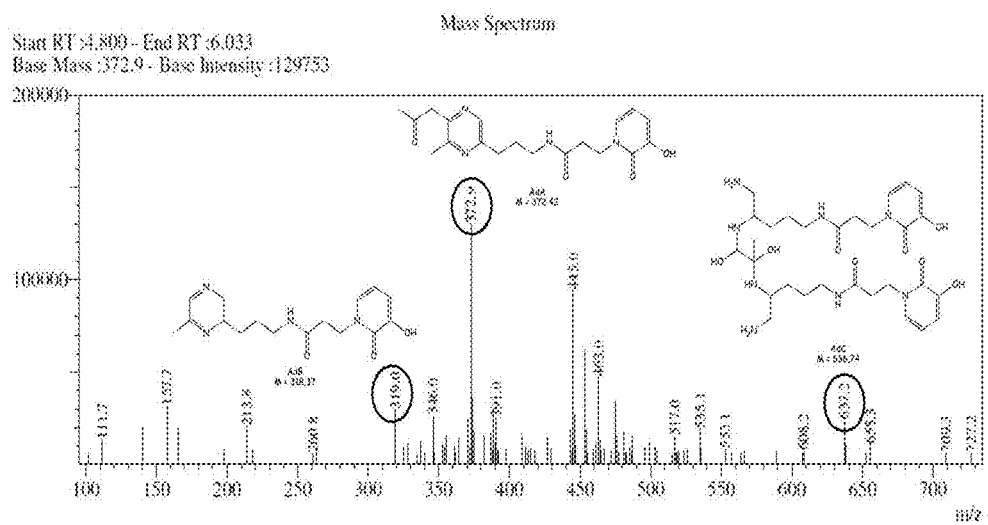

First of all, a disappearance of the free scavenger is observed to the benefit of various adducts with the MGO that is much faster with the novel compounds according to the invention than with the 2$^{nd}$ generation derivatives (Dap-Pip and Dap-(nBu)Pip) or the carnosine (FIG. 2). The increased effectiveness of this novel series of diamine derivatives as MGO scavengers, linked to the separation of the carbonyl group with respect to the diamine function, was therefore able to be demonstrated. Compounds 37a, 37b, 37c, 37f, 37i and 37j carrying a hydroxypyridinone group appear in addition as the most reactive with an activity comparable to that of hydralazine and an almost total disappearance of the free scavenger after 15 min of incubation. We were also able to identify three types of possible adducts with the MGO (Adduct A (AdA) of type 1:1 which is a scavenger molecule for two molecules of MGO; Adduct B (AdB) of type 1:2; Adduct C (AdC) of type 2:1 with a frequent change to the observation of a majority adduct of type 1:2, carrying a pyrazine cycle (AdB) (FIG. 3). Finally, note that the results obtained with the compound 29a were not able to be represented graphically (ND=Not Determined) because it was not possible to obtain a separation between the free scavenger and the adducts with the MGO in this case during the HPLC analysis. However, a trend towards a majority presence of AdB with regards to the free scavenger seems to be formed after 5 h of reaction.

b) Evaluation of the Formation of Adducts with the MDA (FIG. 4)

Figure 5:
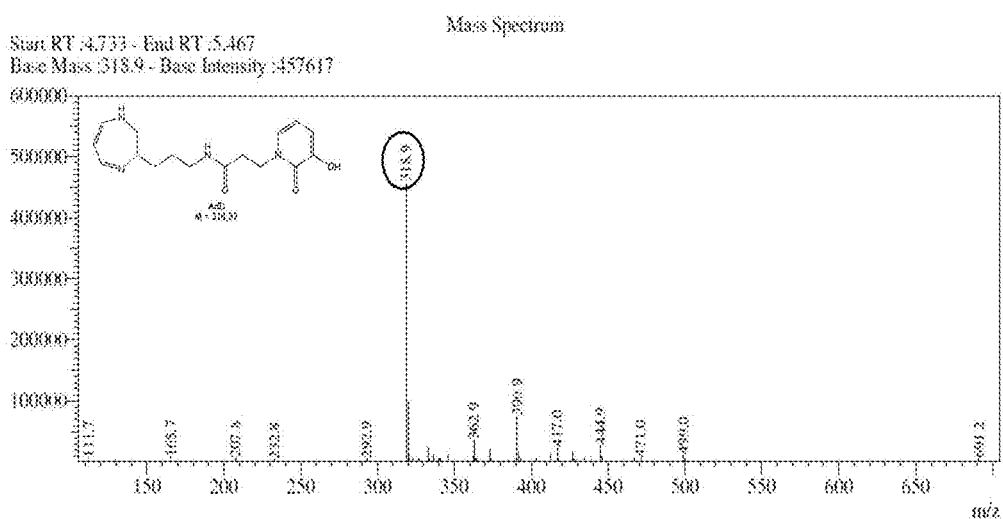

In particular the formation of an adduct carrying a 2,3-dihydro-1H-1,4-diazepine (Adduct D (AdD)) cycle is observed with all of the compounds according to the invention (FIG. 4 and FIG. 5). The derivatives 30b, 37c, 37d, 37f, 37i and 37j have shown to be the most reactive with a consequent disappearance of the scavenger tested to the benefit of the adducts with the MDA after 1 h (>81% of adducts). Note that the results obtained with the compound 29a were again not able to be represented graphically (ND=Not Determined) because as with the MGO, we were not able to find any separation between the free scavenger and the adducts with the MDA during the HPLC analysis. In this case, a trend towards a majority presence of AdD with regards to the free scavenger seems to be formed only after 24 h of reaction.

II) Evaluation of the Cu$^{2+}$ Chelating Properties of the Compounds According to the Invention ((29a, 29b, 30a, 30b; 37a, 37b, 37c, 37d, 37f, 37i, 37j) by UV/Visible Light Spectrophotometry 1—Principle:

The compounds to be tested are incubated at RT in the presence of Cu$^{2+}$ for 10 min. The remaining quantity of free Cu$^{2+}$ is determined after complexation by the murexide (*Int. J. Mol. Sci.*, 2009, 10, 5485-5497; *Molecules*, 2012, 17, 13457-13472). A measurement of the absorbance at 485 nm ($A_{485}$) of the Cu$^{2+}$/murexide (orange) complex and of the absorbance at 520 nm ($A_{520}$) of the free murexide (pink) is indeed taken by UV/Visible light spectrophotometry. The remaining quantity of free Cu$^{2+}$ is then evaluated using the straight-line calibration equation giving the ratio $A_{485}/A_{520}$ according to the concentration in Cu$^{2+}$ obtained beforehand. From this was deduced in the end the percentage of complexation of the Cu$^{2+}$ by the compounds tested.

2—Method:

a) Preparation of the Solutions

A Hexamine buffer 0.01 M/KCl 0.01 M (qsp 200 mL) of which the pH is adjusted to 5 using a solution of HCl 1N is first of all prepared. Solutions of CuSO$_4$.5H$_2$O at 0.5 mM (20 mL) and 0.25 mM (100 mL) are then carried out in this buffer, with the first being used to obtain the calibration curve. An aqueous solution of murexide at 1 mM must also be prepared extemporaneously (10 mL) as well as a stock solution of the compounds to be tested at 4.2 mM in Hexamine buffer 0.01 M/KCl 0.01 M or in a buffer and MeOH 75/25 mixture (6.2 mL).

b) Incubation of the Mixtures at RT

Various concentrations of the compounds to be tested are distributed in Hexamine buffer 0.01M/KCl 0.01M (pH=5) (Table 5) or in a buffer and MeOH 75/25 mixture in tubes for hemolysis (Table 6). The solution of CuSO$_4$.5H$_2$O at 0.25 mM (1 mL) is then added and this is allowed to incubate at RT for 10 min. Finally, the aqueous solution of murexide at 1 mM (0.1 mL) is introduced and is again allowed to incubate at RT for 1 min. The absorbances are then measured at 485 nm ($A_{485}$) and 520 nm ($A_{520}$) by UV/Visible light spectrophotometry (V-650 JASCO spectrometer) (measurements taken in triplicates). A blank is used containing Hexamine buffer 0.01 M/KCl 0.01 M (pH=5) (2 mL) and water (0.1 mL), and ethylenediamine (EDA) as a reference of the literature as a $Cu^{2+}$ chelator.

TABLE 5

Preparation of the various concentrations of the compound to be tested in Hexamine buffer 0.01M/KCl 0.01M (pH = 5)

| Final concentration of the compound to be tested (mM) | Volume of the stock solution of the compound to be tested (μL) | Volume of Hexamine buffer 0.01M/ KCl 0.01M (pH = 5) (μL) |
| --- | --- | --- |
| 0 | 0 | 1000 |
| 0.02 | 10 | 990 |
| 0.05 | 25 | 975 |
| 0.08 | 40 | 960 |
| 0.10 | 50 | 950 |
| 0.20 | 100 | 900 |
| 0.50 | 250 | 750 |
| 1 | 500 | 500 |
| 2 | 1000 | 0 |

TABLE 6

Preparation of the various concentrations of the compound to be tested in a Hexamine buffer 0.01M/KCl 0.01M (pH = 5) and MeOH 75/25 mixture

| Final concentration of the compound to be tested (mM) | Volume of the stock solution of the compound to be tested (μL) | Volume of Hexamine buffer 0.01M/ KCl 0.01M (pH = 5) (μL) | Volume of MeOH (μL) |
| --- | --- | --- | --- |
| 0 | 0 | 750 | 250 |
| 0.02 | 10 | 743 | 247 |
| 0.05 | 25 | 731 | 244 |
| 0.08 | 40 | 720 | 240 |
| 0.10 | 50 | 713 | 237 |
| 0.20 | 100 | 675 | 225 |
| 0.50 | 250 | 563 | 187 |
| 1 | 500 | 375 | 125 |
| 2 | 1000 | 0 | 0 |

Calibration curves are produced beforehand after the distribution of the various concentrations of $CuSO_4 \cdot 5H_2O$ in Hexamine buffer 0.01 M/KCl 0.01 M (pH =5) (Table 7) or in a buffer and MeOH 75/25 mixture (Table 8) in tubes for hemolysis (measurements taken in triplicates). After introduction of the aqueous solution of murexide at 1 mM (0.1 mL), this is allowed to incubate at RT for 1 min and the absorbances are finally measured at 485 nm ($A_{485}$) and 520 nm ($A_{520}$) by UV/Visible light spectrophotometry.

TABLE 7

Preparation of the various concentrations of $CuSO_4 \cdot 5H_2O$ in Hexamine buffer 0.01M/KCl 0.01M (pH = 5) for the production of the calibration curves

| Final concentration of $CuSO_4 \cdot 5H_2O$ (mM) | Solution volume of $CuSO_4 \cdot 5H_2O$ at 0.5 mM (μL) | Volume of Hexamine buffer 0.01M/KCl 0.01M (pH = 5) (μL) |
| --- | --- | --- |
| 0 | 0 | 2000 |
| 0.025 | 105 | 1895 |
| 0.050 | 210 | 1790 |
| 0.075 | 315 | 1685 |
| 0.100 | 420 | 1580 |
| 0.125 | 525 | 1475 |

TABLE 8

Preparation of the various concentrations of $CuSO_4 \cdot 5H_2O$ in a Hexamine buffer 0.01M/KCl 0.01M (pH = 5) and MeOH 75/25 mixture for the production of the calibration curves

| Final concentration of $CuSO_4 \cdot 5H_2O$ (mM) | Solution volume of $CuSO_4 \cdot 5H_2O$ at 0.5 mM (μL) | Volume of Hexamine buffer 0.01M/KCl 0.01M (pH = 5) (μL) | Volume of MeOH (μL) |
| --- | --- | --- | --- |
| 0 | 0 | 1750 | 0.250 |
| 0.025 | 105 | 1645 | 0.250 |
| 0.050 | 210 | 1540 | 0.250 |
| 0.075 | 315 | 1435 | 0.250 |
| 0.100 | 420 | 1330 | 0.250 |
| 0.125 | 525 | 1225 | 0.250 |

3—Results and Discussion:

a) Calibration Curves

Straight lines are obtained (FIG. 6, FIG. 7) of which the equations will make it possible to determine the remaining quantity of free $Cu^{2+}$, after complexation by the compounds to be tested and to evaluate in the end the complexation power thereof of the $Cu^{2+}$.

b) Comparison of the $Cu^{2+}$ Chelating Properties of the Tested Compounds

Figure 9:
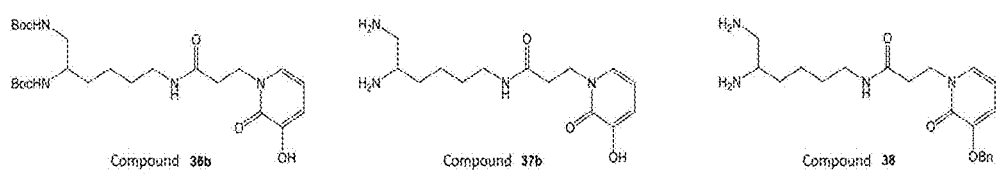
Figure 10:
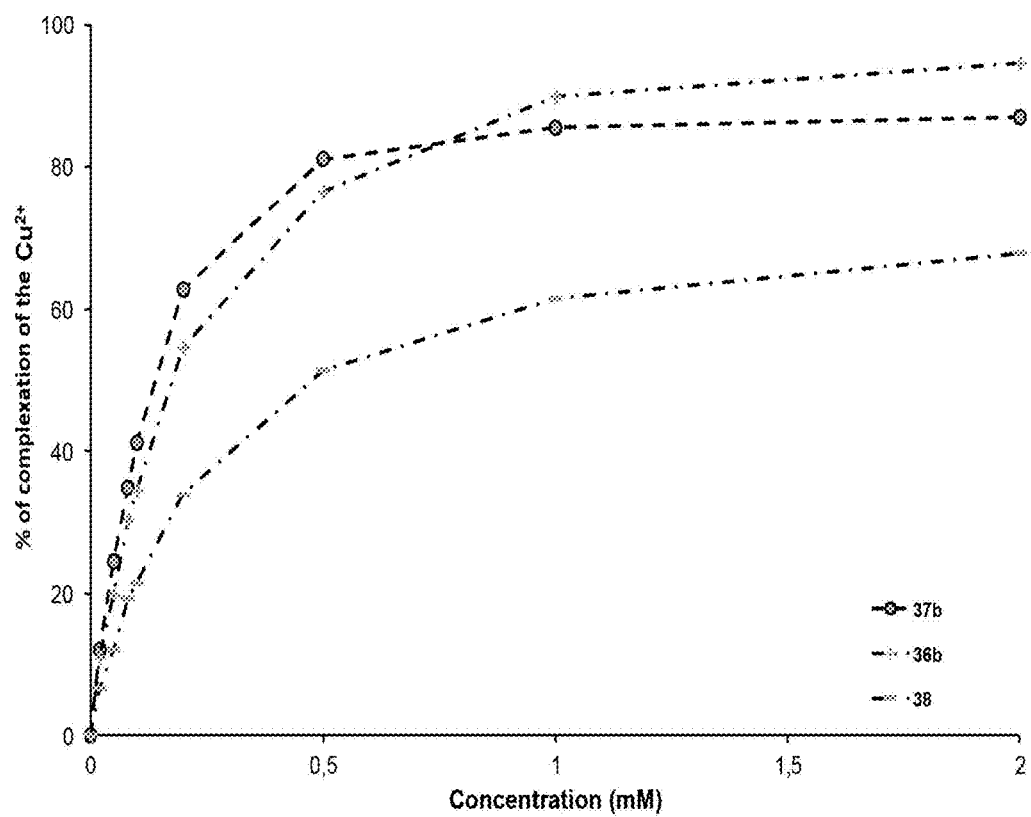

First of all, the novel compounds according to the invention appear to be better $Cu^{2+}$ chelators than the $2^{nd}$ generation derivatives (Dap-Pip and Dap-(nBu)Pip) (FIG. 8). Compounds 30b, 37b, 37i and 37j have as such shown to be the most active with a complexing power close, especially for the compound 30b, to that of the EDA used as a reference of the literature. Within the same series, the comparison of the $Cu^{2+}$ chelating properties of compounds 37a and 37b (compound 37b better complexant that the compound 37a) shows that the extension of the carbon chain carrying the terminal diamine group seems as expected to improve the activity. The separation of the carbonyl function does indeed allow for a potentialisation of the chelating ability of the diamine group. However, the poor results obtained with the compound 29b in relation to those obtained with the compounds 30b and 37b of which the carbon chain is also derived from lysine, suggests a combined intervention in the complexation of the $Cu^{2+}$ of the group derived from ferulic acid, from gallic acid or hydroxypyridinone introduced at the opposite end of the molecule. In order to validate this hypothesis, we therefore compared the $Cu^{2+}$ chelating properties of the compounds 37b and of two related compounds having only one free $Cu^{2+}$ chelating end (compounds 36b and 38) (FIG. 9 and FIG. 10). As such, the loss of the diamine group (compound 36b) has shown to be of hardly any consequence contrary to that of the hydroxypyridinone group (compound 38) which appears therefore indeed essential for the $Cu^{2+}$ chelating activity of the novel compounds according to the invention. In addition, the comparison of the results obtained with the compounds 37c and 37j shows a complexing power of the $Cu^{2+}$ that is more substantial of the 3-hydroxy-2-methylpyridin-4-one motif with regards to the 3-hydroxypyridin-2-one motif. Finally, in light of the poor results obtained with the compounds 29a and 29b, the group derived from ferulic acid seems to have the complexing power of the $Cu^{2+}$ that is the least interesting.

III) Evaluation of the Antioxidant Properties of the Compounds According to the Invention (29a, 29b, 30a, 30b; 37a, 37b, 37c, 37d, 37f, 37i, 37j) via an ORAC Test ("Oxygen Radical Absorbance Capacity")

1—Principle:

The antioxidant properties of the compounds according to the invention were evaluated using a $ORAC_{FL}$ test using fluorescein (J. Agric. Food Chem., 2004 52, 48-54; J. Agric. Food Chem., 2005, 53, 4290-4302). As such, peroxide radicals, generated in the presence of AAPH (2,2'-azobis(2-methylpropionamidine)dihydrochloride) at 37° C., react with this fluorescent sensor in order to give a non-fluorescent product. The protective effect of the test compounds can then be determined by following the decay curve of the fluorescence of the fluorescein over time and be measuring the area under the curve (AUC) of the sample in relation to that of a control corresponding to an absence of antioxidant.

Figure 11:
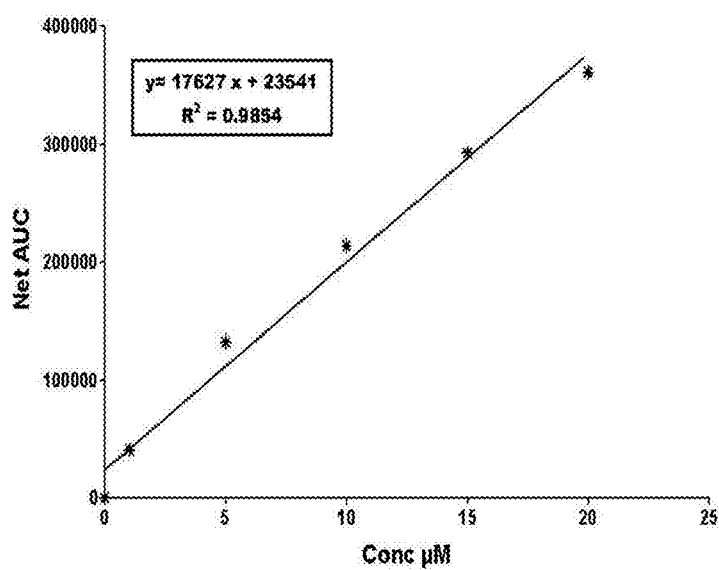

The trolox (6-hydroxy-2,5,7,8-tetramethylchroman-2-carboxylic acid), a water-soluble analogue of vitamin E, is used as a standard for calculating the antioxidant capacity ($ORAC_{FL}$) of the compounds tested at 10 µM, expressed in mol of Trolox equivalent (TE)/µmol of tested compound. This value is as such obtained using the straight-line calibration equation giving the area under the curve according to the various concentrations of trolox (Bioorg. Med. Chem., 2015, 23, 1135-1148) (FIG. 11).

2—Method:

A solution of fluorescein (FL) (12 nM; 150 µL) is introduced into a black 96-well plate (Dutscher, Brumath, France). The compounds to be tested (1-20 µM; 25 µL) or trolox (1-50 µM; 25 µL) dissolved in D-PBS are added into each well. After equilibration of the plate during an incubation at 37° C. for a minimum of 30 min, the radical reactions are initiated using a solution of AAPH prepared extemporaneously (30 mM; 25 µL). The fluorescence ($\lambda_{Ex}$: 485 nm; $\lambda_{Em}$: 520 nm) is measured every 90 seconds for 60 cycles using a temperature-controlled Tecan Infinite® 200 PRO microplate reader (measurements taken in triplicates during three independent experiments).

3—Results and Discussion:

The compounds according to the invention have shown a substantial antioxidant capacity (Table 9: $ORAC_{FL} \geq 1$ µmol TE/µmol), compared in particular to the very low activity found for the carnosine. In addition, the introduction of the group coming from ferulic acid, from gallic acid or from the hydroxypyridinone motif appears indispensable for the acquisition of these antioxidant properties in light of the absence of activity found for the 2$^{nd}$ generation Dap-Pip derivative. Compounds 30b and 37c have as such shown to be the most active and will therefore be retained as the leaders in their respective families thereof. Note that the comparison of the results obtained with the compounds 37c and 37j was in this case in favour of a better antioxidant capacity of the 3-hydroxypyridin-2-one motif

TABLE 9

Antioxidant capacity ($ORAC_{FL}$) of the compounds according to the invention at 10 µM (The values are expressed by the mean ± SEM ("Standard error of the mean") of three independent experiments conducted in triplicate).

| Compound tested | $ORAC_{FL}$ (µmol TE/µmol) |
| --- | --- |
| Trolox | 1 |
| Carnosine | 0.08 ± 0.05 |
| Dap-Pip | 0 |
| Compound 29a | 2.05 ± 0.23 |
| Compound 29b | 1.50 ± 0.10 |
| Compound 30a | 0.89 ± 0.10 |
| Compound 30b | 2.59 ± 0.35 |
| Compound 37a | 0.58 ± 0.02 |
| Compound 37b | 0.99 ± 0.09 |
| Compound 37c | 1.03 ± 0.03 |
| Compound 37d | 1.21 ± 0.07 |
| Compound 37f | 1.96 ± 0.24 |
| Compound 37i | 1.24 ± 0.02 |
| Compound 37j | 1.01 ± 0.06 |

C. Biological Evaluation In Vitro

I) Evaluation In Vitro of the Antiradical Properties of the Compounds According to the Invention (29a, 29b, 30a, 30b; 37a, 37b, 37c)

1—Principle:

The antiradical properties of the various compounds are determined by inhibition of the lipid peroxidation in the in vitro model of the oxidation of the low-density lipoproteins (LDLs) (Free Radic. Biol. Med., 1992, 13, 341-390). The lipid peroxidation is initiated by the attack by free radicals of a double bond of a polyunsaturated fatty acid present in the LDLs. This results in the elimination of a hydrogen atom from a $CH_2$ group. This unstable radical is rearranged in order to then result in a more stable configuration namely a conjugated diene. Once initiated, the oxidation of the LDLs is a chain reaction of lipid peroxidation generated by the free radicals. The oxidation in vitro of the LDLs is induced at 37° C. by the adding of the water-soluble compound 2,2'-Azobis (2-methylpropionamidine)dihydrochloride (AAPH), which generates free radicals during the spontaneous thermal breakdown thereof 2—Method:

Briefly, the oxidation, carried out in a 96-well plate, is induced at 37° C. by adding 20 µL of a solution of AAPH at 2 mM in D-PBS at 160 µL of LDL (100 µg/mL) in the presence or absence of 20 µL of the various solutions of the compounds to be tested dissolved in D-PBS (0.1 to 100 µM in final concentrations). The LDLs alone without adding AAPH are used as a negative control. Each oxidation is carried out in double. During the oxidation, the formation of the conjugated dienes is followed by the measurement of the optical density at 234 nm every 10 minutes for 8 h at 37° C. using a temperature-controlled TECAN spectrophotometer. The vitamin E (α-tocopherol) which is a powerful antioxidant recognised in this in vitro model is used as a reference molecule (J. Nutr. Biochem., 2012, 23, 845-51).

3—Results and Discussion:

The 2$^{nd}$ generation Dap-Pip derivative does not show any anti-radical effect even at a high concentration (100 µM) (FIG. 27).

Figure 28:
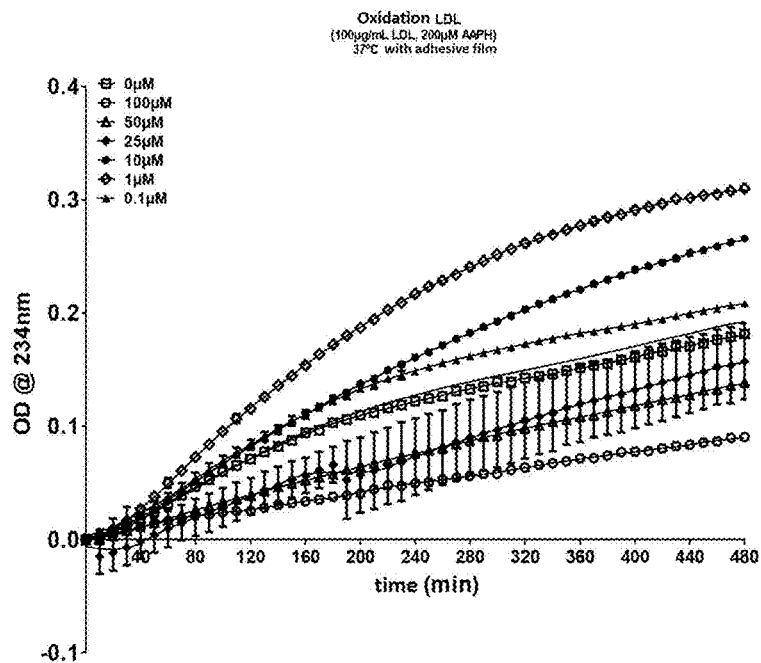
Figure 29:
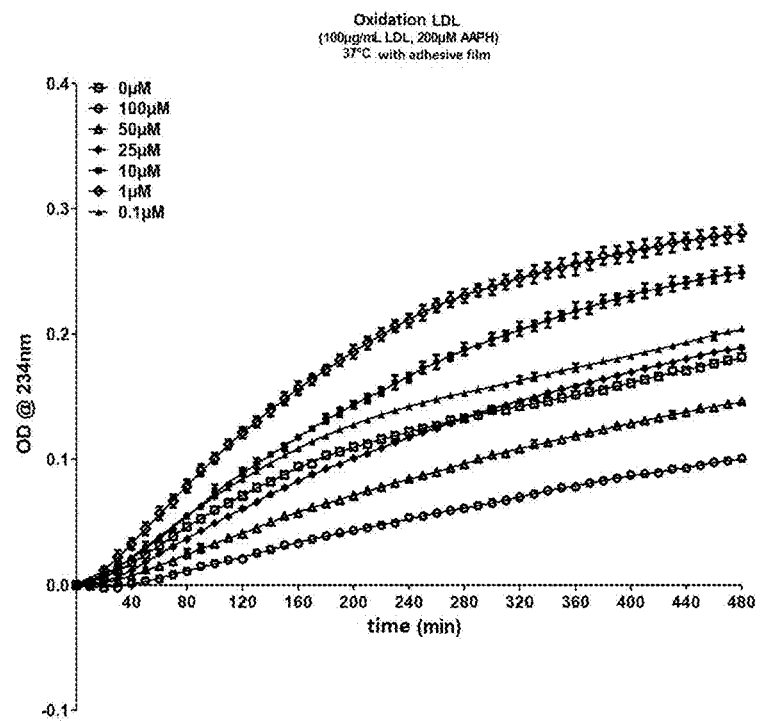

Compounds 29a and 29b, derived from ferulic acid behave in a similar way (FIG. 28 and FIG. 29). Indeed, the results show that these products are antioxidants for concentrations ranging from 25 to 100 but become pro-oxidants at lower concentrations (from 0.1 to 10 µM).

Figure 30:
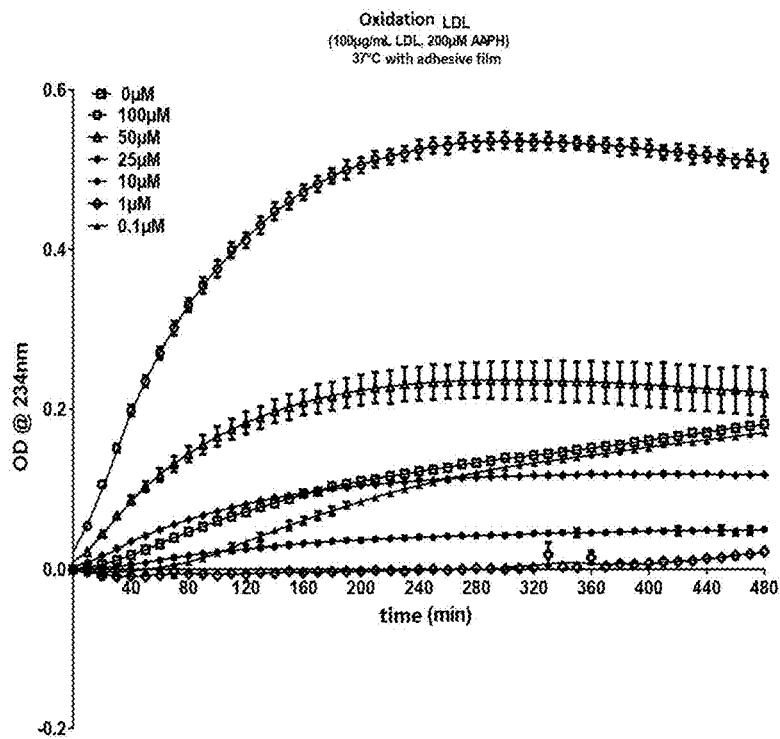

The compound 30b, derived from gallic acid is highly pro-oxidant for concentrations ranging from 50 to 100 but becomes highly antioxidant at the lowest concentrations (0.1 to 10 µM) (FIG. 30).

Figure 31:
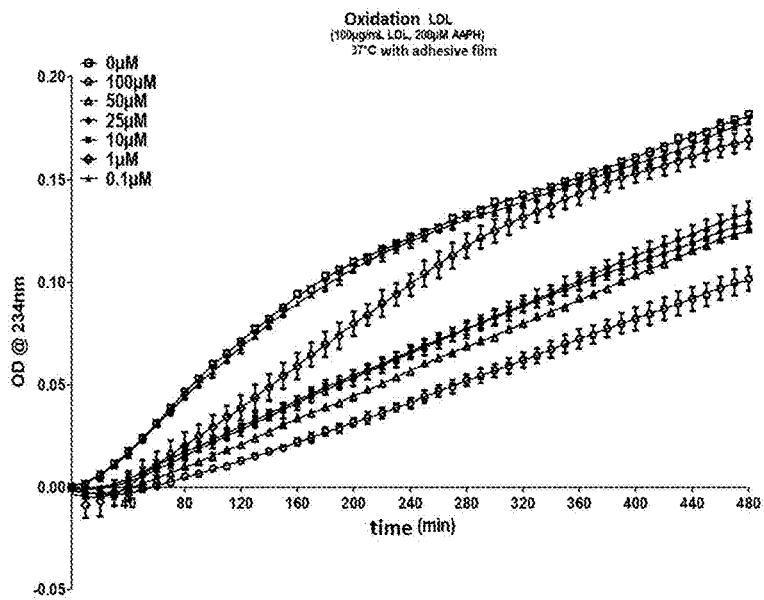
Figure 32:
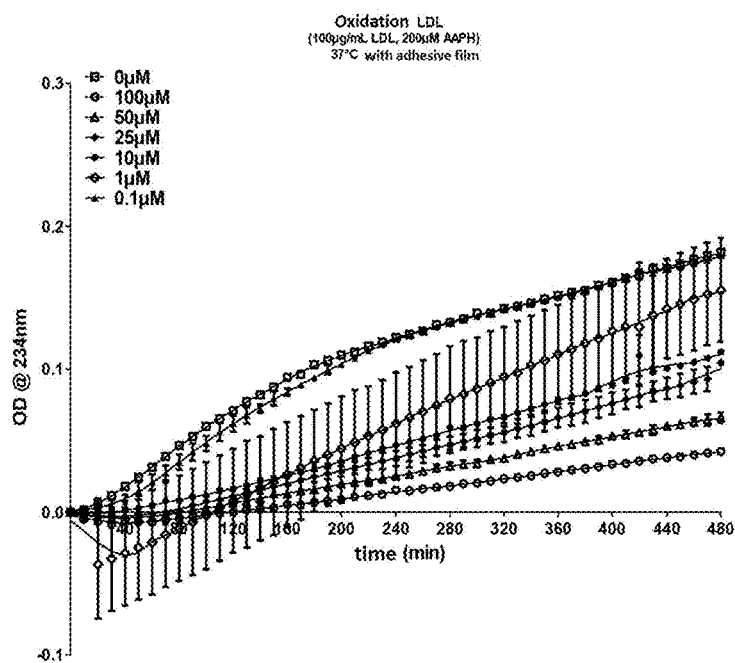

Compounds 37a and 37c, carrying a hydroxypyridinone group behave in a similar way. They have an increasing antioxidant effect for concentrations ranging from 1 to 100 (FIG. 31 and FIG. 32).

Figure 33:
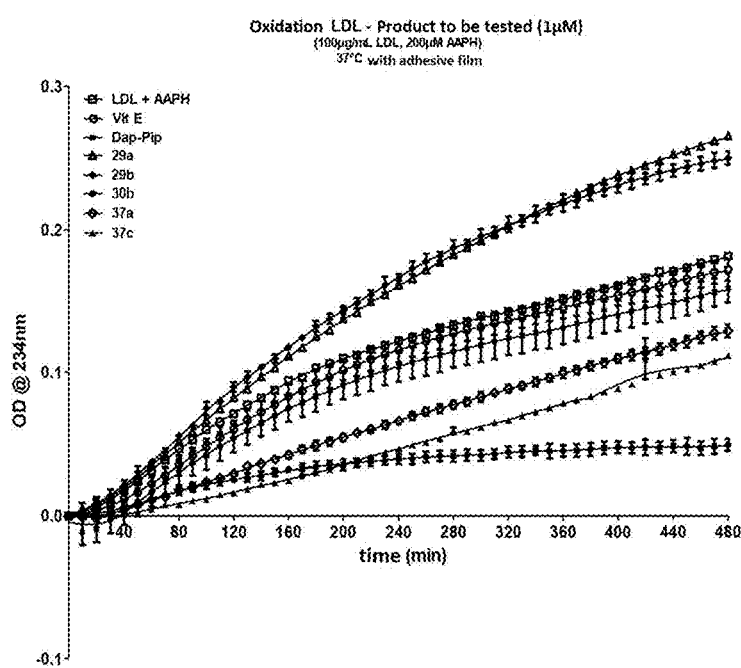
Figure 34:
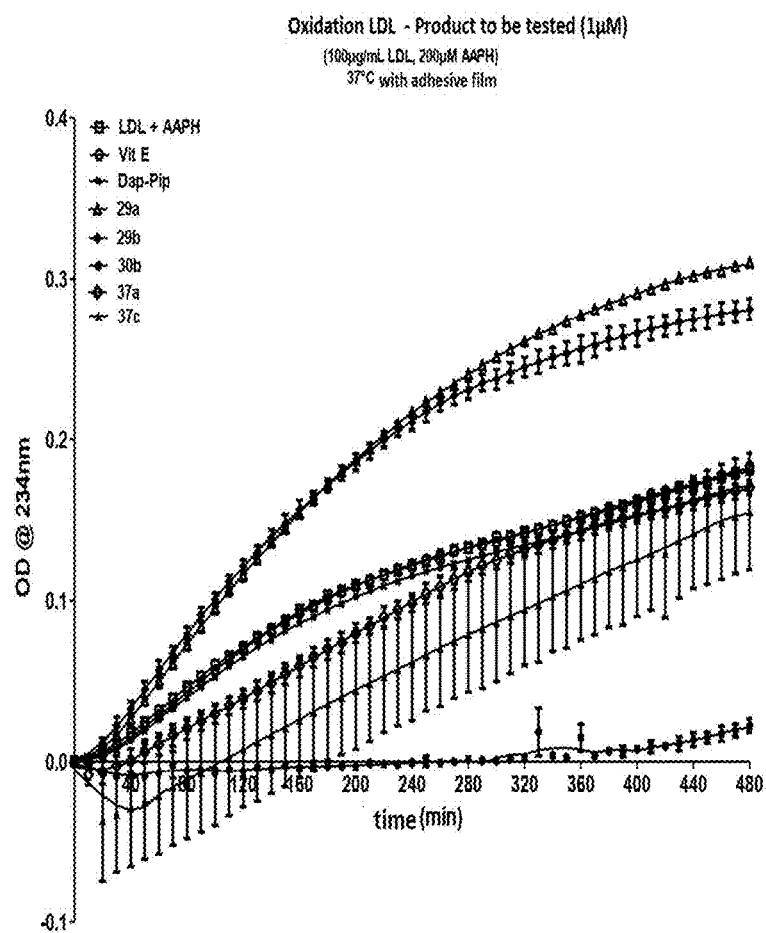
Figure 35:
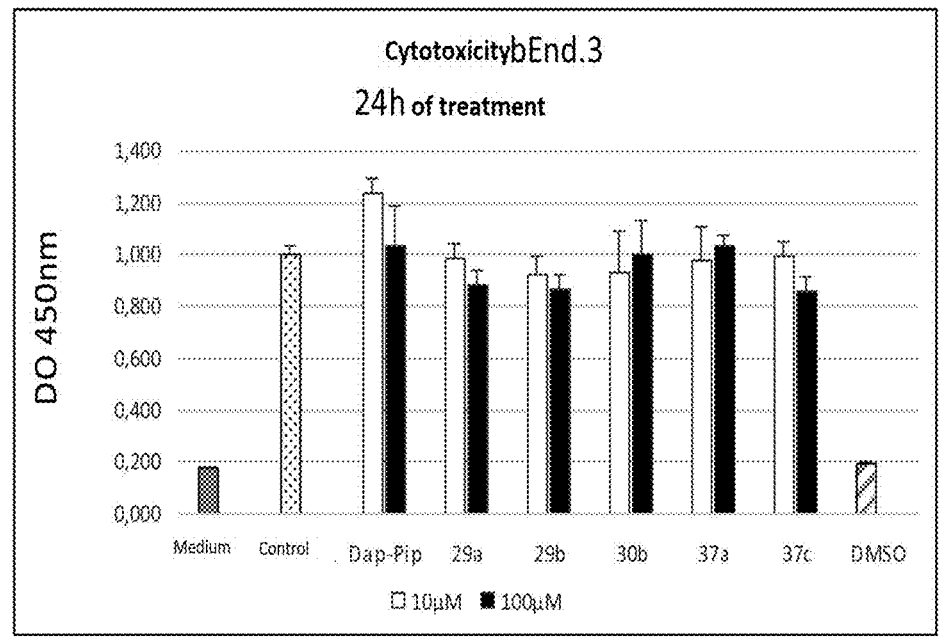
Figure 35:
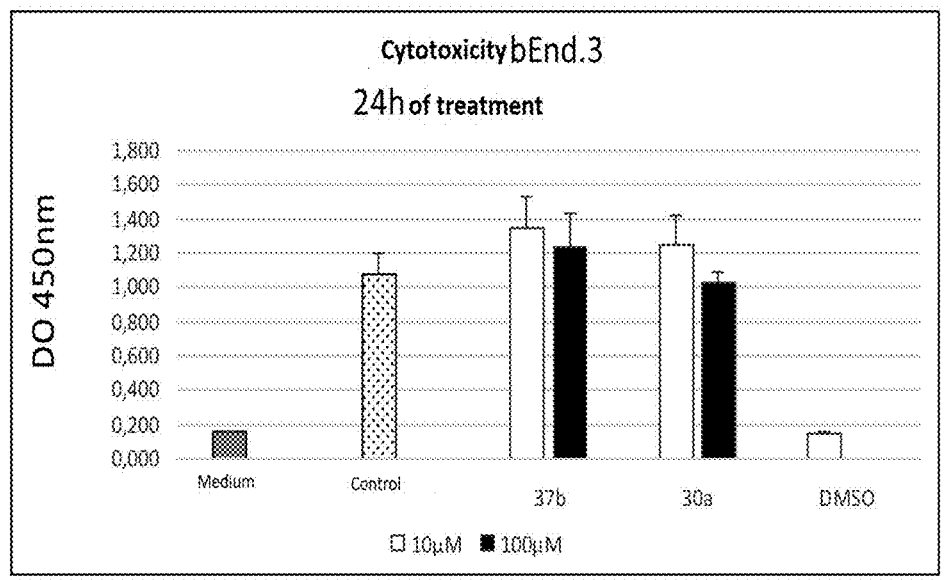

At lower concentrations from 1 to 10 μM, the compounds 30b, 37a and 37c according to the invention have antiradical properties that are higher than those of the $2^{nd}$ generation Dap-Pip derivative, and even those of vitamin E (FIG. 33 and FIG. 34). The effectiveness of this $3^{rd}$ generation of antioxidant compounds with respect to both prior related derivatives, but also a reference product, was therefore able to be demonstrated.

The rather atypical behaviour of the compound 30b (antioxidant at low concentrations and pro-oxidant at high concentrations) is yet to be studied. On the contrary, the profile of compounds 29a and 29b (pro-oxidant at low concentrations and antioxidant at high concentrations) can be echoed in certain recent work described in literature (*J. Agric. Food Chem.*, 2000, 48, 3597-3604; *J. Agric. Food Chem.*, 2010, 58, 9273-9280).

In the end, the compounds 37a and 37c carrying a hydroxypyridinone group seem to have the best antioxidant properties and this at low concentrations of about 1 μM.

II) Study of the Cytotoxicity of the Compounds According to the Invention

The cell lines used for the study of the cytotoxicity of the compounds according to the invention as well as for the evaluation of the anti-apoptotic properties thereof were selected in light of the previously mentioned claims, for the purposes of a use in cosmetics or in the treatment and/or the prevention in particular of atherosclerosis and of neurodegenerative diseases of the compounds according to the invention. As such, these various studies were able to be carried out on human fibroblasts (MRC-5), murine endothelial brain cells (bEnd.3) and rat pheochromocytoma cells, treated as neuronal cells (PC12) (*Eur. J. Med. Chem.*, 2014, 83, 355-365; *Chem. Biol. Interact.*, 2014, 224, 108-116; *Neurochem. Int.*, 2013, 62, 620-625).

1—Principle:

The cellular viability is evaluated by a colorimetric method based on the detection of the conversion of a salt of the tetrazolium (WST-8) by the metabolically active cells (CCK-8 kit, Sigma, Lyons, France) (*Molecules*, 2014, 19(8), 12048-12064; *J. Pharmacol. Toxicol. Methods.*, 2007, 56(1), 58-62). Living cells have mitochondrial dehydrogenases that reduce the WST-8 (2-(2-methoxy-4-nitrophenyl)-3-(4-nitrophenyl)-5-(2,4-disulfophenyl)-2H-tetrazolium), monosodium salt) to formazan of an orange colour, which dissolves directly in the culture medium in the presence of 1-Methoxy PMS (1-methoxy-5-methylphenazinium methyl sulphate). After an incubation for 1 h at 37° C., the absorbance of the formazan is measured at 450 nm. The absorbance is directly proportional to the number of living cells.

2—Method:

Briefly, the cells are inoculated in 96-well plates at a rate of $5.10^3$ cells per well in 100 μL of the suitable medium until subconfluence. The cells are then washed with D-PBS, then treated with various concentrations (10 μM, 100 μM) of the products to be tested in triplicates for 24 and 48 h. A positive control is carried out with 10% of DMSO. The CCK-8 (10 μL) solution is then added to each well for an incubation for 1 h at 37° C. The measurement of the absorbance is taken at 450 nm using a Perkin Elmer 2103 Envision® microplate reader.

The viability of the cells is expressed as a % of the control (untreated cells) by the mean±standard deviation of triplicates forming a representative experiment or of three independent experiments conducted in triplicate.

3—Results and Discussion:

TABLE 10

Study of the cytotoxicity of the compounds according to the invention on three cell lines (murine endothelial brain cells (bEnd.3), rat pheochromocytoma cells, treated as neuronal cells (PC12) and human fibroblasts (MRC-5)) after 24 h of treatment. The viability of the cells is expressed as a percentage of the untreated cells (100% control conditions).

| Cell line | bEnd.3 | | PC12 | | MRC-5 | |
|---|---|---|---|---|---|---|
| Concentration (μM) | 10 | 100 | 10 | 100 | 10 | 100 |
| Control | 100 | 100 | 100 | 100 | 100 | 100 |
| Dap-Pip | 123 | 103 | 114 | 120 | 125 | 128 |
| Compound 29a | 98 | 87 | 100 | 120 | 103 | 99 |
| Compound 29b | 92 | 86 | 108 | 112 | 106 | 102 |
| Compound 30a | 117 | 96 | 116 | 140 | 115 | 112 |
| Compound 30b | 93 | 99 | 110 | 82 | 98 | 101 |
| Compound 37a | 97 | 103 | 93 | 112 | 112 | 124 |
| Compound 37b | 126 | 115 | 138 | 124 | 113 | 113 |
| Compound 37c | 99 | 85 | 110 | 102 | 97 | 89 |

TABLE 11

Study of the cytotoxicity of the compounds according to the invention on three cell lines (murine endothelial brain cells (bEnd.3), rat pheochromocytoma cells, treated as neuronal cells (PC12) and human fibroblasts (MRC-5)) after 48 h of treatment. The viability of the cells is expressed as a percentage of the untreated cells (100% control conditions).

| Cell line | bEnd.3 | | PC12 | | MRC-5 | |
|---|---|---|---|---|---|---|
| Concentration (μM) | 10 | 100 | 10 | 100 | 10 | 100 |
| Control | 100 | 100 | 100 | 100 | 100 | 100 |
| Dap-Pip | 131 | 142 | 110 | 102 | 113 | 111 |
| Compound 29a | 90 | 83 | 94 | 87 | 104 | 103 |
| Compound 29b | 92 | 90 | 95 | 97 | 95 | 100 |
| Compound 30a | 95 | 108 | 96 | 113 | 101 | 103 |
| Compound 30b | 92 | 87 | 95 | 67 | 92 | 100 |
| Compound 37a | 99 | 93 | 96 | 99 | 107 | 105 |
| Compound 37b | 101 | 100 | 115 | 107 | 103 | 101 |
| Compound 37c | 86 | 84 | 91 | 94 | 94 | 90 |

The general trend that is formed from these first results (measurements taken in triplicates forming a representative experiment) reveal a priori a low cytotoxicity and even an absence of cytotoxicity of the compounds according to the invention on the three cell lines tested at 10 and 100 μM after 24 h (Table 10, FIG. 35, FIG. 36, FIG. 37) or 48 h of treatment (Table 11, FIG. 38, FIG. 39, FIG. 40). Some less satisfactory data does appear however especially for a high concentration of 100 μM for in particular the compounds 29a, 30b and 37c. The compound 30b is at such at the origin of a non-negligible reduction in cellular viability at 100 μM and after 48 h of treatment on the PC12 cells (67% control). However, this cytotoxicity could be explained by its pro-oxidant nature already observed at high concentration during the in vitro evaluation of the antiradical properties thereof (FIG. 30). In the end, an anti-radical activity higher than that of vitamin E having been found for the most interesting derivatives for concentrations less than or equal to 10 μM (FIG. 33, FIG. 34), these first results on the cytotoxicity of the compounds according to the invention appear to be highly encouraging.

Finally, the absence of cytotoxicity of the compounds according to the invention was able to be confirmed after 24 h of treatment on the PC12 cells during three independent experiments conducted in triplicate (FIG. 41).

III) Evaluation of the Anti-Apoptotic Properties of the Compounds According to the Invention on Different Cell Lines (29a, 29b, 30a, 30b; 37a, 37b, 37c)

1—Principle:

Apoptosis is an intrinsically programmed cellular mechanism for cell death, highly regulated, which constitutes a response of the organism to physiological or pathological stimuli causing an imbalance between the production and the elimination of cells. This programmed death mechanism makes it possible to maintain the homeostasis of the tissues. Morphologically, apoptosis corresponds to a progressive retraction of the cell, with condensation of the chromatin and of the cytoplasm, followed by a regular characteristic fragmentation of the DNA resulting in the formation of cell fragments (internucleosomal fragmentation) or apoptotic bodies. Unsuitable regulation of apoptosis plays a major role in many pathological conditions such as cancer, autoimmunity, Alzheimer's disease . . . (*The Lancet*, 1993, 381, 1251-1254; *Toxicol Pathol.*, 2007, 35(4), 495-516).

Various studies have shown that methyglyoxal (MGO) induces apoptosis in many cell types (*Int. J. Mol, Med.*, 2010, 26, 813-818).

The apoptosis of cells is evaluated by an ELISA method using two murine monoconal antibodies with one directed against the DNA and the other against the histones (ELISAPLUS Cell Death Detection kit, Roche, Meylan, France). This technique makes it possible to specifically measure the mono- and oligo-nucleosomes in the cytoplasmic fraction of the cell lysates.

2—Method:

Briefly, the cells are inoculated in 96-well or 24-well plates at a rate of $5.10^3$ cells/well for the Bend.3 and PC12 and $75.10^3$ cells/well for the MRCS in the suitable medium until subconfluence. The cells are then washed with PBS, then treated with various concentrations (10 µM, 100 µM) of the products to be tested in triplicates for 30 min to 1 h (cellules PC12 and Bend.3) or 1 h (cellules MRCS) at 37° C. The solution of MGO (1 mM for the cellules PC12, 2 mM for the cellules Bend.3 and MRCS) is then added for an incubation of 24 h. The concentrations of MGO for each cell type were chosen according to literature and a cytotoxicity test (CCK8) that we conducted. The solution of lyse is then added to each well for 30 min at room temperature. The cell lysates are then centrifuged at 200 g for 10 min. Twenty microliters of this cell lysate is then used for the ELISA according to the procedure described by the supplier. The cell lysates are as such applied to a plate covered with anti-Histones antibodies making it possible to view the fragmentation of the DNA. A peroxidase combined with anti-DNA antibodies then reacts in the presence of the substrate thereof, ABTS (diammonium 2,2'-azino-bis(3-ethylbenzothiazoline-6-sulphonate) and $H_2O_2$ in order to give a green derivative of which the optical density reflects the level of apoptosis. The measurement of the absorbance is taken at 405 nm using a Perkin Elmer 2103 Envision® microplate reader. A positive control is carried out in the presence of MGO alone.

The apoptosis of the cells is expressed by the mean±standard deviation of triplicates forming a representative experiment or of three independent experiments conducted in triplicate.

3—Results and Discussion:

Compounds 30b and 37c have shown very interesting anti-apoptotic properties starting at 10 µM following the induction of the apoptosis by the MGO on murine endothelial brain cells (bEnd.3) (FIG. 42, FIG. 43). They therefore appear to be capable of slowing down the harmful cellular cascade linked to the oxidative and carbonyl stresses with the purpose of using compounds according to the invention in the treatment and/or prevention of atherosclerosis.

The compound 37c revealed very interesting anti-apoptotic properties starting at 10 µM following the induction of the apoptosis by the MGO on rat pheochromocytoma cells, treated as neuronal cells (PC12) (FIG. 44, FIG. 45). It therefore appears to be capable of slowing down the harmful cellular cascade linked to the oxidative and carbonyl stresses with the purpose of using compounds according to the invention in the treatment and/or prevention of neurodegenerative diseases. For the compound 30b, this trend is confirmed at 100 µM.

Compounds 37b and 37c have promising anti-apoptotic properties at 100 µM following the induction of the apoptosis by the MGO on human fibroblasts (MRC-5) (FIG. 46, FIG. 47). They therefore appear to be capable of slowing down the harmful cellular cascade linked to the oxidative and carbonyl stresses for the purposes of an application of the compounds according to the invention in the cosmetic industry for a prevention of premature ageing of the skin.

Finally, the anti-apoptotic properties of the compound 37c at 100 µM following the induction of the apoptosis by the MGO on rat pheochromocytoma cells, treated as neuronal cells (PC12) were able to be confirmed during three independent experiments conducted in triplicate (FIG. 48).

The invention claimed is:

1. Compound of Formula I:

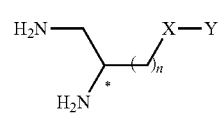

and the salts thereof, wherein n is an integer from 1 to 6;

X is CO or $CH_2$;

Y is $NR^1R^2$ or $R^2$ or

$R^1$ is H or alkyl or alkyl-aryl;

$R^2$ is Z-L-$R^3$;

Z is non-existent, CO or $CH_2$;

L is non-existent, CH=CH or $(CH_2)_m$;

m is an integer from 1 to 6;

$R^3$ is phenyl, substituted by at least one OH group and one or more substituents selected from OH, C1 to C4 alkoxy and C1 to C4 alkyl, or $R^3$ is N-pyridinonyl, substituted by at least one OH group and possibly by one or more substituents selected from OH, C1 to C4 alkoxy and C1 to C4 alkyl.

2. Compound or salt according to claim 1, having Formula II

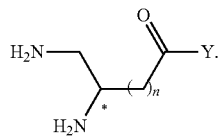

II.

3. Compound or salt according to claim 1, having Formula III

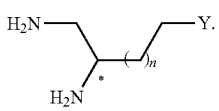

4. Compound or salt according to claim 1, having Formula IV

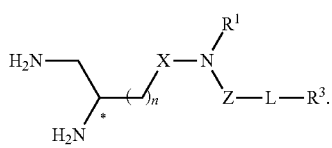

5. Compound or salt according to claim 1, having Formula V

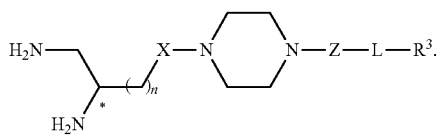

6. Compound or salt according to claim 4, wherein Z-L-R³ is selected from:

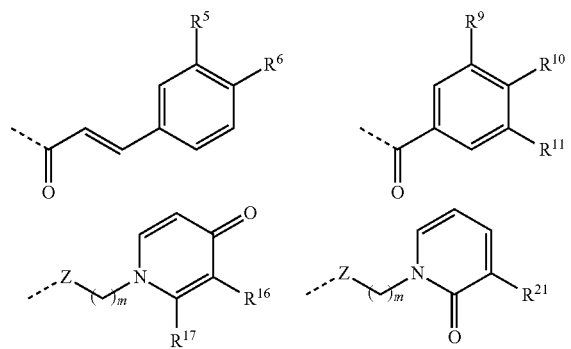

wherein R⁵, R⁶, R⁹, R¹⁰, R¹¹, R¹⁶, R¹⁷ and R²¹ are selected, independently of one another, from OH, C1 to C4 alkoxy and C1 to C4 alkyl.

7. Compound or salt according to claim 1, having Formula VI

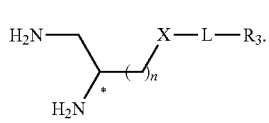

8. Compound or salt according to claim 1 selected from:
(E)-4,5-diamino-1-(4-(3-(4-hydroxy-3-methoxyphenyl)acryloyl)piperazin-1-yl)pentan-1-one,
(E)-N-(5,6-diaminohexyl)-3-(4-hydroxy-3-methoxyphenyl)acrylamide,
4,5-diamino-1-(4-(3,4,5-trihydroxybenzoyl)piperazin-1-yl)pentan-1-one,
N-(5,6-diaminohexyl)-3,4,5-trihydroxybenzamide,
N-(4,5-diaminopentyl)-3-(3-hydroxy-2-oxopyridin-1(2H)-yl)propanamide,
N-(5,6-diaminohexyl)-3-(3-hydroxy-2-oxopyridin-1(2H)-yl)propanamide,
4,5-diamino-N-(3-(3-hydroxy-2-oxopyridin-1(2H)-yl)propyl)pentanamide,
1-(2-(4-(4,5-diaminopentanoyl)piperazin-1-yl)-2-oxoethyl)-3-hydroxypyridin-2(1H)-one,
N-(4,5-diaminopentyl)-2-(3-hydroxy-2-methyl-4-oxopyridin-1(4H)-yl)acetamide,
N-(5,6-diaminohexyl)-2-(3-hydroxy-2-methyl-4-oxopyridin-1(4H)-yl)acetamide,
1-(2-(4-(4,5-diaminopentanoyl)piperazin-1-yl)-2-oxoethyl)-3-hydroxy-2-methylpyridin-4(1H)-one,
1-(3-(4-(4,5-diaminopentyl)piperazin-1-yl)propyl)-3-hydroxypyridin-2(1H)-one,
1-(3-((4,5-diaminopentyl)(methyl)amino)propyl)-3-hydroxypyridin-2(1H)-one, and
1-(5,6-diaminohexyl)-3-hydroxy-2-methylpyridin-4(1H)-one.

9. Pharmaceutical composition comprising at least one compound or one of the pharmaceutically acceptable salts thereof according to claim 1 and at least one pharmaceutically acceptable excipient.

10. Cosmetic composition comprising a compound according to claim 1.

11. Agrofood composition comprising a compound according to claim 1.

12. Compound or salt according to claim 5, wherein Z-L-R³ is selected from:

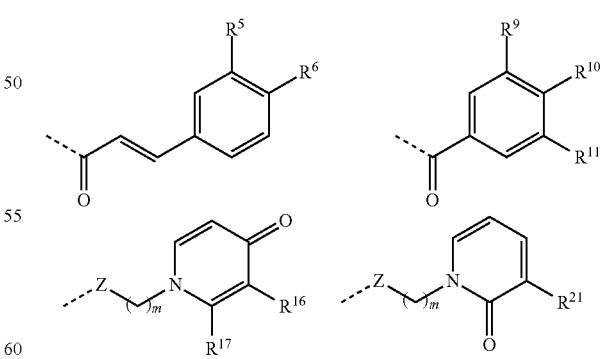

wherein R⁵, R⁶, R⁹, R¹⁰, R¹¹, R¹⁶, R¹⁷ and R²¹ are selected, independently of one another, from OH, C1 to C4 alkoxy and C1 to C4 alkyl.

* * * * *